(12) United States Patent
Pestano et al.

(10) Patent No.: US 11,542,340 B1
(45) Date of Patent: Jan. 3, 2023

(54) ANTIBODIES TARGETING PULMONARY NODULE SPECIFIC BIOMARKERS AND USES THEREOF

(71) Applicant: Biodesix, Inc., Boulder, CO (US)

(72) Inventors: Gary A. Pestano, Lafayette, CO (US); Hestia Meliert, Longmont, CO (US)

(73) Assignee: Biodesix, Inc., Boulder, CO (US)

( * ) Notice: Subject to any disclaimer, the term of this patent is extended or adjusted under 35 U.S.C. 154(b) by 33 days.

(21) Appl. No.: 17/514,737

(22) Filed: Oct. 29, 2021

(51) Int. Cl.
*C07K 16/28* (2006.01)
*C07K 16/18* (2006.01)

(52) U.S. Cl.
CPC .......... *C07K 16/2896* (2013.01); *C07K 16/18* (2013.01)

(58) Field of Classification Search
None
See application file for complete search history.

(56) References Cited

U.S. PATENT DOCUMENTS

2008/0038260 A1* 2/2008 Ponath ............. C07K 14/70503
530/387.3

2015/0196663 A1* 7/2015 Shusta ................. A61K 9/0085
435/254.11
2015/0266947 A1* 9/2015 Sierks ..................... A61P 25/28
435/6.12
2017/0355756 A1* 12/2017 Julien ....................... A61P 9/10

FOREIGN PATENT DOCUMENTS

WO     WO 2008068048     *   6/2008

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*

* cited by examiner

*Primary Examiner* — Adam Weidner
(74) *Attorney, Agent, or Firm* — Foley Hoag LLP; Hathaway P. Russell; Jack Rosa

(57) ABSTRACT

Provided are monoclonal antibodies, or antigen-binding fragments thereof, that bind to specific peptides of C163A or LG3BP, compositions comprising such antibodies and/or fragments, as well as methods of use and devices employing such antibodies and/or fragments.

18 Claims, 15 Drawing Sheets
Specification includes a Sequence Listing.

Cell Line: C163A-BA-1.3-13G05-02E09

IEF Parameters:

pI range of IEF gel: 3-10       IEF Gel Lot No: 64257839

IEF Standard (pI 4.45-9.6) Lot No: 64174547

Antibody quantity per well: 20 µg

Focusing Conditions:    100 volts, 1hr
                        250 volts, 1hr
                        500 volts, 30min Image of IEF Gel Lane 1: pI markers lot# 64174547
Lane 2: C163A-BA-1.3-13G05-02E09 lot# 190422RB.1P Cell Line: C163A-BA-1.3-13H05-02F02

IEF Parameters:

pI range of IEF gel: 3-10                    IEF Gel Lot No: 64257839

IEF Standard (pI 4.45-9.6) Lot No: 64174547

Antibody quantity per well: 20 μg

Focusing Conditions:   100 volts, 1hr
                       250 volts, 1hr
                       500 volts, 30min Image of IEF Gel Lane 1: pI markers lot# 64174547
Lane 2: C163A-BA-1.3-13H05-02F02
lot# 1904225R8.1P Cell Line: LG3BP-AJ-1.2-14E09-02G07

IEF Parameters:

pI range of IEF gel: 3-10              IEF Gel Lot No: 6424025

IEF Standard (pI 4.45-9.6) Lot No: 6417547

Antibody quantity per well: 20 µg

Focusing Conditions:    100 volts, 1hr
                        250 volts, 1hr
                        500 volts, 30min Image of IEF Gel Lane 1: pI markers Lot# 6417547
Lane 2: LG3BP-AJ-1.2-14E09-02G07 Lot# 190223RB.1P Cell Line: LG3BP-AJ-1.2-14E09-02F04

IEF Parameters:

pI range of IEF gel: 3-10         IEF Gel Lot No: 64244025

IEF Standard (pI 4.45-9.6) Lot No: 64174547

Antibody quantity per well: 20 μg

Focusing Conditions:    100 volts, 1hr
                        250 volts, 1hr
                        500 volts, 30min Lane 1: pI markers Lot# 64174547
Lane 2: LG3BP-AJ-1.2-14E09-02F04 Lot# 190321RB.1P Cell Line: LG3BP-AJ-1.2-14E09-02F08

IEF Parameters:

pI range of IEF gel: 3-10          IEF Gel Lot No: 64244025

IEF Standard (pI 4.45-9.6) Lot No: 64174547

Antibody quantity per well: 20 µg

Focusing Conditions:   100 volts, 1hr
                       250 volts, 1hr
                       500 volts, 30min Image of IEF Gel Lane 1: pI markers Lot# 64174547
Lane 2: LG3BP-AJ-1.2-14E09-02F08 Lot# 190322RB.1P Cell Line: C163A-BA-1.3-13G05-02E09

SDS-PAGE Parameters:

Percent Cross-linking of Polyacrylamide Gel: 4-20% Gradient    Gel Lot No: 6252191

Molecular Weight Standard: BioRad Kaleidoscope Precision Plus    Standard Lot No: 6237745

Antibody quantity per well: 5 μg

Image of SDS-PAGE Gel

<u>Non-Reduced</u>
Lane 1: MW Standard
Lot # 6237745
Lane 3: C163A-BA-
1.3-13G05-02E09
Lot # 1904224RB.1P <u>Reduced</u>
Lane 2: C163A-BA-1.3-
13G05-02E09
Lot # 1904224RB.1P Reduced

FIG. 3B

Cell Line: C163A-BA-1.3-13H05-02F02

SDS-PAGE Parameters:

Percent Cross-linking of Polyacrylamide Gel: 4-20% Gradient     Gel Lot No: 64252191

Molecular Weight Standard: BioRad Kaleidoscope Precision Plus     Standard Lot No: 64237745

Antibody quantity per well: 5 µg

Image of SDS-PAGE Gel

| MW Standard | 1 | 2 | 3 | | Non-Reduced | Reduced |
|---|---|---|---|---|---|---|
| 250kD | | | | | Lane 1: MW Standard Lot # 64237745 | Lane 2: C163A-BA-1.3-13H05-02F02 Lot # 1904225RB.IP |
| 150kD | | | — | | Lane 3: C163A-BA-1.3-13H05-02F02 Lot # 1904225RB.IP | |
| 100kD | — | | | | | |
| 75kD | — | | | | | |
| 50kD | — | — | | | | |
| 37kD | | — | | | | |
| 25kD | — | — | | | | |
| 20kD | — | | | | | |
| 15kD | — | | | | | |
| 10kD | — | | | | | |

Reduced

Cell Line: LG3BP-AJ-1.2-14E09-02G07

SDS-PAGE Parameters:

Percent Cross-linking of Polyacrylamide Gel: 4-20% Gradient          Gel Lot No: 64239169

Molecular Weight Standard: BioRad Kaleidoscope Precision Plus          Standard Lot No: 6409818

Antibody quantity per well: 5 µg

Non-Reduced
Lane 1: MW Standard
Lot# 6409818
Lane 2: LG3BP-AJ-1.2-14E09-02G07
Lot# 190323RB.IP Reduced
Lane 1: MW Standard
Lot# 6409818
Lane 3: LG3BP-AJ-1.2-14E09-02G07
Lot# 190323RB.IP Reduced

FIG. 4C

Cell Line: LG3BP-AJ-1.2-14E09-02F08

SDS-PAGE Parameters:

Percent Cross-linking of Polyacrylamide Gel: 4-20% Gradient        Gel Lot No: 6423916Q Molecular Weight Standard: BioRad Kaleidoscope Precision Plus      Standard Lot No: 64094818

Antibody quantity per well: 5 μg

Image of SDS-PAGE Gel

| MW Standard | 1 | 2 | 3 | Non-Reduced | Reduced |
|---|---|---|---|---|---|
| 250kD | | | | Lane 1: MW Standard | Lane : MW Standard |
| 150kD | | | | Lot# 64094818 | Lot# 64094818 |
| 100kD | | | | Lane 2: LG3BP-AJ- | Lane 3: LG3BP-AJ-1.2- |
| 75kD  | | | | 1.2-14E09-02F08 | 14E09-02F08 |
|       | | | | Lot# 193222RB.IP | Lot# 193222RB.IP |
| 50kD  | | | | | |
| 37kD  | | | | | |
| 25kD  | | | | | |
| 20kD  | | | | | |
| 15kD  | | | | | |
| 10kD  | | | | | |

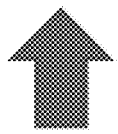

Reduced

SEQUENCE LISTING

<160> NUMBER OF SEQ ID NOS: 45

<210> SEQ ID NO 1
<211> LENGTH: 8

```
<212> TYPE: PRT
<213> ORGANISM: Mus musculus

<400> SEQUENCE: 1

Gly Phe Thr Phe Ser Ser Tyr Ala
1               5

<210> SEQ ID NO 2
<211> LENGTH: 8
<212> TYPE: PRT
<213> ORGANISM: Mus musculus

<400> SEQUENCE: 2

Ile Ser Ser Ser Gly Ser Tyr Thr
1               5

<210> SEQ ID NO 3
<211> LENGTH: 11
<212> TYPE: PRT
<213> ORGANISM: Mus musculus

<400> SEQUENCE: 3

Ala Arg Gln Glu Gly Leu Trp Ser Phe Ala Tyr
1               5                   10

<210> SEQ ID NO 4
<211> LENGTH: 11
<212> TYPE: PRT
<213> ORGANISM: Mus musculus

<400> SEQUENCE: 4

Gln Ser Leu Leu Asp Ser Asp Gly Lys Thr Tyr
1               5                   10

<210> SEQ ID NO 5
<211> LENGTH: 3
<212> TYPE: PRT
<213> ORGANISM: Mus musculus

<400> SEQUENCE: 5

Leu Val Ser
1

<210> SEQ ID NO 6
<211> LENGTH: 9
<212> TYPE: PRT
<213> ORGANISM: Mus musculus

<400> SEQUENCE: 6

Trp Gln Gly Thr His Phe Pro Trp Thr
1               5

<210> SEQ ID NO 7
<211> LENGTH: 8
<212> TYPE: PRT
<213> ORGANISM: Mus musculus

<400> SEQUENCE: 7

Gly Tyr Thr Phe Ser Ser Tyr Trp
1               5

<210> SEQ ID NO 8
<211> LENGTH: 8
<212> TYPE: PRT
<213> ORGANISM: Mus musculus
```

```
<400> SEQUENCE: 8

Ile Asn Arg Ser Asn Gly Arg Thr
1               5

<210> SEQ ID NO 9
<211> LENGTH: 9
<212> TYPE: PRT
<213> ORGANISM: Mus musculus

<400> SEQUENCE: 9

Thr Lys Trp Gly Val Thr Ser Asp Tyr
1               5

<210> SEQ ID NO 10
<211> LENGTH: 5
<212> TYPE: PRT
<213> ORGANISM: Mus musculus

<400> SEQUENCE: 10

Ser Asn Val Asn Tyr
1               5

<210> SEQ ID NO 11
<211> LENGTH: 3
<212> TYPE: PRT
<213> ORGANISM: Mus musculus

<400> SEQUENCE: 11

Asp Thr Ser
1

<210> SEQ ID NO 12
<211> LENGTH: 9
<212> TYPE: PRT
<213> ORGANISM: Mus musculus

<400> SEQUENCE: 12

Phe Gln Gly Ser Gly Tyr Pro Arg Thr
1               5

<210> SEQ ID NO 13
<211> LENGTH: 118
<212> TYPE: PRT
<213> ORGANISM: Mus musculus

<400> SEQUENCE: 13

Glu Val Met Leu Val Glu Ser Gly Gly Gly Leu Val Lys Pro Gly Ser
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Val Ile Ser Ser Ser Gly Ser Tyr Thr Phe Tyr Thr Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Glu Gly Leu Trp Ser Phe Ala Tyr Trp Gly Gln Gly Thr
            100                 105                 110
```

Leu Val Thr Val Ser Ala
        115

<210> SEQ ID NO 14
<211> LENGTH: 112
<212> TYPE: PRT
<213> ORGANISM: Mus musculus

<400> SEQUENCE: 14

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

<210> SEQ ID NO 15
<211> LENGTH: 116
<212> TYPE: PRT
<213> ORGANISM: Mus musculus

<400> SEQUENCE: 15

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
        35                  40                  45

Gly Glu Ile Asn Arg Ser Asn Gly Arg Thr Asn Tyr Asn Glu Lys Phe
    50                  55                  60

Lys Ser Lys Ala Thr Leu Thr Val Asp Lys Ser Ser Thr Thr Ala Tyr
65                  70                  75                  80

Met Gln Leu Ser Ser Leu Thr Ser Glu Asp Ser Ala Val Tyr Tyr Cys
                85                  90                  95

Thr Lys Trp Gly Val Thr Ser Asp Tyr Trp Gly Gln Gly Thr Thr Leu
            100                 105                 110

Thr Val Ser Ser
        115

<210> SEQ ID NO 16
<211> LENGTH: 106
<212> TYPE: PRT
<213> ORGANISM: Mus musculus

<400> SEQUENCE: 16

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Asn Val Asn Tyr Met
            20                  25                  30

His Trp Phe Gln Gln Lys Ser Ser Thr Ser Pro Lys Leu Trp Ile Tyr

```
                35                  40                  45
Asp Thr Ser Lys Leu Ala Ser Gly Val Pro Gly Arg Phe Ser Gly Ser
            50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Arg Thr
                85                  90                  95

Phe Gly Gly Gly Thr Lys Leu Glu Ile Lys
            100                 105

<210> SEQ ID NO 17
<211> LENGTH: 354
<212> TYPE: DNA
<213> ORGANISM: Mus musculus

<400> SEQUENCE: 17
gaagtgatgc tggtggagtc tgggggaggc ttagtgaagc ctggaagttc cctgaaactc      60
tcctgtgcag cctctggatt cactttcagt agctatgcca tgtcttgggt tcgccagact     120
ccggagaaga ggctggaatg ggtcgcagtc attagtagta gtggaagtta ccacttctat     180
acagacagtg tgaaggggcg attcaccatc tccagagaca atgccaagaa caccctgtac     240
ctgcaaatga gcagtctgag gtctgaagac acggccatgt attactgtgc aagacaggag     300
gggttatggt cgtttgctta ctggggccaa gggactctgg tcactgtctc tgca           354

<210> SEQ ID NO 18
<211> LENGTH: 336
<212> TYPE: DNA
<213> ORGANISM: Mus musculus

<400> SEQUENCE: 18
gatgttgtgc tgacccagac tccactcact ttgtcggtta ccattggaca accagcctcc      60
atctcttgca gtcaagtca gagcctctta gatagtgatg aaagacata tttgaattgg       120 ttgttacaga ggccaggcca gtctccaaag cgcctaatct atctggtgtc taaactggac     180
tctggagtcc ctgacaggtt cactggcagt ggatcaggga cagatttcac actgaaaatc     240
agcagagtgg aggctgagga tttgggagtt tattattgct ggcaaggtac acattttccg     300
tggacgttcg gtggaggcac caagctggaa atcaaa                               336

<210> SEQ ID NO 19
<211> LENGTH: 348
<212> TYPE: DNA
<213> ORGANISM: Mus musculus

<400> SEQUENCE: 19
caggtccaac tgcagcagcc tggggctgaa ctggtgaagc ctggggcttc agtgaagctg      60
tcctgcaagg cttctggcta caccttcagc agctactgga tgcactgggt gaagcagagg     120
cctggacaag gccttgagtg gattggagag attaatcgta gcaacggtcg actaactac      180 aatgagaagt tcaagagcaa ggccacactg actgtagaca atcctccac cacagcctac      240 atgcaactca gcagcctgac atctgaggac tctgcggtct attactgtac aaaatggggt     300
gtgacgagtg actactgggg ccaaggcacc actctcacag tctcctca                  348

<210> SEQ ID NO 20
<211> LENGTH: 318
<212> TYPE: DNA
<213> ORGANISM: Mus musculus
```

<400> SEQUENCE: 20

```
gaaaatgttc tcacccagtc tccagcaatc atgtctgcat ctccagggga aaaggtcacc    60
atgacctgca gtgccagctc aaatgtaaat tacatgcact ggttccagca gaagtctagc   120
acctccccca aactctggat ttatgacaca tccaaactgg cttctggagt cccaggtcgc   180
ttcagtggca gtgggtctgg aaactcttac tctctcacga tcagcagcat ggaggctgaa   240
gatgttgcca cttattactg ttttcagggg agtggatacc cacgtacgtt cggagggggg   300
accaagctgg aaataaaa                                                 318
```

<210> SEQ ID NO 21
<211> LENGTH: 16
<212> TYPE: PRT
<213> ORGANISM: Artificial Sequence
<220> FEATURE:
<223> OTHER INFORMATION: synthetic

<400> SEQUENCE: 21

```
Glu Leu Ser Glu Ala Leu Gly Gln Ile Phe Asp Ser Gln Arg Gly Cys
1               5                   10                  15
```

<210> SEQ ID NO 22
<211> LENGTH: 14
<212> TYPE: PRT
<213> ORGANISM: Artificial Sequence
<220> FEATURE:
<223> OTHER INFORMATION: synthetic

<400> SEQUENCE: 22

```
Glu Leu Ser Glu Ala Leu Gly Gln Ile Phe Asp Ser Gln Arg
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: synthetic

<400> SEQUENCE: 23

```
Cys Gly His Thr Val Ile Leu Thr Ala Asn Leu Glu
1               5                   10
```

<210> SEQ ID NO 24
<211> LENGTH: 36
<212> TYPE: PRT
<213> ORGANISM: Artificial Sequence
<220> FEATURE:
<223> OTHER INFORMATION: synthetic

<400> SEQUENCE: 24

```
Gly Cys Asp Leu Ser Ile Ser Val Asn Val Gln Gly Glu Asp Ala Leu
1               5                   10                  15

Gly Phe Cys Gly His Thr Val Ile Leu Thr Ala Asn Leu Glu Ala Gln
            20                  25                  30

Ala Leu Trp Lys
        35
```

<210> SEQ ID NO 25
<211> LENGTH: 11
<212> TYPE: PRT
<213> ORGANISM: Artificial Sequence
<220> FEATURE:

<223> OTHER INFORMATION: synthetic

<400> SEQUENCE: 25

Thr Gln Ala Glu Ala Trp Pro Ser Val Pro Thr
1               5                   10

<210> SEQ ID NO 26
<211> LENGTH: 33
<212> TYPE: PRT
<213> ORGANISM: Artificial Sequence
<220> FEATURE:
<223> OTHER INFORMATION: synthetic

<400> SEQUENCE: 26

Leu Cys Leu Gln Phe Leu Ala Trp Asn Phe Glu Ala Leu Thr Gln Ala
1               5                   10                  15

Glu Ala Trp Pro Ser Val Pro Thr Asp Leu Leu Gln Leu Leu Leu Pro
            20                  25                  30

Arg

<210> SEQ ID NO 27
<211> LENGTH: 12
<212> TYPE: PRT
<213> ORGANISM: Artificial Sequence
<220> FEATURE:
<223> OTHER INFORMATION: synthetic

<400> SEQUENCE: 27

Ala Ser His Glu Glu Val Glu Gly Leu Val Glu Lys
1               5                   10

<210> SEQ ID NO 28
<211> LENGTH: 14
<212> TYPE: PRT
<213> ORGANISM: Artificial Sequence
<220> FEATURE:
<223> OTHER INFORMATION: synthetic

<400> SEQUENCE: 28

Tyr Tyr Pro Tyr Gln Ser Phe Gln Thr Pro Gln His Pro Ser
1               5                   10

<210> SEQ ID NO 29
<211> LENGTH: 20
<212> TYPE: PRT
<213> ORGANISM: Artificial Sequence
<220> FEATURE:
<223> OTHER INFORMATION: synthetic

<400> SEQUENCE: 29

Tyr Tyr Pro Tyr Gln Ser Phe Gln Thr Pro Gln His Pro Ser Phe Leu
1               5                   10                  15

Phe Gln Asp Lys
            20

<210> SEQ ID NO 30
<211> LENGTH: 8
<212> TYPE: PRT
<213> ORGANISM: Artificial Sequence
<220> FEATURE:
<223> OTHER INFORMATION: synthetic

<400> SEQUENCE: 30

Leu Val Asp Gly Val Thr Glu Cys
1               5

```
<210> SEQ ID NO 31
<211> LENGTH: 11
<212> TYPE: PRT
<213> ORGANISM: Artificial Sequence
<220> FEATURE:
<223> OTHER INFORMATION: synthetic

<400> SEQUENCE: 31

Leu Val Asp Gly Val Thr Glu Cys Ser Gly Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic

<400> SEQUENCE: 32

Cys Ala Gly Thr Val Glu Val Glu Ile Gln Arg
1               5                   10

<210> SEQ ID NO 33
<211> LENGTH: 15
<212> TYPE: PRT
<213> ORGANISM: Artificial Sequence
<220> FEATURE:
<223> OTHER INFORMATION: synthetic

<400> SEQUENCE: 33

Cys Ala Gly Thr Val Glu Val Glu Ile Gln Arg Leu Leu Gly Lys
1               5                   10                  15

<210> SEQ ID NO 34
<211> LENGTH: 8
<212> TYPE: PRT
<213> ORGANISM: Artificial Sequence
<220> FEATURE:
<223> OTHER INFORMATION: synthetic

<400> SEQUENCE: 34

Thr Ser Tyr Gln Val Tyr Ser Lys
1               5

<210> SEQ ID NO 35
<211> LENGTH: 10
<212> TYPE: PRT
<213> ORGANISM: Artificial Sequence
<220> FEATURE:
<223> OTHER INFORMATION: synthetic

<400> SEQUENCE: 35

Asn Gly Asn Glu Thr Ser Leu Trp Asp Cys
1               5                   10

<210> SEQ ID NO 36
<211> LENGTH: 24
<212> TYPE: PRT
<213> ORGANISM: Artificial Sequence
<220> FEATURE:
<223> OTHER INFORMATION: synthetic

<400> SEQUENCE: 36

Ile Gln Ala Thr Asn Thr Trp Leu Phe Leu Ser Ser Cys Asn Gly Asn
1               5                   10                  15
```

```
Glu Thr Ser Leu Trp Asp Cys Lys
            20
```

<210> SEQ ID NO 37
<211> LENGTH: 12
<212> TYPE: PRT
<213> ORGANISM: Artificial Sequence
<220> FEATURE:
<223> OTHER INFORMATION: synthetic

<400> SEQUENCE: 37

```
Cys Gly Val Ala Leu Ser Thr Pro Gly Gly Ala Arg
1               5                   10
```

<210> SEQ ID NO 38
<211> LENGTH: 9
<212> TYPE: PRT
<213> ORGANISM: Artificial Sequence
<220> FEATURE:
<223> OTHER INFORMATION: synthetic

<400> SEQUENCE: 38

```
Gly Asn Glu Ser Ser Leu Trp Asp Cys
1               5
```

<210> SEQ ID NO 39
<211> LENGTH: 12
<212> TYPE: PRT
<213> ORGANISM: Artificial Sequence
<220> FEATURE:
<223> OTHER INFORMATION: synthetic

<400> SEQUENCE: 39

```
Gly Asn Glu Ser Ser Leu Trp Asp Cys Pro Ala Arg
1               5                   10
```

<210> SEQ ID NO 40
<211> LENGTH: 9
<212> TYPE: PRT
<213> ORGANISM: Artificial Sequence
<220> FEATURE:
<223> OTHER INFORMATION: synthetic

<400> SEQUENCE: 40

```
Ser Thr His Thr Leu Asp Leu Ser Arg
1               5
```

<210> SEQ ID NO 41
<211> LENGTH: 6
<212> TYPE: PRT
<213> ORGANISM: Artificial Sequence
<220> FEATURE:
<223> OTHER INFORMATION: synthetic

<400> SEQUENCE: 41

```
Val Glu Ile Phe Tyr Arg
1               5
```

<210> SEQ ID NO 42
<211> LENGTH: 11
<212> TYPE: PRT
<213> ORGANISM: Artificial Sequence
<220> FEATURE:
<223> OTHER INFORMATION: synthetic

<400> SEQUENCE: 42

```
Gly Glu Asn Leu Val His Gln Ile Gln Tyr Arg
```

```
1               5              10

<210> SEQ ID NO 43
<211> LENGTH: 8
<212> TYPE: PRT
<213> ORGANISM: Artificial Sequence
<220> FEATURE:
<223> OTHER INFORMATION: synthetic

<400> SEQUENCE: 43

Thr Ser Tyr Gln Val Tyr Ser Lys
1               5

<210> SEQ ID NO 44
<211> LENGTH: 8
<212> TYPE: PRT
<213> ORGANISM: Artificial Sequence
<220> FEATURE:
<223> OTHER INFORMATION: synthetic

<400> SEQUENCE: 44

Ile Asn Pro Ala Ser Leu Asp Lys
1               5

<210> SEQ ID NO 45
<211> LENGTH: 14
<212> TYPE: PRT
<213> ORGANISM: Artificial Sequence
<220> FEATURE:
<223> OTHER INFORMATION: synthetic

<400> SEQUENCE: 45

Leu Glu Val Phe Tyr Asn Gly Ala Trp Gly Thr Val Gly Lys
1               5              10
```

ANTIBODIES TARGETING PULMONARY NODULE SPECIFIC BIOMARKERS AND USES THEREOF

REFERENCE TO SEQUENCE LISTING

Incorporated herein by reference in its entirety is a Sequence Listing entitled Sequence_Listing_BDR-02101_ST25.txt, comprising SEQ ID NO: 1 through SEQ ID NO: 45, which includes the nucleic acid and amino acid sequences disclosed herein. The Sequence Listing has been submitted electronically herewith in ASCII text format via EFS. The Sequence Listing was first created on Jan. 10, 2022 and is 13,805 bytes in size.

BACKGROUND

Lung conditions and particularly lung cancer present significant diagnostic challenges. In many asymptomatic patients, radiological screens such as computed tomography (CT) scanning are a first step in the diagnostic paradigm. Pulmonary nodules (PNs) or indeterminate nodules are located in the lung and are often discovered during screening of both high-risk patients or incidentally. The number of PNs identified is expected to rise due to increased numbers of patients with access to health care, the rapid adoption of screening techniques, an aging population, and the COVID-19 pandemic having led to more imaging of the pulmonary region. It is estimated that over 3 million PNs are identified annually in the US. Although the majority of PNs are benign, some are malignant leading to additional interventions. For patients considered low risk for malignant nodules, current medical practice dictates scans every three to six months for at least two years to monitor for lung cancer. The time period between identification of a PN and diagnosis is a time of medical surveillance or "watchful waiting" and may induce stress on the patient and lead to significant risk and expense due to repeated imaging studies. If a biopsy is performed on a patient who is found to have a benign nodule, the costs and potential for harm to the patient increase unnecessarily. Major surgery is indicated in order to excise a specimen for tissue biopsy and diagnosis. All of these procedures are associated with risk to the patient including: illness, injury and death as well as high economic costs.

Frequently, PNs cannot be biopsied to determine if they are benign or malignant due to their size and/or location in the lung. However, PNs are connected to the circulatory system, and so if malignant, protein markers of cancer can enter the blood and provide a signal for determining if a PN is malignant or not.

Diagnostic methods that can replace or complement current diagnostic methods in the standard of care, for patients presenting with PNs are needed to improve disease diagnosis, classification, potentially reduce costs associated with surgical intervention and hospitalization, and to minimize complications to patients.

BRIEF DESCRIPTION OF THE DRAWINGS

FIGS. 3A and 3B show SDS-PAGE data for C163A INPA clones.
FIGS. 4A-4C show SDS-PAGE data for LG3BP VEYFIR clones.

Figure 1A:
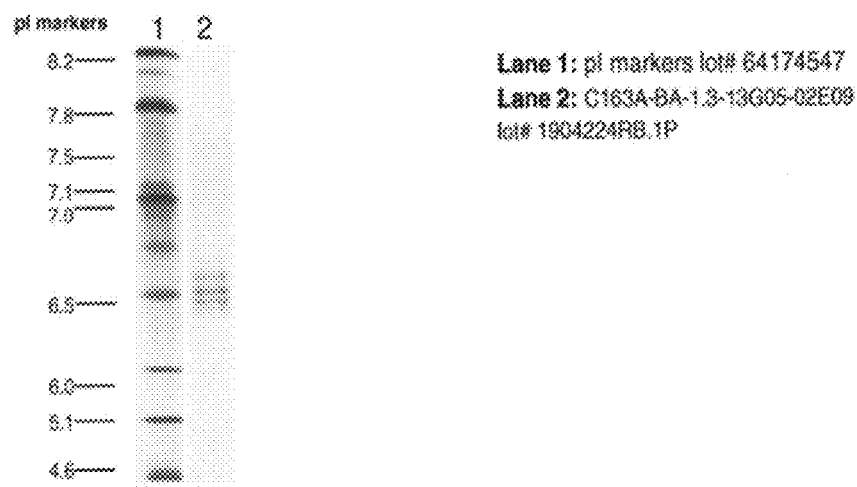
FIGS. 1A and 1B show IEF data for C163A INPA clones.

For any figure showing a bar histogram, curve, or other data associated with a legend, the bars, curve, or other data presented from left to right for each indication correspond directly and in order to the boxes from top to bottom of the legend.

DETAILED DESCRIPTION

Described herein are isolated antibodies, particularly monoclonal antibodies, e.g., human monoclonal antibodies, or antigen binding fragments thereof, which specifically bind to C163A or LG3BP.

Accordingly, provided herein are methods of making such antibodies, nucleic acids or vectors encoding such antibodies, and pharmaceutical compositions formulated to contain such antibodies. Also provided herein are diagnostic, prognostic, and therapeutic methods of using such antibodies, and devices employing such antibodies and/or fragments.

SUMMARY

Provided herein are antibodies, such as monoclonal antibodies, that specifically bind defined peptides in C163A or LG3BP. In some aspects, provided here are methods and kits using these antibodies to identify, diagnose, classify, prognose, and monitor lung conditions, and particularly the likelihood of a lung nodule being benign. In some aspects, provided here are methods and kits using these antibodies to assess or monitor effects of a therapeutic treatment or reagent for lung conditions such as lung cancer.

In some aspects, provided here are monoclonal antibodies, or antigen-binding fragments thereof, wherein the monoclonal antibodies or antigen-binding fragments thereof comprise: a) a heavy chain CDR sequence with at least about 85% identity to a heavy chain CDR sequence selected from the group consisting of the heavy chain CDR sequences listed in Table 1A; and/or b) a light chain CDR sequence with at least about 85% identity to a light chain CDR sequence selected from the group consisting of the light chain CDR sequences listed in Table 1A.

In some aspects, provided here are monoclonal antibodies, or antigen-binding fragments thereof, wherein the monoclonal antibodies or antigen-binding fragments thereof comprise: a) a heavy chain CDR sequence selected from the group consisting of the heavy chain CDR sequences listed in Table 1A; and/or b) a light chain CDR sequence selected from the group consisting of the light chain CDR sequences listed in Table 1A.

In some aspects, provided here are monoclonal antibodies, or antigen-binding fragments thereof, wherein the monoclonal antibodies or antigen-binding fragments thereof comprise: a) a combination of a heavy chain CDR1, CDR2, and CDR3 as set forth in any one heavy chain row of Table 1A; and/or b) a combination of a light chain CDR1, CDR2, and CDR3 as set forth in any one light chain row of Table 1A.

In some embodiments, the light chain CDR(s) in b) belongs to the same laboratory designated antibody as the heavy chain CDR(s) in a).

In some aspects, provided here are monoclonal antibodies, or antigen-binding fragments thereof, wherein the monoclonal antibody or antigen-binding fragments thereof comprise: a) a heavy chain variable domain (VH) sequence with at least about 85% identity to a VH sequence selected from the group consisting of the VH sequences listed in Table 2A; and/or b) a light chain variable domain (VL)

sequence with at least about 85% identity to a VL sequence selected from the group consisting of the VL sequences listed in Table 2A.

In some aspects, provided here are monoclonal antibodies, or antigen-binding fragments thereof, wherein the monoclonal antibody or antigen-binding fragments thereof comprise: a) a VH sequence selected from the group consisting of the VH sequences listed in Table 2A; and/or b) a VL sequence selected from the group consisting of the VL sequences listed in Table 2A.

In some embodiments, the VL in b) belongs to the same laboratory designated antibody as the VH in a).

In some embodiments, the monoclonal antibody or antigen-binding fragment thereof comprises: (1) a heavy chain CDR1 (HC-CDR1) set forth in GFTFSSYA (SEQ ID NO: 1), a heavy chain CDR2 (HC-CDR2) set forth in ISSSGSYT (SEQ ID NO: 2), a heavy chain CDR3 (HC-CDR3) set forth in ARQEGLWSFAY(SEQ ID NO: 3), a light chain CDR1 (LC-CDR1) set forth in QSLLDSDGKTY(SEQ ID NO: 4), a light chain CDR2 (LC-CDR2) set forth in LVS(SEQ ID NO: 5), and a light chain CDR3 (LC-CDR3) set forth in WQGTHFPWT(SEQ ID NO: 6); or (2) a HC-CDR1 set forth in GFTFSSYA(SEQ ID NO: 1), a HC-CDR2 set forth in ISSSGSYT(SEQ ID NO: 2), a HC-CDR3 set forth in ARQEGLWSFAY(SEQ ID NO: 3), a LC-CDR1 set forth in QSLLDSDGKTY(SEQ ID NO: 4), a LC-CDR2 set forth in LVS(SEQ ID NO: 5), and a LC-CDR3 set forth in WQGTHFPWT(SEQ ID NO: 6).

In some embodiments, the monoclonal antibody, or antigen-binding fragment thereof, described herein specifically binds to a peptide or protein comprising a sequence set forth in INPA. In some embodiments, the monoclonal antibody, or antigen-binding fragment thereof, described herein specifically binds to C163A.

In some aspects, provided here are monoclonal antibodies, or antigen-binding fragments thereof, wherein the monoclonal antibody or antigen-binding fragments thereof comprise: a) a heavy chain CDR sequence with at least about 85% identity to a heavy chain CDR sequence selected from the group consisting of the heavy chain CDR sequences listed in Table 1B; and/or b) a light chain CDR sequence with at least about 85% identity to a light chain CDR sequence selected from the group consisting of the light chain CDR sequences listed in Table 1B.

In some aspects, provided here are monoclonal antibodies, or antigen-binding fragments thereof, wherein the monoclonal antibody or antigen-binding fragments thereof comprise: a) a heavy chain CDR sequence selected from the group consisting of the heavy chain CDR sequences listed in Table 1B; and/or b) a light chain CDR sequence selected from the group consisting of the light chain CDR sequences listed in Table 1B.

In some aspects, provided here are monoclonal antibodies, or antigen-binding fragments thereof, wherein the monoclonal antibody or antigen-binding fragments thereof comprise: a) a combination of a heavy chain CDR1, CDR2, and CDR3 as set forth in any one heavy chain row of Table 1B; and/or b) a combination of a light chain CDR1, CDR2, and CDR3 as set forth in any one light chain row of Table 1B.

In some embodiments, the light chain CDR(s) in b) belongs to the same laboratory designated antibody as the heavy chain CDR(s) in a).

In some aspects, provided here are monoclonal antibodies, or antigen-binding fragments thereof, wherein the monoclonal antibody or antigen-binding fragments thereof comprise: a) a heavy chain variable domain (VH) sequence with at least about 85% identity to a VH sequence selected from the group consisting of the VH sequences listed in Table 2B; and/or b) a light chain variable domain (VL) sequence with at least about 85% identity to a VL sequence selected from the group consisting of the VL sequences listed in Table 2B.

In some aspects, provided here are monoclonal antibodies, or antigen-binding fragments thereof, wherein the monoclonal antibody or antigen-binding fragments thereof comprise: a) a VH sequence selected from the group consisting of the VH sequences listed in Table 2B; and/or b) a VL sequence selected from the group consisting of the VL sequences listed in Table 2B.

In some embodiments, the VL in b) belongs to the same laboratory designated antibody as the VH in a).

In some embodiments, the monoclonal antibody or antigen-binding fragment thereof comprises: (1) a HC-CDR1 set forth in GYTFSSYW(SEQ ID NO: 7), a HC-CDR2 set forth in INRSNGRT(SEQ ID NO: 8), a HC-CDR3 set forth in TKWGVTSDY(SEQ ID NO: 9), a LC-CDR1 set forth in SNVNY(SEQ ID NO: 10), a LC-CDR2 set forth in DTS (SEQ ID NO: 11), and a LC-CDR3 set forth in FQGSGYPRT(SEQ ID NO: 12); (2) a HC-CDR1 set forth in GYTFSSYW(SEQ ID NO: 7), a HC-CDR2 set forth in INRSNGRT(SEQ ID NO: 8), a HC-CDR3 set forth in TKWGVTSDY(SEQ ID NO: 9), a LC-CDR1 set forth in SNVNY(SEQ ID NO: 10), a LC-CDR2 set forth in DTS (SEQ ID NO: 11), and a LC-CDR3 set forth in FQGSGYPRT(SEQ ID NO: 12); or (3) a HC-CDR1 set forth in GYTFSSYW(SEQ ID NO: 7), a HC-CDR2 set forth in INRSNGRT(SEQ ID NO: 8), a HC-CDR3 set forth in TKWGVTSDY(SEQ ID NO: 9), a LC-CDR1 set forth in SNVNY(SEQ ID NO: 10), a LC-CDR2 set forth in DTS (SEQ ID NO: 11), and a LC-CDR3 set forth in FQGSGYPRT(SEQ ID NO: 12).

In some embodiments, the monoclonal antibody, or antigen-binding fragment thereof, specifically binds to a peptide or protein comprising a sequence set forth in VEIFYR(SEQ ID NO: 41). In some embodiments, the monoclonal antibody, or antigen-binding fragment thereof, specifically binds to LG3BP.

In some embodiments, the monoclonal antibody, or antigen-binding fragment thereof, is chimeric, humanized, composite, murine, or human. In some embodiments, the monoclonal antibody, or antigen-binding fragment thereof, is detectably labeled, comprises an effector domain, comprises an Fc domain, and/or is selected from the group consisting of Fv, Fav, F(ab')2), Fab', dsFv, scFv, scFv)2, and diabodies fragments. In some embodiments, the monoclonal antibody, or antigen-binding fragment thereof, is an Immunoglobulin G type antibody.

In some aspects, provided herein are isolated nucleic acid molecules encoding the monoclonal antibodies, or antigen-binding fragments thereof, described herein.

In some aspects, provided herein are vectors comprising the isolated nucleic acids described herein.

In some embodiments, the vector is a cloning vector, an expression vector, or a viral vector.

In some aspects, provided herein is a host cell which comprises the isolated nucleic acid described herein, comprises the vector described herein, and/or expresses the monoclonal antibody, or antigen-binding fragment thereof, described herein.

In some aspects, provided herein is a device or kit comprising at least one monoclonal antibody, or antigen-binding fragment thereof, described herein, said device or kit optionally comprising a label to detect the at least one monoclonal antibody, or antigen-binding fragment thereof, or a complex comprising the monoclonal antibody, or antigen-binding fragment thereof.

In some aspects, provided herein is a pharmaceutical composition comprising at least one monoclonal antibody, or antigen-binding fragment thereof, described herein, and a pharmaceutically acceptable carrier.

In some aspects, provided herein is a method of producing at least one monoclonal antibody, or antigen-binding fragment thereof, described herein, which method comprises the steps of: (i) culturing a transformed host cell which has been transformed by a nucleic acid comprising a sequence encoding at least one monoclonal antibody described herein under conditions suitable to allow expression of said monoclonal antibody, or antigen-binding fragment thereof; and (ii) recovering the expressed monoclonal antibody, or antigen-binding fragment thereof.

In some aspects, provided herein is a method of detecting the presence or level of C163A or a fragment of C163A comprising INPA sequence in a sample comprising using at least one monoclonal antibody, or antigen-binding fragment thereof, described herein.

In some embodiments, the at least one monoclonal antibody, or antigen-binding fragment thereof, forms a complex with C163A or a fragment of C163A comprising INPA sequence and the complex is detected in the form of an enzyme linked immunosorbent assay (ELISA), radioimmune assay (RIA), immunohistochemically, immunoprecipitation, Western blot, or using an intracellular flow assay, or combinations of these assays.

In some aspects, provided herein is a method of detecting the presence or level of LG3BP or a fragment of LG3BP comprising VEIFYR (SEQ ID NO: 41) sequence in a sample comprising using at least one monoclonal antibody, or antigen-binding fragment thereof, described herein.

In some embodiments, the at least one monoclonal antibody, or antigen-binding fragment thereof, forms a complex with LG3BP or a fragment of LG3BP comprising VEIFYR (SEQ ID NO: 41) sequence and the complex is detected in the form of an enzyme linked immunosorbent assay (ELISA), radioimmune assay (RIA), immunohistochemically, immunoprecipitation, Western blot, or using an intracellular flow assay, or combinations of these assays. In some embodiments, the sample is a biological sample obtained from a subject. In some embodiments, the subject has a pulmonary nodule or is at risk of having lung cancer.

In some aspects, provided herein is a method of detecting the presence of lung cancer in a subject comprising detecting the level of a group of proteins comprising C163A and LG3BP in a subject sample by use of (1) at least one monoclonal antibody, or antigen-binding fragment thereof, described herein, and (2) at least one monoclonal antibody, or antigen-binding fragment thereof, described herein.

In some embodiments, the method further comprises obtaining the sample from the subject. In some embodiments, the subject has a pulmonary nodule or is at risk of having lung cancer. In some embodiments, the at least one monoclonal antibody, or antigen-binding fragment thereof, forms a complex with C163A or LG3BP and the complex is detected in the form of an enzyme linked immunosorbent assay (ELISA), radioimmune assay (RIA), immunohistochemically, immunoprecipitation, Western blot, or using an intracellular flow assay, or combinations of these assays.

In some aspects, provided herein is a method for monitoring the progression of lung cancer in a subject, the method comprising: a) detecting in a subject's sample at a first point in time the level of a group of proteins comprising C163A and LG3BP using (1) at least one monoclonal antibody, or antigen-binding fragment thereof, described herein, and (2) at least one monoclonal antibody, or antigen-binding fragment thereof, described herein; b) repeating step a) at a subsequent point in time; and c) comparing the level of the group of proteins comprising C163A and LG3BP detected in steps a) and b) to monitor the progression of lung cancer in the subject.

In some embodiments, between the first point in time and the subsequent point in time, the subject has undergone treatment to alleviate the lung cancer.

In some aspects, provided herein is a method of assessing the efficacy of a therapy for lung cancer in a subject, the method comprising: a) determining the level of a group of proteins comprising C163A and LG3BP using (1) at least one monoclonal antibody, or antigen-binding fragment thereof, described herein and (2) at least one monoclonal antibody, or antigen-binding fragment thereof, described herein, in a first sample obtained from the subject prior to providing at least a portion of the therapy to the subject, and b) determining the level of the group of proteins comprising C163A and LG3BP in a second sample obtained from the subject following provision of the portion of the therapy, wherein a significantly lower level of the group of proteins comprising C163A and LG3BP in the second sample, relative to the first sample, is an indication that the therapy is efficacious for treating lung cancer in the subject.

In some embodiments, the first and second samples are portions of a single sample obtained from the subject or portions of pooled samples obtained from the subject. In some embodiments, the sample comprises cells, serum, plasma, body fluid, nasal swab, and/or lung tissue obtained from the subject. In some embodiments, said significantly lower level of the group of proteins comprising C163A and LG3BP comprises a twenty percent or more decrease of the level of the group of proteins comprising C163A and LG3BP. In some embodiments, the group of proteins consists of C163A and LG3BP. In some embodiments, the subject is a mammal. In some embodiments, the mammal is a humanized mouse or a human. In some embodiments, the mammal is a human.

In some aspects, provided herein is a method of determining the likelihood that a pulmonary nodule in a subject is not lung cancer, comprising: (a) measuring the expression levels of a panel of proteins present in a blood sample obtained from the subject, wherein the panel of proteins comprises LG3BP and C163A; (b) calculating a probability of lung cancer score based on the expression levels of the panel of proteins of step (a); and (c) ruling out lung cancer for the subject if the score in step (b) is lower than a pre-determined score; and wherein the step (a) comprising contacting the blood sample with a LG3BP antibody described herein and a C163A antibody described herein.

In some embodiments, the expression levels of the panel of proteins are measured by an immunoassay. In some embodiments, the immunoassay is enzyme-linked immunosorbent assay (ELISA). In some embodiments, the panel of proteins further comprises at least one of ALDOA, FRIL, TSP1, COIA1, PEDF, MASP1, GELS, LUM, PTPRJ, IBP3, LRP1, ISLR, GRP78, TETN, PRDX1, CD14, BGH3, FIBA, and GSLG1. In some embodiments, when lung cancer is ruled out, or a nodule is prognosed to be benign, the subject does not receive a therapeutic intervention treatment protocol. In some embodiments, the treatment protocol is a pulmonary function test (PFT), pulmonary imaging, a biopsy, a surgery, a chemotherapy, a radiotherapy, or any combination thereof. In some embodiments, the pulmonary imaging is an x-ray, a chest computed tomography (CT) scan, or a positron emission tomography (PET) scan. In some embodiments, the pulmonary nodule has a diameter of less than or equal to 3 cm. In some embodiments, the pulmonary nodule has a diameter of about 0.8 cm to 3.0 cm. In some embodiments, the subject is at risk of developing lung cancer. In some embodiments, the subject is 40 years or older.

In some aspects, provided herein is a method of determining the likelihood that a pulmonary nodule in a subject is not lung cancer, comprising: (a) contacting a blood sample obtained from the subject with a proteolytic enzyme to produce peptide fragments from a panel of proteins present in the blood sample, wherein the panel comprises C163A and LG3BP; (b) selecting the produced peptide fragments from the panel from step (a) with labeled, synthetic peptide fragments which correspond to the produced peptide fragments from the panel; (c) performing selected reaction monitoring mass spectrometry to measure the abundance of the peptide fragments from step (b); (d) calculating a probability of lung cancer score based on the peptide fragment measurements of step (c); and (e) ruling out lung cancer for the subject if the score in step (d) is lower than a pre-determined score, and wherein the selected reaction monitoring mass spectrometry is performed using a LG3BP antibody described herein and a C163A antibody described herein.

In some embodiments, when lung cancer is ruled out, or a nodule is prognosed to be benign, the subject is monitored periodically. In some embodiments, the subject has low to moderate cancer risk. In some embodiments, the methods provided herein further comprise a physician's assessment of cancer risk. In some embodiments, the subject is assigned a physician's assessment of cancer risk from between 0 to 1. In some embodiments, the cancer risk is determined by a cancer risk predictor $Ci(k)$ determined as $$Ci(k) = \begin{cases} 0, & \text{if } pCA(k) \le Ti \\ pCA(k), & \text{otherwise} \end{cases}$$

wherein the decision threshold $Ti$ is the median value of $\{Si(k)\}$ of patients with nodules no larger than 15 mm.

In some embodiments, the periodic monitoring is a pulmonary function test (PFT), pulmonary imaging, a biopsy or any combination thereof. In some embodiments, said pulmonary imaging is an x-ray, a chest computed tomography (CT) scan, or a positron emission tomography (PET) scan. In some embodiments, said pulmonary nodule has a diameter of less than or equal to 3 cm. In some embodiments, said pulmonary nodule has a diameter of about 0.8 cm up to 3.0 cm. In some embodiments, the panel comprises LG3BP and C163A and the reversal ratio is 0.07.

In some aspects, provided herein is a method of determining the likelihood that a pulmonary nodule in a subject is lung cancer, comprising: (a) contacting a blood sample obtained from the subject with a proteolytic enzyme to produce peptide fragments from a panel of proteins present in the blood sample, wherein the panel comprises C163A and LG3BP; (b) combining the produced peptide fragments from the panel from step (a) with labeled, synthetic peptide fragments which correspond to the produced peptide fragments from the panel; (c) performing selected reaction monitoring mass spectrometry to measure the abundance of the peptide fragments from step (b); (d) calculating a probability of lung cancer score based on the peptide fragment measurements of step (c); and (e) ruling in lung cancer for the subject if the score in step (d) is equal to or higher than a pre-determined score; and wherein the selected reaction monitoring mass spectrometry is performed using a LG3BP antibody described herein and a C163A antibody described herein.

In some embodiments, when lung cancer is ruled in, the subject is monitored periodically. In some embodiments, the subject has low to moderate cancer risk. In some embodiments, the methods provided herein further comprise a physician's assessment of cancer risk. In some embodiments, the subject is assigned a physician's assessment of cancer risk from between 0 to 1. In some embodiments, the cancer risk is determined by a cancer risk predictor $Ci(k)$ determined as $$Ci(k) = \begin{cases} 0, & \text{if } pCA(k) \le Ti \\ pCA(k), & \text{otherwise} \end{cases}$$

wherein the decision threshold $Ti$ is the median value of $\{Si(k)\}$ of patients with nodules no larger than 15 mm.

Definitions

In order that the present description may be more readily understood, certain terms are first defined. Additional definitions are set forth throughout the detailed description.

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., C163A or LG3BP). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

"And/or" as used herein, for example, with option A and/or option B, encompasses the separate embodiments of (i) option A, (ii) option B, and (iii) option A plus option B.

A "CDR" of a variable domain are amino acid residues within the hypervariable region that are identified in accordance with the definitions of the Kabat, Chothia, the cumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al. (2009) mAbs 1:1). Antibodies described herein may be of any allotype. As used herein, antibodies referred to as "IgG1f" or "IgG1.1f" isotype are IgG1 and effectorless IgG1.1 antibodies, respectively, of the allotype "f," i.e., having 214R, 356E and 358M according to the EU index as in Kabat.

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to C163A or LG3BP is substantially free of antibodies that specifically bind antigens other C163A or LG3BP).

An "effector function" refers to the interaction of an antibody Fc region with an Fc receptor or ligand, or a biochemical event that results therefrom. Exemplary "effector functions" include Clq binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (Clq) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second ($C_{H2}$) and third ($C_{H3}$) constant domains of the antibody's two heavy chains; IgM and IgE Fc regions comprise three heavy chain constant domains ($C_H$ domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al. (2009) mAbs 1:1).

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 J Immunol 161:4083).

The term "hinge" includes wildtype hinges as well as variants thereof (e.g., non-naturally-occurring hinges or modified hinges). For example, the term "IgG2 hinge" includes wildtype IgG2 hinge and variants having 1, 2, 3, 4, 5, 1-3, 1-5, 3-5 and/or at most 5, 4, 3, 2, or 1 mutations, e.g., substitutions, deletions or additions. Exemplary IgG2 hinge variants include IgG2 hinges in which 1, 2, 3 or all 4 cysteines (C219, C220, C226 and C229) are changed to another amino acid. In a specific embodiment, an IgG2 comprises a C219S substitution. In certain embodiments, a hinge is a hybrid hinge that comprises sequences from at least two isotypes. For example, a hinge may comprise the upper, middle or lower hinge from one isotype and the remainder of the hinge from one or more other isotypes. For example, a hinge can be an IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains as well as variants thereof (e.g., non-naturally-occurring CH1 domains or modified CH1 domains). For example, the term "CH1 domain" includes wildtype CH1 domains and variants having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that modify a biological activity of an antibody, such as ADCC, CDC or half-life. Modifications to the CH1 domain that affect a biological activity of an antibody are provided herein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that modify a biological activity of an antibody, such as ADCC, CDC or half-life. In certain embodiments, a CH2 domain comprises the substitutions A330S/P331S that reduce effector function. Other modifications to the CH2 domain that affect a biological activity of an antibody are provided herein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that modify a biological activity of an antibody, such as ADCC, CDC or half-life. Modifications to the CH3 domain that affect a biological activity of an antibody are provided herein.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al. (2009) mAbs 1:1).

The term "epitope" or "antigenic determinant" refers to a site on an antigen (e.g., C163A or LG3BP) to which an immunoglobulin or antibody specifically binds. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from an antigen (e.g., from C163A or LG3BP) are tested for reactivity with a given antibody (e.g., anti-C163A or LG3BP antibody). Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the same epitope with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same $V_H$ and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label RIA using I-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE 2000 instrument using the predetermined antigen, e.g., recombinant C163A or LG3BP antigen, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to C163A or LG3BP" refers to an antibody that binds to soluble or cell bound human C163A or LG3BP with a $K_D$ of $10^{-7}$ M or less, such as approximately less than $10^{-8}$ M, $10^{-9}$ M or $10^{-10}$ M or even lower.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e. $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system or flow cytometry and Scatchard analysis.

As used herein, the term "high affinity" for an IgG antibody refers to an antibody having a $K_D$ of $10^{-8}$ M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$ M or less.

The term "$EC_{50}$" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "binds to an immobilized C163A or LG3BP antigen," refers to the ability of an antibody described herein to bind to a C163A or LG3BP antigen, for example, expressed on the surface of a cell or which is attached to a solid support.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein, e.g., in Table 2, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)). Alternatively, in another embodiment, mutations can be introduced randomly along all or part of an antibody coding sequence, such as by saturation mutagenesis, and the resulting modified antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the World Wide Web at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See World Wide Web at ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be C163A or LG3BP, or a fragment thereof.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The term "patient" includes human and other mammalian subjects that receive either prophylactic or therapeutic treatment.

As used herein, the term "subject" includes any human or non-human animal.

The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "µg" and "µM".

The articles "a" and "an" are used herein to refer to one or to more than one (i.e., to at least one) of the grammatical object of the article. By way of example, "an element" means one element or more than one element.

The amount of a biomarker (e.g., C163A or LG3BP) in a subject is "significantly" higher or lower than the normal amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level, altered activity, changes in biomarker inhibition/blocking, changes in test agent binding, and the like.

The "amount" of a marker, e.g., level of C163A or LG3BP, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "control" refers to any reference standard suitable to provide a comparison to the antigens (e.g., C163A or LG3BP antigen) in the test sample. In one embodiment, the control comprises obtaining a "control sample" from which antigen levels are detected and compared to the antigen levels from the test sample. Such a control sample may comprise any suitable sample, including but not limited to a sample from a control lung cancer patient (can be stored sample or previous sample measurement) with a known outcome; normal tissue or cells isolated from a subject, such as a normal patient or the lung cancer patient, cultured primary cells/tissues isolated from a subject such as a normal subject or the lung cancer patient, adjacent normal cells/tissues obtained from the same organ or body location of the lung cancer patient, a tissue or cell sample isolated from a normal subject, or a primary cells/tissues obtained from a depository. In another preferred embodiment, the control may comprise a reference standard antigen level from any suitable source, including but not limited to housekeeping genes, an antigen level range from normal tissue (or other previously analyzed control sample), a previously determined antigen level range within a test sample from a group of patients, or a set of patients with a certain outcome or receiving a certain treatment. It will be understood by those of skill in the art that such control samples and reference standard antigen levels can be used in combination as controls in the methods of the present invention.

The "normal" level of a marker is the level of the marker in cells of a subject, e.g., a human patient, not afflicted with a disease or disorder related to aberrant marker levels.

Such antibodies, described herein, can be used in any one of well-known immunoassay forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA), ELISA, etc. alone or in combination or alternatively with PCR, NMR, MALDI-TOF, LC-MS/MS, are known to those of ordinary skill in the art. For Example, and without limitation, the antibodies described herein may be used in ProQuantum™ assays which leverage proximity ligation and PCR technologies. Without being bound by any particular methodology or theory, and purely for the purpose of exemplification, ProQuantum™ immunoassays (ThermoFisher Scientific; MA, U.S.A) utilize a matched pair of target-specific antibodies each conjugated to a DNA oligonucleotide. This platform leverages the sensitivity and large dynamic range of Applied Biosystems™ TaqMan™ real-time PCR technology. During antibody—target binding, the two DNA oligos are brought into close proximity, which then allows for ligation of the two strands and subsequent creation of template strand for amplification, e.g., using qPCR, RT/PCR, digital PCR (dPCR) and the like.

Such reagents can also be used to monitor protein levels in a cell or tissue, e.g., white blood cells or lymphocytes, as part of a clinical testing procedure, e.g., in order to monitor an optimal dosage of an inhibitory agent. Detection can be facilitated by coupling (e.g., physically linking) the antibody to a detectable substance. Examples of detectable substances include various enzymes, prosthetic groups, fluorescent materials, luminescent materials, bioluminescent materials, oligonucleotides, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$; and examples of nanoparticles (eg. quantum dots) in the visible and invisible to the naked eye eg in the ultraviolet (UV) and near infrared (NIR) regions Such reagents can also be used with any number of biological samples.

Biological samples can be collected from a variety of sources from a patient including a body fluid sample, cell sample, or a tissue sample comprising nucleic acids and/or proteins. In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Samples can contain live cells/tissue, fresh frozen cells, fresh tissue, biopsies, fixed cells/tissue, cells/tissue embedded in a medium, such as paraffin, histological slides, or any combination thereof.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "prognosis" includes a prediction of the probable course and outcome of a disease (e.g., lung cancer) or the likelihood of recovery from the disease (e.g., lung cancer). In some embodiments, the use of statistical algorithms provides a prognosis of a disease (e.g., lung cancer) in an individual.

The terms "response" or "responsiveness" refers to response to a therapy. For example, an anti-viral response includes reduction of viral load or inhibiting viral infection. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a subject will exhibit a favorable response is equivalent to evaluating the likelihood that the subject will not exhibit favorable response (i.e., will exhibit a lack of response or be non-responsive).

Various aspects described herein are described in further detail in the following subsections.

Antibodies

In some embodiments, the antibodies or antigen binding fragments thereof provided herein include (e.g., comprise, consist essentially of, or consist of at least one (e.g., one, two or three) heavy chain complementarity determining region (CDR) with at least about 85%, 90%, 95%, 96%, 97%, 98% or 99% identity to a heavy chain CDR sequence selected from the group consisting of the heavy chain CDR sequences listed in Table 1A or 1B.

In some embodiments, the antibodies or antigen binding fragments thereof provided herein may also include (e.g., comprise, consist essentially of, or consist of at least one (e.g., one, two or three) light chain complementarity determining region (CDR) with at least about 85%, 90%, 95%, 96%, 97%, 98% or 99% identity to a light chain CDR sequence selected from the group consisting of the light chain CDR sequences listed in Table 1A or 1B.

In some embodiments, the antibodies or antigen binding fragments thereof provided herein include (e.g., comprise, consist essentially of, or consist of at least one (e.g., one, two or three) heavy chain complementarity determining region (CDR) set forth in Table 1A or 1B. In some embodiments, the antibodies or antigen binding fragments thereof provided herein may also include (e.g., comprise, consist essentially of, or consist of at least one (e.g., one, two or three) light chain complementarity determining region (CDR) set forth in Table 1A or 1B.

In some embodiments, the antibodies or antigen binding fragments thereof provided herein include (e.g., comprise, consist essentially of, or consist of) a) a combination of a heavy chain CDR1, CDR2, and CDR3 as set forth in any one heavy chain row of Table 1A or 1B; and/or b) a combination of a light chain CDR1, CDR2, and CDR3 as set forth in any one light chain row of Table 1A or 1B.

In specific embodiments, the light chain CDR(s) belongs to the same laboratory designated antibody in Table 1A or 1B as the heavy chain CDR(s).

In some embodiments, the antibodies or antigen binding fragments thereof provided herein include (e.g., comprise, consist essentially of, or consist of) the amino acid sequence of the $V_H$ shown in Table 2A or 2B. In some embodiments, the antibodies or antigen binding fragments thereof provided herein also include the amino acid sequence of the $V_L$ shown in Table 2A or 2B.

In some embodiments, the $V_H$ and/or $V_L$ of the antibodies or antigen binding fragments thereof comprise an amino acid sequence that is at least 85%, 90%, 95%, 96%, 97%, 98% or 99% identical to the amino acid sequences of the $V_H$ and/or $V_L$ set forth in Table 2A or 2B.

In specific embodiments, the $V_L$ belongs to the same laboratory designated antibody in Table 2A or 2B as the $V_H$.

In some embodiments, the antibodies or antigen binding fragments thereof provided herein specifically bind to C163A or LG3BP, or a fragment thereof. For example, in one embodiment, the antibody or antigen binding fragment thereof provided herein may specifically bind to a peptide or fragment of LG3BP comprising a sequence set forth in VEIFYR(SEQ ID NO: 41). In another embodiment, the antibody or antigen binding fragment thereof provided herein may specifically bind to a peptide or fragment of C163A comprising a sequence set forth in INPA.

Also provided are modified antibodies and/or antigen binding fragments which can be prepared using an antibody having one or more of the $V_H$ and/or $V_L$ sequences disclosed herein as starting material to engineer a modified antibody which may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al. (1991) *Sequences of Proteins of Immunological Interest*, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are antibodies which have one or more methionine residues in the heavy and/or light chain CDRs replaced with amino acid residues which do not undergo oxidative degradation.

Similarly, deamidation sites may be removed from antibodies described herein, particularly in the CDRs.

The term Fc domain or region herein is used to define a C-terminal region of an immunoglobulin heavy chain, including native sequence Fc regions and variant Fc regions. Although the boundaries of the Fc domain of an immunoglobulin heavy chain might vary, the human IgG heavy chain Fc domain is usually defined to stretch from an amino acid residue at position Cys226, or from Pro230, to the carboxyl-terminus thereof. The C-terminal lysine of the Fc domain may be removed, for example, by recombinantly engineering the nucleic acid encoding it.

In embodiments, the antibody comprises an Fc domain. In an embodiment, the Fc domain has the same sequence or 99% or greater sequence similarity with a human IgG1 Fc domain. In an embodiment, the Fc domain has the same sequence or 99% or greater sequence similarity with a human IgG2 Fc domain. In an embodiment, the Fc domain has the same sequence or 99% or greater sequence similarity with a human IgG3 Fc domain. In an embodiment, the Fc domain has the same sequence or 99% or greater sequence similarity with a human IgG4 Fc domain. In an embodiment, the Fc domain is not mutated. In an embodiment, the Fc domain is mutated at the CH2—CH3 domain interface to increase the affinity of IgG for FcRn at acidic but not neutral pH (Dall'Acqua et al, 2006; Yeung et al, 2009). In an embodiment, the Fc domain has the same sequence as a human IgG1 Fc domain.

In an embodiment, the antibody comprises the following Fc region sequence:

TABLE 1A

Exemplary CDRs of the C163A antibodies are set forth in the following table:

| Client Sample Name | Chain type | CDR-1 | CDR-2 | CDR-3 | Isotype |
|---|---|---|---|---|---|
| C163A.1_HC | HC | GFTFSSYA (SEQ ID NO: 1) | ISSSGSYT (SEQ ID NO: 2) | ARQEGLWSFAY (SEQ ID NO: 3) | mIGG1 |
| C163A.1_LC | LC | QSLLDSDGKTY (SEQ ID NO: 4) | LVS (SEQ ID NO: 5) | WQGTHFPWT (SEQ ID NO: 6) | mKAPPA |
| C163A.2_HC | HC | GFTFSSYA (SEQ ID NO: 1) | ISSSGSYT (SEQ ID NO: 2) | ARQEGLWSFAY (SEQ ID NO: 3) | mIGG1 |
| C163A.2_LC | LC | QSLLDSDGKTY (SEQ ID NO: 4) | LVS (SEQ ID NO: 5) | WQGTHFPWT (SEQ ID NO: 6) | mKAPPA |

TABLE 1B

Exemplary CDRs of the LG3BP antibodies are set forth in the following table:

| Client Sample Name | Chain type | CDR-1 | CDR-2 | CDR-3 | Isotype |
|---|---|---|---|---|---|
| LG3BP.1_HC | HC | GYTFSSYW (SEQ ID NO: 7) | INRSNGRT (SEQ ID NO: 8) | TKWGVTSDY (SEQ ID NO: 9) | mIGG1 |
| LG3BP.1_LC | LC | SNVNY (SEQ ID NO: 10) | DTS (SEQ ID NO: 11) | FQGSGYPRT (SEQ ID NO: 12) | mKAPPA |
| LG3BP.2_HC | HC | GYTFSSYW (SEQ ID NO: 7) | INRSNGRT (SEQ ID NO: 8) | TKWGVTSDY (SEQ ID NO: 9) | mIGG1 |
| LG3BP.2_LC | LC | SNVNY (SEQ ID NO: 10) | DTS (SEQ ID NO: 11) | FQGSGYPRT (SEQ ID NO: 12) | mKAPPA |
| LG3BP.3_HC | HC | GYTFSSYW (SEQ ID NO: 7) | INRSNGRT (SEQ ID NO: 8) | TKWGVTSDY (SEQ ID NO: 9) | mIGG1 |
| LG3BP.3_LC | LC | SNVNY (SEQ ID NO: 10) | DTS (SEQ ID NO: 11) | FQGSGYPRT (SEQ ID NO: 12) | mKAPPA |

TABLE 2A

Exemplary variable domains of the C163A antibodies are set forth in the following table:

Variable Domain Protein Sequence

C163A.1_HC  EVMLVESGGGLVKPGSSLKLSCAASGFTFSSYAMSWVRQTPEKRLEWVA
VISSSGSYTFYTDSVKGRFTISRDNAKNTLYLQMSSLRSEDTAMYYCARQE
GLWSFAYWGQGTLVTVSA (SEQ ID NO: 13)

C163A.1_LC  DVVLTQTPLTLSVTIGQPASISCKSSQSLLDSDGKTYLNWLLQRPGQSPKRL
IYLVSKLDSGVPDRFTGSGSGTDFTLKISRVEAEDLGVYYCWQGTHFPWTF
GGGTKLEIK (SEQ ID NO: 14)

C163A.2_HC  EVMLVESGGGLVKPGSSLKLSCAASGFTFSSYAMSWVRQTPEKRLEWVA
VISSSGSYTFYTDSVKGRFTISRDNAKNTLYLQMSSLRSEDTAMYYCARQE
GLWSFAYWGQGTLVTVSA (SEQ ID NO: 13)

C163A.2_LC  DVVLTQTPLTLSVTIGQPASISCKSSQSLLDSDGKTYLNWLLQRPGQSPKRL
IYLVSKLDSGVPDRFTGSGSGTDFTLKISRVEAEDLGVYYCWQGTHFPWTF
GGGTKLEIK (SEQ ID NO: 14)

TABLE 2B

Exemplary variable domains of the LG3BP antibodies are set forth in the following table:

Variable Domain Protein Sequence

LG3BP.1_HC  QVQLQQPGAELVKPGASVKLSCKASGYTFSSYWMHWVKQRPGQGLEWI
GEINRSNGRTNYNEKFKSKATLTVDKSSTTAYMQLSSLTSEDSAVYYCTK
WGVTSDYWGQGTTLTVSS (SEQ ID NO: 15)

LG3BP.1_LC  ENVLTQSPAIMSASPGEKVTMTCSASSNVNYMHWFQQKSSTSPKLWIYDT
SKLASGVPGRFSGSGSGNSYSLTISSMEAEDVATYYCFQGSGYPRTFGGGT
KLEIK (SEQ ID NO: 16)

LG3BP.2_HC  QVQLQQPGAELVKPGASVKLSCKASGYTFSSYWMHWVKQRPGQGLEWI
GEINRSNGRTNYNEKFKSKATLTVDKSSTTAYMQLSSLTSEDSAVYYCTK
WGVTSDYWGQGTTLTVSS (SEQ ID NO: 15)

TABLE 2B-continued

Exemplary variable domains of the LG3BP
antibodies are set forth in the following table:

Variable Domain Protein Sequence

LG3BP.2_LC  ENVLTQSPAIMSASPGEKVTMTCSASSNVNYMHWFQQKSSTSPKLWIYDT
SKLASGVPGRFSGSGSGNSYSLTISSMEAEDVATYYCFQGSGYPRTFGGGT
KLEIK (SEQ ID NO: 16)

LG3BP.3_HC  QVQLQQPGAELVKPGASVKLSCKASGYTFSSYWMHWVKQRPGQGLEWI
GEINRSNGRTNYNEKFKSKATLTVDKSSTTAYMQLSSLTSEDSAVYYCTK
WGVTSDYWGQGTTLTVSS (SEQ ID NO: 15)

LG3BP.3_LC  ENVLTQSPAIMSASPGEKVTMTCSASSNVNYMHWFQQKSSTSPKLWIYDT
SKLASGVPGRFSGSGSGNSYSLTISSMEAEDVATYYCFQGSGYPRTFGGGT
KLEIK (SEQ ID NO: 16)

TABLE 3A

Exemplary variable domains of the C163A
antibodies are set forth in the following table:

Variable Domain Nucleotide Sequence

C163A.1_HC  GAAGTGATGCTGGTGGAGTCTGGGGGAGGCTTAGTGAAGCCTGGAAGTTC
CCTGAAACTCTCCTGTGCAGCCTCTGGATTCACTTTCAGTAGCTATGCCATG
TCTTGGGTTCGCCAGACTCCGGAGAAGAGGCTGGAATGGGTCGCAGTCATT
AGTAGTAGTGGAAGTTACACCTTCTATACAGACAGTGTGAAGGGGCGATTC
ACCATCTCCAGAGACAATGCCAAGAACACCCTGTACCTGCAAATGAGCAG
TCTGAGGTCTGAAGACACGGCCATGTATTACTGTGCAAGACAGGAGGGGTT
ATGGTCGTTTGCTTACTGGGGCCAAGGGACTCTGGTCACTGTCTCTGCA
(SEQ ID NO: 17)

C163A.1_LC  GATGTTGTGCTGACCCAGACTCCACTCACTTTGTCGGTTACCATTGGACAA
CCAGCCTCCATCTCTTGCAAGTCAAGTCAGAGCCTCTTAGATAGTGATGGA
AAGACATATTTGAATTGGTTGTTACAGAGGCCAGGCCAGTCTCCAAAGCGC
CTAATCTATCTGGTGTCTAAACTGGACTCTGGAGTCCCTGACAGGTTCACT
GGCAGTGGATCAGGGACAGATTTCACACTGAAAATCAGCAGAGTGGAGGC
TGAGGATTTGGGAGTTTATTATTGCTGGCAAGGTACACATTTTCCGTGGAC
GTTCGGTGGAGGCACCAAGCTGGAAATCAAA (SEQ ID NO: 18)

C163A.2_HC  GAAGTGATGCTGGTGGAGTCTGGGGGAGGCTTAGTGAAGCCTGGAAGTTC
CCTGAAACTCTCCTGTGCAGCCTCTGGATTCACTTTCAGTAGCTATGCCATG
TCTTGGGTTCGCCAGACTCCGGAGAAGAGGCTGGAATGGGTCGCAGTCATT
AGTAGTAGTGGAAGTTACACCTTCTATACAGACAGTGTGAAGGGGCGATTC
ACCATCTCCAGAGACAATGCCAAGAACACCCTGTACCTGCAAATGAGCAG
TCTGAGGTCTGAAGACACGGCCATGTATTACTGTGCAAGACAGGAGGGGTT
ATGGTCGTTTGCTTACTGGGGCCAAGGGACTCTGGTCACTGTCTCTGCA
(SEQ ID NO: 17)

C163A.2_LC  GATGTTGTGCTGACCCAGACTCCACTCACTTTGTCGGTTACCATTGGACAA
CCAGCCTCCATCTCTTGCAAGTCAAGTCAGAGCCTCTTAGATAGTGATGGA
AAGACATATTTGAATTGGTTGTTACAGAGGCCAGGCCAGTCTCCAAAGCGC
CTAATCTATCTGGTGTCTAAACTGGACTCTGGAGTCCCTGACAGGTTCACT
GGCAGTGGATCAGGGACAGATTTCACACTGAAAATCAGCAGAGTGGAGGC
TGAGGATTTGGGAGTTTATTATTGCTGGCAAGGTACACATTTTCCGTGGAC
GTTCGGTGGAGGCACCAAGCTGGAAATCAAA (SEQ ID NO: 18)

TABLE 3B

Exemplary variable domains of the LG3BP
antibodies are set forth in the following table:

Variable Domain Nucleotide Sequence

LG3BP.1_HC  CAGGTCCAACTGCAGCAGCCTGGGGCTGAACTGGTGAAGCCTGGGGCTT
CAGTGAAGCTGTCCTGCAAGGCTTCTGGCTACACCTTCAGCAGCTACTGG
ATGCACTGGGTGAAGCAGAGGCCTGGACAAGGCCTTGAGTGGATTGGAG
AGATTAATCGTAGCAACGGTCGGACTAACTACAATGAGAAGTTCAAGAG
CAAGGCCACACTGACTGTAGACAAATCCTCCACCACAGCCTACATGCAA

TABLE 3B-continued

Exemplary variable domains of the LG3BP
antibodies are set forth in the following table:

Variable Domain Nucleotide Sequence

```
            CTCAGCAGCCTGACATCTGAGGACTCTGCGGTCTATTACTGTACAAAATG
            GGGTGTGACGAGTGACTACTGGGGCCAAGGCACCACTCTCACAGTCTCC
                          TCA (SEQ ID NO: 19)

LG3BP.1_LC GAAAATGTTCTCACCCAGTCTCCAGCAATCATGTCTGCATCTCCAGGGGA
            AAAGGTCACCATGACCTGCAGTGCCAGCTCAAATGTAAATTACATGCAC
            TGGTTCCAGCAGAAGTCTAGCACCTCCCCCAAACTCTGGATTTATGACAC
            ATCCAAACTGGCTTCTGGAGTCCCAGGTCGCTTCAGTGGCAGTGGGTCTG
            GAAACTCTTACTCTCTCACGATCAGCAGCATGGAGGCTGAAGATGTTGCC
            ACTTATTACTGTTTTCAGGGGAGTGGATACCCACGTACGTTCGGAGGGGG
                       GACCAAGCTGGAAATAAAA (SEQ ID NO: 20)

LG3BP.2_HC CAGGTCCAACTGCAGCAGCCTGGGGCTGAACTGGTGAAGCCTGGGGCTT
            CAGTGAAGCTGTCCTGCAAGGCTTCTGGCTACACCTTCAGCAGCTACTGG
            ATGCACTGGGTGAAGCAGAGGCCTGGACAAGGCCTTGAGTGGATTGGAG
            AGATTAATCGTAGCAACGGTCGGACTAACTACAATGAGAAGTTCAAGAG
            CAAGGCCACACTGACTGTAGACAAATCCTCCACCACAGCCTACATGCAA
            CTCAGCAGCCTGACATCTGAGGACTCTGCGGTCTATTACTGTACAAAATG
            GGGTGTGACGAGTGACTACTGGGGCCAAGGCACCACTCTCACAGTCTCC
                          TCA (SEQ ID NO: 19)

LG3BP.2_LC GAAAATGTTCTCACCCAGTCTCCAGCAATCATGTCTGCATCTCCAGGGGA
            AAAGGTCACCATGACCTGCAGTGCCAGCTCAAATGTAAATTACATGCAC
            TGGTTCCAGCAGAAGTCTAGCACCTCCCCCAAACTCTGGATTTATGACAC
            ATCCAAACTGGCTTCTGGAGTCCCAGGTCGCTTCAGTGGCAGTGGGTCTG
            GAAACTCTTACTCTCTCACGATCAGCAGCATGGAGGCTGAAGATGTTGCC
            ACTTATTACTGTTTTCAGGGGAGTGGATACCCACGTACGTTCGGAGGGGG
                       GACCAAGCTGGAAATAAAA (SEQ ID NO: 20)

LG3BP.3_HC CAGGTCCAACTGCAGCAGCCTGGGGCTGAACTGGTGAAGCCTGGGGCTT
            CAGTGAAGCTGTCCTGCAAGGCTTCTGGCTACACCTTCAGCAGCTACTGG
            ATGCACTGGGTGAAGCAGAGGCCTGGACAAGGCCTTGAGTGGATTGGAG
            AGATTAATCGTAGCAACGGTCGGACTAACTACAATGAGAAGTTCAAGAG
            CAAGGCCACACTGACTGTAGACAAATCCTCCACCACAGCCTACATGCAA
            CTCAGCAGCCTGACATCTGAGGACTCTGCGGTCTATTACTGTACAAAATG
            GGGTGTGACGAGTGACTACTGGGGCCAAGGCACCACTCTCACAGTCTCC
                          TCA (SEQ ID NO: 19)

LG3BP.3_LC GAAAATGTTCTCACCCAGTCTCCAGCAATCATGTCTGCATCTCCAGGGGA
            AAAGGTCACCATGACCTGCAGTGCCAGCTCAAATGTAAATTACATGCAC
            TGGTTCCAGCAGAAGTCTAGCACCTCCCCCAAACTCTGGATTTATGACAC
            ATCCAAACTGGCTTCTGGAGTCCCAGGTCGCTTCAGTGGCAGTGGGTCTG
            GAAACTCTTACTCTCTCACGATCAGCAGCATGGAGGCTGAAGATGTTGCC
            ACTTATTACTGTTTTCAGGGGAGTGGATACCCACGTACGTTCGGAGGGGG
                       GACCAAGCTGGAAATAAAA (SEQ ID NO: 20)
```

Nucleic Acids, Vectors, and Host Cells

Also provided are nucleotide sequences corresponding to (e.g., encoding) the C163A or LG3BP antibodies and antigen binding fragments disclosed herein. These sequences include all degenerate sequences related to the disclosed antibodies, i.e., all nucleic acids having a sequence that encodes one particular peptide and variants and derivatives thereof. Thus, while each particular nucleic acid sequence may not be written out herein, it is understood that each and every sequence is in fact disclosed and described herein through the disclosed polypeptide sequences.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence. Thus, a further object of the invention relates to a vector comprising a nucleic acid of the present invention.

Such vectors can be either circular or linear. Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione 5-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

In some instances, the disclosure includes cells comprising the nucleic acids (e.g., vectors) and/or peptides disclosed herein. Both prokaryotic and eukaryotic host cells, including insect cells, can be used as long as sequences requisite for maintenance in that host, such as appropriate replication origin(s), are present. For convenience, selectable markers are also provided. Host systems are known in the art and need not be described in detail herein. Prokaryotic host cells include bacterial cells, for example, *E. coli. B. subtilis*, and mycobacteria. Among eukaryotic host cells are yeast, insect, avian, plant, *C. elegans* (or nematode) and mammalian host cells. Examples of fungi (including yeast) host cells are *S. cerevisiae, Kluyveromyces Lactis* (*K. lactis*), species of *Candida* including C. alhicans and *C. glabrata, Aspergillus nidulans, Schizosaccharomyces pombe* (*S. pombe*), *Pichia pastoris*, and *Yarrowia lipolytica*. Examples of mammalian cells are COS cells, mouse L cells, LNCaP cells, Chinese hamster ovary (CHO) cells, human embryonic kidney (HEK) cells, and African green monkey cells. *Xenopus laevis* oocytes, or other cells of amphibian origin, may also be used.

In general, cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Transformation and transfection methods useful in the generation of the cells disclosed herein are described, e.g., in F. Ausubel et al., Current Protocols in Molecular Biology, John Wiley & Sons, New York, N.Y., (1998).

In some instances, the disclosed therapeutic compositions can include a vector (e.g., expression vector, a viral vector, an adeno-associated virus vector) comprising a nucleic acid encoding and an antibody or antigen binding fragment thereof described herein. As described herein, antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above.

In some embodiments, the nucleic acids encode a $V_H$ comprising the CDR sequences set forth in Table 1A or 1B. In some embodiments, the nucleic acids encode a $V_H$ comprising an amino acid that is at least about 85%, 90%, 95%, 96%, 97%, 98%, 99% or more, or the complete (100%) sequence of the $V_H$ set forth in Table 2A or 2B. In some embodiments, the nucleic acids encode the $V_H$ set forth in Table 2A or 2B.

In some embodiments, the nucleic acids encode a $V_L$ comprising the CDR sequences set forth in Table 1A or 1B. In some embodiments, the nucleic acids encode a $V_L$ comprising an amino acid that is at least about 85%, 90%, 95%, 96%, 97%, 98%, 99% or more, or the complete (100%) sequence of the $V_L$ set forth in Table 2A or 2B. In some embodiments, the nucleic acids encode the $V_L$ set forth in Table 2A or 2B.

Accordingly, also provided are vectors and cells which comprise a nucleotide sequence encoding a $V_H$ comprising an amino acid that is at least about 85%, 90%, 95%, 96%, 97%, 98%, 99% or more, or the complete (100%) sequence of the $V_H$ set forth in Table 2A or 2B; and/or a nucleotide sequence encoding a $V_L$ comprising an amino acid that is at least about 85%, 90%, 95%, 96%, 97%, 98%, 99% or more, or the complete (100%) sequence of the $V_L$ set forth in Table 2A or 2B.

The term "nucleic acid" or "nucleic acid molecule", as used herein, is intended to include DNA molecules and RNA molecules. A nucleic acid molecule may be single-stranded or double-stranded, but preferably is double-stranded DNA.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" as used herein refers to any molecule used to transfer a nucleic acid sequence to a host cell. In some aspects, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. In some aspects, a viral vector is utilized (e.g., a retrovirus, adenovirus, adeno-associated virus (AAV), herpes virus, and poxvirus, among others). It is understood in the art that many such viral vectors are available in the art. In yet other aspects, a non-viral plasmid vector may also be suitable in practicing the present invention. The vectors of the present invention may be constructed using standard recombinant techniques widely available to one skilled in the art. Such techniques may be found in common molecular biology references such as Sambrook et al., Molecular Cloning: A Laboratory Manual (2nd Edition, 1989).

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Diagnostic Assays

The present invention provides, in part, methods, systems, and code for accurately classifying whether a biological sample contains C163A or LG3BP and/or whether the levels of C163A or LG3BP are modulated (e.g., reduced or over-expressed), thereby indicative of the state of a disorder of interest, such as cancer and immune-inflamed or immuno-compromised conditions. In some embodiments, the present invention is useful for classifying a sample (e.g., from a subject) as associated with or at risk for a disease or immune disorder and to monitor response to intervention such as with the use of therapeutics.

These conditions could include but are not limited to measurement of over-expression of C163A related to outcome of coronary bypass (Goldstein, et al. *Atherosclerosis*. 2003 Oct;170(2):325-32) or as measurement of an anti-inflammatory outcome following glucocorticoid treatments (Schaer, et al. *Br J Haematol*. 2002 October;119(1):239-43). Conversely, reduced expression has been associated with rheumatoid synovium (Fonseca, et al. *Arthritis Rheum*. 2002 May; 46(5):1210-6). Expression of the C163A scavenger receptor within normal, lymphoma, carcinoma and sarcoma tissue specimens is also an area of investigation for utility in oncology (Nguyen, et al. *Am J Surg Pathol*. 2005 May; 29(5):617-24, and Lau, et al. *Am J Clin Pathol*. 2004 November; 122(5):794-801.), while the soluble form of the C163A protein predicts mortality in patients suffering from acute liver failure (Møller, et al. *J Hepatol*. 2007 Nov;47 (5):671-6.).

LG3BP levels are elevated in the blood of those infected with HW and in patients with cancer (Calabrese, et al. *Cytogenet Cell Genet*. 1995;69(3-4):223-5.) and has an emerging role as prognostic marker in Ewing's sarcoma (Zambelli, et al. *Int J Cancer*. 2010 Jan 1;126(1):41-52.), lung(Marchetti, et al. *Cancer Res*. 2002 May 1;62(9):2535-9), breast (Kimura, et al. *Int J Oncol*. 2020 February;56(2): 581-595, and Woodman, et al. *Int J Oncol*. 2016 Jul;49(1): 265-75.), thyroid (Kaliszewski, et al. *Endokrynol Pol*. 2006; 57 Suppl A:38-44.), colorectal (Piccolo E, et al.. *J Transl Med*. 2015 Jul. 30; 13:248) and oral squamous cell (Zhang, et al. *Cell Signal*. 2019 November;63:109359.) carcinoma. Targeting LG3BP with antibody intervention has been proposed as a therapeutic option in oncology (Stampolidis, et al. *Oncogene*. 2015 Jan 2;34(1):39-52.). Induction of LG3BP protein and measurement thereof may provide biological information related to the antiviral innate immune response (Xu, et al. *PLoS Pathog*. 2019 Aug 12;15(8)).

In some embodiments, the present invention is useful for classifying a sample (e.g., from a subject) as associated with or at risk for a disease, immune disorder, or condition associated with deficiency or over-expression of peptides encoded in the C163A or LG3BP proteins (e.g., benign nodules and/or lung cancer) using a statistical algorithm and/or empirical data (e.g., the presence, absence, or level of C163A or LG3BP).). For Example, and without limitation, such methods and analyses based on C163A and/or LG3BP, as disclosed herein, may be beneficial to tests related to tissue and blood diagnoses arising from epithelial carcinomas. Carcinoma, as used herein, refers to a malignant neoplasm of epithelial origin or cancer of the internal or external lining of the body. Carcinomas, malignancies of epithelial tissue, account for 80 to 90 percent of all cancer cases.

Epithelial tissue is found throughout the body. It is present in the skin, as well as the covering and lining of organs and internal passageways, such as the gastrointestinal tract.

Carcinomas are divided into two major subtypes: adenocarcinoma, which develops in an organ or gland, and squamous cell carcinoma, which originates in the squamous epithelium.

Adenocarcinomas generally occur in mucus membranes and are first seen as a thickened plaque-like white mucosa. They often spread easily through the soft tissue where they occur. Squamous cell carcinomas occur in many areas of the body. Most carcinomas affect organs or glands capable of secretion, such as the breasts, which produce milk, or the lungs, which secrete mucus, or colon or prostate or bladder, as well as hematologic diseases resulting from acute inflammatory responses. For Example, and without wishing to be bound by any particular theory or mode, after shedding, the soluble form (sCD163) may play an anti-inflammatory role, and may be a valuable diagnostic parameter for monitoring macrophage activation in inflammatory conditions. The soluble CD163 in plasma may act as a parameter in diseases affecting macrophage function and monocyte/macrophage load in the body. The concentration of sCD163 may reflect the number of macrophages of the 'alternative macrophage activation' phenotype, with a high CD163 expression playing a major role in dampening the inflammatory response and scavenging components of damaged cells, making sCD163 an attractive marker not only in cancer but in other inflammatory conditions e.g., infection, autoimmune disease, transplantation, and atherosclerosis. Similarly, LG3BP has been implicated in disorders, such as, Henoch-Schoenlein Purpura, Varicose Veins, Hemorrhagic Cystitis, Strongyloidiasis/disseminated strongyloidiasis and colorectal cancer. The galectins are a family of beta-galactoside-binding proteins implicated in modulating cell-cell and cell-matrix interactions. LG3BP has been found elevated in the serum of patients with cancer and in those infected by the human immunodeficiency virus (HIV). LG3BP may be implicated in immune response associated with natural killer (NK) and lymphokine-activated killer (LAK) cell cytotoxicity thus providing a potentially valuable marker in cancer and other inflammatory diseases.

An exemplary method for detecting the level of C163A or LG3BP, or a fragment thereof, and thus useful for classifying whether a sample is associated with a disease or disorder mediated by C163A or LG3BP or a clinical subtype thereof involves obtaining a biological sample from a test subject and contacting the biological sample with an antibody or antigen-binding fragment thereof of the present invention capable of detecting C163A or LG3BP such that the level of C163A or LG3BP is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a C163A or LG3BP-containing sample based upon a prediction or probability value and the presence or level of C163A or LG3BP. The use of a single learning statistical classifier system typically classifies the sample as a C163A or LG3BP-containing sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the a C163A or LG3BP-containing sample classification results to a clinician, e.g., a histopathologist or an oncologist.

In another embodiment, the method of the present invention further provides a diagnosis in the form of a probability that the individual has a condition or disorder associated with C163A or LG3BP. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a C163A or LG3BP-containing sample is further based on the symptoms (e.g., clinical factors) of the individual from which the sample is obtained. In some embodiments, the diagnosis of an individual as having a condition or disorder associated with C163A or LG3BP is followed by administering to the individual a therapeutically effective amount of a drug useful for treating one or more symptoms associated with the condition or disorder.

In one embodiment, the methods further involve obtaining a control biological sample (e.g., biological sample from a subject who does not have a condition or disorder associated with C163A or LG3BP), a biological sample from the subject during remission or before developing a condition or disorder associated with C163A or LG3BP, or a biological sample from the subject during treatment for developing a condition or disorder associated with C163A or LG3BP.

An exemplary method for detecting the presence or absence of C163A or LG3BP or fragments thereof is an antibody of the present invention, or fragment thereof, capable of binding to C163A or LG3BP, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect C163A or LG3BP, in a biological sample in vitro as well as in vivo. In vitro techniques for detection of C163A or LG3BP include enzyme linked immunosorbent assays (ELISAs), Western blots, immunoprecipitations, immunohistochemistry (IHC), intracellular flow cytometry and related techniques, and immunofluorescence. Furthermore, in vivo techniques for detection of C163A or LG3BP or a fragment thereof include introducing into a subject a labeled antibody described herein. For example, the antibody can be labeled with a radioactive, luminescent, fluorescent, or other similar marker whose presence and location in a subject can be detected by standard imaging techniques, either alone or in combination with imaging for other molecules, such as markers of cell type.

In one embodiment, the biological sample contains polypeptide molecules from the test subject. In certain embodiments, the sample may be serums, plasmas, cells, tissues, or body fluids, isolated by conventional means from a subject.

In another embodiment, the methods further involve obtaining a control biological sample from a control subject, contacting the control sample with a compound or agent capable of detecting C163A or LG3BP, or a fragment thereof, such that the presence of C163A or LG3BP, or the fragment thereof, is detected in the biological sample, and comparing the presence of C163A or LG3BP, or the fragment thereof, in the control sample with the presence of C163A or LG3BP, or the fragment thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of C163A or LG3BP, or a fragment thereof by use of an immunochromatographic or immunochemical assay, such as in a "sandwich" or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" C163A or LG3BP in a biological sample and the captured (or immobilized) C163A or LG3BP may be bound to a labeled form of an antibody of the invention for detection. Other standard embodiments of immunoassays are well-known the skilled artisan, including assays based on, for example, immunodiffusion, immunoelectrophoresis, immunohistopathology, immunohistochemistry, and histopathology.

In some aspects, the antibodies disclosed here can be used in a blood-based multiplexed assay to distinguish benign pulmonary nodules from malignant pulmonary nodules to classify patients with or without lung cancer. Such assay may be used in patients who present with symptoms of lung cancer, but do not have pulmonary nodules.

In certain aspects, the present invention provides a method of determining the likelihood that a lung condition in a subject is not cancer by measuring an abundance of a panel of proteins comprising C163A and/or LG3BP in a sample obtained from the subject; calculating a probability of cancer score based on the protein measurements and ruling out cancer for the subject if the score is lower than a pre-determined score. When cancer is ruled out, the subject does not receive a treatment protocol and undergoes periodic monitoring. Periodic monitoring can include for example pulmonary function test (PFT), pulmonary imaging, a biopsy or any combination thereof. In some embodiments, the imaging is an x-ray, a chest computed tomography (CT) scan, or a positron emission tomography (PET) scan. Additional information that may be used in combination with the above-mentioned diagnostic testing methodology includes advanced radiologic measures including 3D assessment of nodules, patient history, smoking and other environmental factors. For example, in some embodiments, the diagnostic methods provided herein may integrate the relative abundance of two proteins (LG3BP and C163A) with five clinical risk factors (age, smoking status, nodule diameter, nodule spiculation status and nodule location), and provide a numerical value, XL_2(k), for a subject k, as defined below:

$$XL\_2(k) = \begin{cases} \max(0, p(k) - 0.5), & \log_2\left(\frac{LG3BP}{C163A}\right) \le .38 \\ p(k), & \log_2\left(\frac{LG3BP}{C163A}\right) > .38 \end{cases}$$

$$p(k) = \frac{e^X}{1 + e^X}$$

$X = -6.8272 + 0.0391*\text{Age} + 0.7917*\text{Smoker} + 0.1274*\text{Diameter} + 1.0407*\text{Spiculation} + 0.7838*\text{Location}$ where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0). The linear function X that integrates the clinical risk factors is a simplification of the Mayo clinical risk predictor that eliminates the cancer risk history factor.

The invention provides unique advantages to the patient associated with early detection of lung cancer in a patient, including increased life span, decreased morbidity and mortality, decreased exposure to radiation during screening and repeat screenings and a minimally invasive diagnostic model. Importantly, the methods of the invention allow for a patient to avoid invasive procedures.

The routine clinical use of chest computed tomography (CT) scans identifies millions of pulmonary nodules annually, of which only a small minority are malignant but contribute to the dismal 15% five-year survival rate for patients diagnosed with non-small cell lung cancer (NSCLC). The early diagnosis of lung cancer in patients with pulmonary nodules is a top priority, as decision-making based on clinical presentation, in conjunction with current non-invasive diagnostic options such as chest CT and positron emission tomography (PET) scans, and other invasive alternatives, has not altered the clinical outcomes of patients with Stage I NSCLC. The subgroup of pulmonary nodules between 8 mm and 20 mm in size is increasingly recognized as being "intermediate" relative to the lower rate of malignancies below 8 mm and the higher rate of malignancies above 20 mm. Invasive sampling of the lung nodule by biopsy using transthoracic needle aspiration or bronchoscopy may provide a cytopathologic diagnosis of NSCLC, but are also associated with both false-negative and non-diagnostic results. In summary, a key unmet clinical need for the management of pulmonary nodules is a non-invasive diagnostic test that discriminates between malignant and benign processes in patients with indeterminate pulmonary nodules (IPNs), especially between 8 mm and 20 mm in size.

The clinical decision to be more or less aggressive in treatment is based on risk factors, primarily nodule size, smoking history and age in addition to imaging. As these are not conclusive, there is a great need for a molecular-based blood test that would be both non-invasive and provide complementary information to risk factors and imaging.

Accordingly, these and related embodiments will find uses in screening methods for lung conditions, and particularly lung cancer diagnostics. More importantly, the invention finds use in determining the clinical management of a patient. That is, the method of invention is useful in ruling in or ruling out a particular treatment protocol for an individual subject.

Cancer biology requires a molecular strategy to address the unmet medical need for an assessment of lung cancer risk. The field of diagnostic medicine has evolved with technology and assays that provide sensitive mechanisms for detection of changes in proteins.

The methods described herein use antibodies specific for biomarkers C163A or LG3BP for measuring the concentration of blood plasma proteins that are collectively changed in patients with a malignant PN. This protein signature is indicative of lung cancer. The antibodies disclosed herein can be used in any antibody-based detection methods such as ELISA, western blot, flow cytometry, etc. that provide for both quantification and identification of circulating proteins in plasma. In some embodiments, presented herein is a blood-based classification test to determine the likelihood that a patient presenting with a pulmonary nodule has a nodule that is benign or malignant. In some embodiments, the present invention presents a classification algorithm that predicts the relative likelihood of the PN being benign or malignant.

A two-protein panel assay comprising C163A and LG3BP were developed based on a large prospective study of subjects presenting with pulmonary nodules. The study has been described in WO/2019/079635 and WO/2017/192965 in detail, the content of which is incorporated by reference herein in its entirety.

The term "pulmonary nodules" (PNs) refers to lung lesions that can be visualized by radiographic techniques. A pulmonary nodule is any nodules less than or equal to three centimeters in diameter. In one example a pulmonary nodule has a diameter of about 0.8 cm to 2 cm.

The term "masses" or "pulmonary masses" refers to lung nodules that are greater than three centimeters maximal diameter.

The term "blood biopsy" refers to a diagnostic study of the blood to determine whether a patient presenting with a nodule has a condition that may be classified as either benign or malignant.

The term "acceptance criteria" refers to the set of criteria to which an assay, test, diagnostic or product should conform to be considered acceptable for its intended use. As used herein, acceptance criteria are a list of tests, references to analytical procedures, and appropriate measures, which are defined for an assay or product that will be used in a diagnostic. For example, the acceptance criteria for the classifier refer to a set of predetermined ranges of coefficients.

The term "average maximal AUC" refers to the methodology of calculating performance. For the present invention, in the process of defining the set of proteins that should be in a panel by forward or backwards selection proteins are removed or added one at a time. A plot can be generated with performance (AUC or partial AUC score on the Y axis and proteins on the X axis) the point which maximizes performance indicates the number and set of proteins the gives the best result.

The term "partial AUC factor or pAUC factor" is greater than expected by random prediction. At sensitivity=0.90 the pAUC factor is the trapezoidal area under the ROC curve from 0.9 to 1.0 Specificity/(0.1*0.1/2).

The term "incremental information" refers to information that may be used with other diagnostic information to enhance diagnostic accuracy. Incremental information is independent of clinical factors such as including nodule size, age, or gender.

The term "score" or "scoring" refers to the refers to calculating a probability likelihood for a sample. For the present invention, values closer to 1.0 are used to represent the likelihood that a sample is cancer, values closer to 0.0 represent the likelihood that a sample is benign.

The term "robust" refers to a test or procedure that is not seriously disturbed by violations of the assumptions on which it is based. For the present invention, a robust test is a test wherein the proteins or transitions of the mass spectrometry chromatograms have been manually reviewed and are "generally" free of interfering signals.

The term "coefficients" refers to the weight assigned to each protein used to in the logistic regression equation to score a sample.

In certain embodiments of the invention, it is contemplated that in terms of the logistic regression model of MC CV, the model coefficient and the coefficient of variation (CV) of each protein's model coefficient may increase or decrease, dependent upon the method (or model) of measurement of the protein classifier. For each of the listed proteins in the panels, there is about, at least, at least about, or at most about a 2-, 3-, 4-, 5-, 6-, 7-, 8-, 9-, or 10-, -fold or any range derivable therein for each of the coefficient and CV. Alternatively, it is contemplated that quantitative embodiments of the invention may be discussed in terms of as about, at least, at least about, or at most about 10, 20, 30, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

The term "best team players" refers to the proteins that rank the best in the random panel selection algorithm, i.e., perform well on panels. When combined into a classifier these proteins can segregate cancer from benign samples. "Best team player" proteins is synonymous with "cooperative proteins". The term "cooperative proteins" refers proteins that appear more frequently on high performing panels of proteins than expected by chance. This gives rise to a protein's cooperative score which measures how (in)frequently it appears on high performing panels. For example, a protein with a cooperative score of 1.5 appears on high performing panels 1.5x more than would be expected by chance alone.

The term "classifying" as used herein with regard to a lung condition refers to the act of compiling and analyzing expression data for using statistical techniques to provide a classification to aid in diagnosis of a lung condition, particularly lung cancer.

The term "classifier" as used herein refers to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of proteins in a biological sample. Protein expression levels in a subject can be compared to levels in patients previously diagnosed as disease free or with a specified condition.

The "classifier" maximizes the probability of distinguishing a randomly selected cancer sample from a randomly selected benign sample, i.e., the AUC of ROC curve.

In addition to the classifier's constituent proteins with differential expression, it may also include proteins with minimal or no biologic variation to enable assessment of variability, or the lack thereof, within or between clinical specimens; these proteins may be termed endogenous proteins and serve as internal controls for the other classifier proteins.

The term "normalization" or "normalizer" as used herein refers to the expression of a differential value in terms of a standard value to adjust for effects which arise from technical variation due to sample handling, sample preparation and measurement rather than biological variation of protein concentration in a sample. For example, when measuring the expression of a differentially expressed protein, the absolute value for the expression of the protein can be expressed in terms of an absolute value for the expression of a standard protein that is substantially constant in expression. This prevents the technical variation of sample preparation and measurement from impeding the measurement of protein concentration levels in the sample.

The term "condition" as used herein refers generally to a disease, event, or change in health status.

The term "treatment protocol" as used herein including further diagnostic testing typically performed to determine whether a pulmonary nodule is benign or malignant. Treatment protocols include diagnostic tests typically used to diagnose pulmonary nodules or masses such as for example, CT scan, positron emission tomography (PET) scan, bronchoscopy or tissue biopsy. Treatment protocol as used herein is also meant to include therapeutic treatments typically used to treat malignant pulmonary nodules and/or lung cancer such as for example, chemotherapy, radiation or surgery.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop a hyperproliferative disease) b. prognosis (predicting whether a patient will likely have a better or worse outcome at a pre-selected time in the future) c. therapy selection d. therapeutic drug monitoring e. relapse monitoring.

The American Lung Cancer Society provides the following lung cancer staging definitions. In stage TO, there is no evidence of primary tumor. In stage Tis, there is carcinoma in situ. Stage T1 denotes tumors of 3 cm or less. Stage T1a denotes tumors having 2 cm or less. Stage T1b denotes a tumor having a dimension of more than 2 cm but less than 3 cm. Stage T2 denotes tumors of having dimensions of more than 3 cm but 7 cm or less. Stage T2a denotes tumors having dimensions of more than 3 cm but 5 cm or less. Stage T2b denotes tumors having more than 5 cm in dimension but being 7 cm or less. Stage T3 denotes tumors that are more than 7 cm or those tumors that invades the chest wall, phrenic nerve, diaphragm, parietal pleura, parietal pericardium or mediastinal pleura; or a tumor in the main bronchus that is less than 2 cm. Stage T4 denotes tumors that invades any of: heart, esophagus, mediastinum, trachea, recurrent laryngeal nerve, carina, vertebral body, or a separate tumor nodule in a different ipsilateral lobe.

In some embodiments, for example, classification of a biological sample as being derived from a subject with a lung condition may refer to the results and related reports generated by a laboratory, while diagnosis may refer to the act of a medical professional in using the classification to identify or verify the lung condition.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

As used herein, "lung cancer" preferably refers to cancers of the lung, but may include any disease or other disorder of the respiratory system of a human or other mammal. Respiratory neoplastic disorders include, for example small cell carcinoma or small cell lung cancer (SCLC), non-small cell carcinoma or non-small cell lung cancer (NSCLC), squamous cell carcinoma, adenocarcinoma, broncho-alveolar carcinoma, mixed pulmonary carcinoma, malignant pleural mesothelioma, undifferentiated large cell carcinoma, giant cell carcinoma, synchronous tumors, large cell neuroendocrine carcinoma, adenosquamous carcinoma, undifferentiated carcinoma; and small cell carcinoma, including oat cell cancer, mixed small cell/large cell carcinoma, and combined small cell carcinoma; as well as adenoid cystic carcinoma, hamartomas, mucoepidermoid tumors, typical carcinoid lung tumors, atypical carcinoid lung tumors, peripheral carcinoid lung tumors, central carcinoid lung tumors, pleural mesotheliomas, and undifferentiated pulmonary carcinoma and cancers that originate outside the lungs such as secondary cancers that have metastasized to the lungs from other parts of the body. Lung cancers may be of any stage or grade. Preferably the term may be used to refer collectively to any dysplasia, hyperplasia, neoplasia, or metastasis in which the protein biomarkers expressed above normal levels as may be determined, for example, by comparison to adjacent healthy tissue.

Examples of non-cancerous lung condition include chronic obstructive pulmonary disease (COPD), benign tumors or masses of cells (e.g., hamartoma, fibroma, neurofibroma), granuloma, sarcoidosis, and infections caused by bacterial (e.g., tuberculosis) or fungal (e.g. histoplasmosis) pathogens. In certain embodiments, a lung condition may be associated with the appearance of radiographic PNs.

As used herein, "lung tissue", and "lung cancer" refer to tissue or cancer, respectively, of the lungs themselves, as well as the tissue adjacent to and/or within the strata underlying the lungs and supporting structures such as the pleura, intercostal muscles, ribs, and other elements of the respiratory system. The respiratory system itself is taken in this context as representing nasal cavity, sinuses, pharynx, larynx, trachea, bronchi, lungs, lung lobes, aveoli, aveolar ducts, aveolar sacs, aveolar capillaries, bronchioles, respiratory bronchioles, visceral pleura, parietal pleura, pleural cavity, diaphragm, epiglottis, adenoids, tonsils, mouth and tongue, and the like. The tissue or cancer may be from a mammal and is preferably from a human, although monkeys, apes, cats, dogs, cows, horses and rabbits are within the scope of the present invention. The term "lung condition" as used herein refers to a disease, event, or change in health status relating to the lung, including for example lung cancer and various non-cancerous conditions.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

The term "biomarker protein" as used herein refers to a polypeptide in a biological sample from a subject with a lung condition versus a biological sample from a control subject. A biomarker protein includes not only the polypeptide itself, but also minor variations thereof, including for example one or more amino acid substitutions or modifications such as glycosylation or phosphorylation.

The term "biomarker protein panel" as used herein refers to a plurality of biomarker proteins. In certain embodiments, the expression levels of the proteins in the panels can be correlated with the existence of a lung condition in a subject. In certain embodiments, biomarker protein panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 proteins. In certain embodiments, the biomarker proteins panels comprise from 100-125 proteins, 125-150 proteins, 150-200 proteins or more.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "ruling out" as used herein is meant that the subject is selected not to receive a treatment protocol.

The term "ruling-in" as used herein is meant that the subject is selected to receive a treatment protocol.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

Using the methods of the current invention, a clinical assessment of a patient is first performed. If there exists is a higher likelihood for cancer, the clinician may rule in the disease which will require the pursuit of diagnostic testing options yielding data which increase and/or substantiate the likelihood of the diagnosis. "Rule in" of a disease requires a test with a high specificity.

"FN" is false negative, which for a disease state test means classifying a disease subject incorrectly as non-disease or normal.

"FP" is false positive, which for a disease state test means classifying a normal subject incorrectly as having disease.

The term "rule in" refers to a diagnostic test with high specificity that coupled with a clinical assessment indicates a higher likelihood for cancer. If the clinical assessment is a lower likelihood for cancer, the clinician may adopt a stance to rule out the disease, which will require diagnostic tests which yield data that decrease the likelihood of the diagnosis. "Rule out" requires a test with a high sensitivity.

The term "rule out" refers to a diagnostic test with high sensitivity that coupled with a clinical assessment indicates a lower likelihood for cancer.

The term "sensitivity of a test" refers to the probability that a patient with the disease will have a positive test result. This is derived from the number of patients with the disease who have a positive test result (true positive) divided by the total number of patients with the disease, including those with true positive results and those patients with the disease who have a negative result, i.e. false negative.

The term "specificity of a test" refers to the probability that a patient without the disease will have a negative test result. This is derived from the number of patients without the disease who have a negative test result (true negative) divided by all patients without the disease, including those with a true negative result and those patients without the disease who have a positive test result, e.g. false positive. While the sensitivity, specificity, true or false positive rate, and true or false negative rate of a test provide an indication of a test's performance, e.g. relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" is calculated by TN/(TN+FN) or the true negative fraction of all negative test results. It also is inherently impacted by the prevalence of the disease and pre-test probability of the population intended to be tested.

The term "disease prevalence" refers to the number of all new and old cases of a disease or occurrences of an event during a particular period. Prevalence is expressed as a ratio in which the number of events is the numerator and the population at risk is the denominator.

The term disease incidence refers to a measure of the risk of developing some new condition within a specified period of time; the number of new cases during some time period, it is better expressed as a proportion or a rate with a denominator.

Lung cancer risk according to the "National Lung Screening Trial" is classified by age and smoking history. High risk-age≥55 and ≥30 pack-years smoking history; Moderate risk-age≥50 and ≥20 pack-years smoking history; Low risk-<age 50 or <20 pack-years smoking history.

The term "negative predictive value" (NPV) refers to the probability that a negative test correctly identifies a patient without the disease, which is the number of true negatives divided by the sum of true negatives and false negatives. A positive result from a test with a sufficient PPV can be used to rule in the disease for a patient, while a negative result from a test with a sufficient NPV can be used to rule out the disease, if the disease prevalence for the given population, of which the patient can be considered a part, is known.

The clinician must decide on using a diagnostic test based on its intrinsic performance parameters, including sensitivity and specificity, and on its extrinsic performance parameters, such as positive predictive value and negative predictive value, which depend upon the disease's prevalence in a given population.

Additional parameters which may influence clinical assessment of disease likelihood include the prior frequency and closeness of a patient to a known agent, e.g. exposure risk, that directly or indirectly is associated with disease causation, e.g. second hand smoke, radiation, etc., and also the radiographic appearance or characterization of the pulmonary nodule exclusive of size. A nodule's description may include solid, semi-solid or ground glass which characterizes it based on the spectrum of relative gray scale density employed by the CT scan technology.

"Mass spectrometry" refers to a method comprising employing an ionization source to generate gas phase ions from an analyte presented on a sample presenting surface of a probe and detecting the gas phase ions with a mass spectrometer.

In some embodiments, the technology liquid chromatography selected reaction monitoring mass spectrometry (LC-SRM-MS) is used to assay the expression levels of select protein panels in which the proteins are found in the blood.

In an embodiment of the invention, panels comprising C163A and LG3BP were validated for ruling out lung cancer in a subject. In some aspects, protein panels include additional proteins. In some aspects, the pulmonary nodule is about between 1 mm to 80 mm. For example, the pulmonary nodule can be between 8 mm-30 mm.

Bioinformatic and biostatistical analyses were used first to identify individual proteins with statistically significant differential expression, and then using these proteins to derive one or more combinations of proteins or panels of proteins, which collectively demonstrated superior discriminatory performance compared to any individual protein. Bioinformatic and biostatistical methods are used to derive coefficients (C) for each individual protein in the panel that reflects its relative expression level, i.e. increased or decreased, and its weight or importance with respect to the panel's net discriminatory ability, relative to the other proteins. The quantitative discriminatory ability of the panel can be expressed as a mathematical algorithm with a term for each of its constituent proteins being the product of its coefficient and the protein's plasma expression level (P) (e.g., as measured by LC-SRM-MS), e.g. C x P, with an algorithm consisting of n proteins described as: $C_1 \times P_1 + C_2 \times P_2 + C_3 \times P_3 + \ldots + C_n \times P_n$. An algorithm that discriminates between disease states with a predetermined level of statistical significance may be refers to a "disease classifier". In addition to the classifier's constituent proteins with differential expression, it may also include proteins with minimal or no biologic variation to enable assessment of variability, or the lack thereof, within or between clinical specimens; these proteins may be termed typical native proteins and serve as internal controls for the other classifier proteins.

In certain embodiments, peptide expression levels are measured by MS. MS analyzes the mass spectrum produced by an ion after its production by the vaporization of its parent protein and its separation from other ions based on its mass-to-charge ratio. The most common modes of acquiring MS data are 1) full scan acquisition resulting in the typical total ion current plot (TIC), 2) selected ion monitoring (SIM), and 3) selected reaction monitoring (SRM).

In certain embodiments of the methods provided herein, biomarker protein expression levels are measured by LC-SRM-MS. LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio is superior to conventional tandem mass spectrometry (MS/MS) experiments, which select one mass window in the first quadrupole and then measure all generated transitions in the ion detector. LC-SRM-MS.

In certain embodiments, an SRM-MS assay for use in diagnosing or monitoring lung cancer as disclosed herein may utilize one or more peptides and/or peptide transitions derived from the proteins comprising C163A and LG3BP. In certain embodiments, the assay may utilize peptides and/or peptide transitions from 100 or more, 150 or more, 200 or more, 250 or more, 300 or more, 345 or more, or 371 or more biomarker proteins. In certain embodiments, two or more peptides may be utilized per biomarker proteins, and in certain of these embodiments three or more of four or more peptides may be utilized. Similarly, in certain embodiments two or more transitions may be utilized per peptide, and in certain of these embodiments three or more; four or more; or five or more transitions may be utilized per peptide. In one embodiment, an LC-SRM-MS assay for use in diagnosing lung cancer may measure the intensity of five transitions that correspond to selected peptides associated with each biomarker protein. The achievable limit of quantification (LOQ) may be estimated for each peptide according to the observed signal intensities during this analysis.

The expression level of a biomarker protein can be measured using any suitable method known in the art, including but not limited to mass spectrometry (MS), reverse transcriptase-polymerase chain reaction (RT-PCR), microarray, serial analysis of gene expression (SAGE), gene expression analysis by massively parallel signature sequencing (MPSS), immunoassays (e.g., ELISA, and other antibody based methods of detection), immunohistochemistry (IHC), transcriptomics, and proteomics.

In some embodiments, ELISA is used to measure the expression level of a biomarker protein, e.g., C163A and/or LG3BP, an antibody that specifically binds the biomarker protein, C163A and/or LG3BP can be used. For example, a LG3BP antibody described herein (e.g., Table 1B and Table 2B) is used for measuring the expression level of LG3BP; a C163A antibody described herein (e.g., Table 1A and Table 2A) is used for measuring the expression level of C163A. In some embodiments, the method includes contacting a blood sample obtained from the subject with a LG3BP antibody described herein (e.g., Table 1B and Table 2B) and a C163A antibody (e.g., Table 1A and Table 2A) described herein.

To evaluate the diagnostic performance of a particular set of peptide transitions, a ROC curve is generated for each significant transition.

An "ROC curve" (Receiver Operating Characteristic) as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.8, 0.9 to 0.95, or 0.95 to 1.0.

The term "reversal" as used herein refers to a ratio of two proteins in a two-protein classifier.

The term "physician cancer assessment" (pCA) encompasses various estimates that physician's employ to estimate the probability of a nodule being cancer in a subject. For example, pCA can be based on the physician's clinical training and experience, including taking into account the appearance and size of the nodule from CAT scan (CT), a patient's age and smoking history. In some instances, pCA involves the use of equations that using the same factors described above (i.e. appearance and size of nodule, patient's age and smoking history). For example, the National Cancer Institute provides tools for physicians to assess cancer risk (www.cancer.gov/resources-for/hp#rats). While these tools are not developed specifically for lung cancer, some variables present in these assessments are relevant, including, but not limited to, the patient's medical history or family history of cancer, genetic predisposition to cancer, age, race, and lifestyle choices (exposure to carcinogens through smoking or exposure to radiation, diet, health of immune system, access to preventative care and health screenings, etc.).

The methods provided herein are minimally invasive and pose little or no risk of adverse effects. As such, they may be used to diagnose, monitor and provide clinical management of subjects who do not exhibit any symptoms of a lung condition and subjects classified as low risk for developing a lung condition. For example, the methods disclosed herein may be used to diagnose lung cancer in a subject who does not present with a PN and/or has not presented with a PN in the past, but who nonetheless deemed at risk of developing a PN and/or a lung condition. Similarly, the methods disclosed herein may be used as a strictly precautionary measure to diagnose healthy subjects who are classified as low risk for developing a lung condition.

The present invention provides a method of determining the likelihood that a lung condition in a subject is cancer by measuring an abundance of a panel of proteins in a sample obtained from the subject; calculating a probability of cancer score based on the protein measurements and ruling out cancer for the subject if the score) is lower than a pre-determined score, wherein when cancer is ruled out the subject does not receive a treatment protocol. Treatment protocols include for example pulmonary function test (PFT), pulmonary imaging, a biopsy, a surgery, a chemotherapy, a radiotherapy, or any combination thereof. In some embodiments, the imaging is an x-ray, a chest computed tomography (CT) scan, or a positron emission tomography (PET) scan.

In another aspect the invention further provides a method of determining the likelihood of the presence of a lung condition in a subject by measuring an abundance of panel of proteins in a sample obtained from the subject, calculating a probability of cancer score based on the protein measurements and concluding the presence of said lung condition if the score is equal or greater than a pre-determined score. In some embodiments, the methods provided herein may integrate molecular (proteomic) measurements with clinical risk factors. Non-limiting examples include those in the Solitary Pulmonary Nodule (SPN) Malignancy Risk Score (Mayo Clinic Model), the Fleischner Society Guidelines for Incidental Pulmonary Nodules, the Solitary pulmonary nodule malignancy risk in adults (Brock University cancer prediction equation), and the NPS-BIMC (Bayesian Inference Malignancy Calculator), among others. In some such embodiments, it may integrate the relative abundance of two plasma proteins (LG3BP and C163A) with five clinical risk factors (age, smoking status, nodule diameter, nodule spiculation status and nodule location). One of such tests, e.g., the Nodify XL2® test ("XL2"), is discussed herein in detail (see section 3.5). The lung condition is lung cancer such as for example, non-small cell lung cancer (NSCLC). The subject at risk of developing lung cancer.

The subject has or is suspected of having a pulmonary nodule. The pulmonary nodule has a diameter of less than or equal to 3 cm. In one embodiment, the pulmonary nodule has a diameter of about 0.8 cm to 2.0 cm. The subject may have stage IA lung cancer (i.e., the tumor is smaller than 3 cm).

A cancer risk predictor $C_i(k)$ of a molecular risk reversal $R_i$ is determined as as follows $$Ci(k) = \begin{cases} 0, & \text{if } pCA(k) \leq Ti \\ pCA(k), & \text{otherwise} \end{cases}$$

where the decision threshold $T_i$ for the reversal $R_i$ is defined and was the median value of $\{S_i(k)\}$ of patients with nodules no larger than 15 mm.

The biological sample such as for example tissue, blood, plasma, serum, whole blood, urine, saliva, genital secretion, cerebrospinal fluid, sweat and excreta.

In one aspect, the determining the likelihood of cancer is determined by the sensitivity, specificity, negative predictive value or positive predictive value associated with the score. The score determined has a negative predictive value (NPV) is at least about 60%, at least 70% or at least 80%.

The measuring step is performed by selected reaction monitoring mass spectrometry, using a compound that specifically binds the protein being detected or a peptide transition. In one embodiment, the compound that specifically binds to the protein being measured is an antibody or an aptamer.

In specific embodiments, the diagnostic methods disclosed herein are used to rule out a treatment protocol for a subject, measuring the abundance of a panel of proteins in a sample obtained from the subject, calculating a probability of cancer score based on the protein measurements and ruling out the treatment protocol for the subject if the score determined in the sample is lower than a pre-determined score.

In some embodiments, the panel comprises peptides and proteins of LG3BP and C163A.

In some embodiments, if cancer is ruled out, there is a period of watchful waiting. Watchful waiting can include periodic follow examination to assess whether the pulmonary nodule has changed characteristics. The follow up examination can include for example a blood assay, an x-ray, a pulmonary function test, or a CT scan.

In certain embodiments, the diagnostic methods disclosed herein can be used in combination with other clinical assessment methods, including for example various radiographic and/or invasive methods. Similarly, in certain embodiments, the diagnostic methods disclosed herein can be used to identify candidates for other clinical assessment methods, or to assess the likelihood that a subject will benefit from other clinical assessment methods.

The high abundance of certain proteins in a biological sample such as plasma or serum can hinder the ability to assay a protein of interest, particularly where the protein of interest is expressed at relatively low concentrations. Several methods are available to circumvent this issue, including enrichment, separation, and depletion. Enrichment uses an affinity agent to extract proteins from the sample by class, e.g., removal of glycosylated proteins by glycocapture. Separation uses methods such as gel electrophoresis or isoelectric focusing to divide the sample into multiple fractions that largely do not overlap in protein content. Depletion typically uses affinity columns to remove the most abundant proteins in blood, such as albumin, by utilizing advanced technologies such as IgY14/Supermix (SigmaSt. Louis, Mo.) that enable the removal of the majority of the most abundant proteins.

In certain embodiments of the methods provided herein, a biological sample may be subjected to enrichment, separation, and/or depletion prior to assaying biomarker or putative biomarker protein expression levels. In certain of these embodiments, blood proteins may be initially processed by a glycocapture method, which enriches for glycosylated proteins, allowing quantification assays to detect proteins in the high pg/ml to low ng/ml concentration range. Exemplary methods of glycocapture are well known in the art (see, e.g., U.S. Pat. No. 7,183,188; U.S. Patent Appl. Publ. No. 2007/0099251; U.S. Patent Appl. Publ. No. 2007/0202539; U.S. Patent Appl. Publ. No. 2007/0269895; and U.S. Patent Appl. Publ. No. 2010/0279382). In other embodiments, blood proteins may be initially processed by a protein depletion method, which allows for detection of commonly obscured biomarkers in samples by removing abundant proteins. In one such embodiment, the protein depletion method is a Supermix (Sigma) depletion method.

In certain embodiments, a biomarker protein panel comprises two to 100 biomarker proteins. In certain of these embodiments, the panel comprises 2 to 5, 6 to 10, 11 to 15, 16 to 20, 21-25, 5 to 25, 26 to 30, 31 to 40, 41 to 50, 25 to 50, 51 to 75, 76 to 100, biomarker proteins. In certain embodiments, a biomarker protein panel comprises at least two biomarker proteins C163A and LG3BP.

In certain embodiments of the methods, compositions, and kits provided herein, a biomarker protein may be a protein that exhibits differential expression in conjunction with lung cancer. For example, in certain embodiments a biomarker protein may be C163A or LG3BP.

In other embodiments, the diagnosis methods disclosed herein may be used to distinguish between two different lung conditions. For example, the methods may be used to classify a lung condition as malignant lung cancer versus benign lung cancer, NSCLC versus SCLC, or lung cancer versus non-cancer condition (e.g., inflammatory condition).

In certain embodiments, kits are provided for diagnosing a lung condition in a subject. These kits are used to detect expression levels of one or more biomarker proteins including C163A and/or LG3BP. Optionally, a kit may comprise instructions for use in the form of a label or a separate insert. The kits can contain antibodies described herein (e.g., Tables 1A-1B and 2A-2B) that specifically bind to C163A or LG3BP. The kits can also contain reagents that specifically bind to mRNA expressing C163A or LG3BP. These reagents can include nucleotide probes. The kits can also include reagents for the detection of reagents that specifically bind to C163A or LG3BP (e.g., secondary antibody or detection antibody). These reagents can include fluorophores.

In specific embodiments, antibodies described herein are used in Nodify XL2® assay described below. Additional description can be found in WO12019/079635 and WO/2017/192965, the content of each of which is incorporated by reference herein in its entirety.

Nodify XL2® Testing

1. Introduction

XL1 has been developed to differentiate benign from malignant lung nodules. XL1 is a blood test for proteins that combines expertise in proteomics and computer science using large data sets. Mass spectrometry has been employed as a technology for molecular diagnostics for decades and recent advances in instrumentation allows measurement of hundreds of proteins at a time [X.-J. Li, C. Hayward, P.-Y. Fong, M. Dominguez, S. W. Hunsucker, L. W. Lee, M. McLean, S. Law, H. Butler, M. Schirm, 0. Gingras, J. Lamontagne, R. Allard, D. Chelsky, N. D. Price, S. Lam, P. P. Massion, H. Pass, W. N. Rom, A. Vachani, K. C. Fang, L. Hood and P. Kearney, "A Blood-Based Proteomic Classifier for the Molecular Characterization of Pulmonary Nodules," *Science Translational Medicine*, vol. 5, no. 207, p. 207ra142, 2013]. Cancers secrete and shed proteins that are different from normal cells and some of these proteins circulate in the blood. 388 protein candidates and blood samples stored from both patients with benign and malignant lung nodules were analyzed. The initial analyses discovered and validated a predictor for benign nodules using a combination of 11 proteins [A. Vachani, H. I. Pass, W. N. Rom, D. E. Medthun, E. S. Edell, M. Laviolette, X.-J. Li, P.-Y. Fong, S. W. Hunsucker, C. Hayward, P. J. Mazzone, D. K. Madtes, Y. E. Miller, M. G. Walker, J. Shi, P. Kearney, K. C. Fang and P. P. Massion, "Validation of a Multiprotein Plasma Classifier to Identify Benign Lung Nodules," *Journal of Thoracic Oncology*, vol. 10, no. 4, pp. 629-637, 2015].

XL1 provided significant performance over clinical risk factors physicians use to differentiate benign from malignant lung nodules. Further work with protocol-collected blood samples to refine a second version of the Nodify XL2® test has now completed which is a robust test for determining which nodules are benign.

This new version, the Nodify XL2® test, improves on XL1 in four ways as described in Section 3.7. These are: 1) a refined intended use population; 2) the identification of 2 of the prior 11 proteins that are most accurate in identifying benign lung nodules; 3) the incorporation of five clinical risk factors; and 4) discovery and validation based on two large prospective studies where samples were collected using a uniform protocol rather than archival biobanks.

The Nodify XL2® test achieves high performance for identifying benign nodules. At a 98% negative predictive value (NPV), the sensitivity is 97% (Table 8, Section 3.6). This improved test performs significantly better than PET (NPV of 79% (CI:66%-88%)(Section 3.3.3.3.). The Nodify XL2® test also performs significantly better than four clinical risk predictors (Mayo, VA, Brock and Herder) (Section 3.3.3.2.). Nodify XL2® testing will provide physicians the best available evidence to determine which nodules are benign.

Nodify XL2® testing will be positioned before PET, bronchoscopy, needle biopsy, and surgery (Section 2.4.2). The confidence from the high NPV values with the Nodify XL2® test will guide more patients with benign nodules into CT surveillance. That will achieve the goal of Nodify XL2®: avoid unnecessary further evaluation of benign nodules, especially invasive procedures.

The projected clinical utility of Nodify XL2® testing is a 36% reduction of invasive procedures (Section 2.4.1). These reductions in invasive procedures will reduce surgeries, surgical mortality, and hospitalizations from biopsy complications (Section 2.4.3).

2. Clinical Aspects of the Nodify XL2® Test and Lung Nodules 2.1 Nodify XL2® Test Intended Use and Description 2.1.1 Intended Use The Nodify XL2® test is intended for the evaluation of 8-30 mm lung nodules in patients 40 years or older where the physician estimates a lower cancer risk (pretest probability of cancer is 0 to 50%). The goal for Nodify XL2® testing is to identify those nodules that are likely benign so those nodules can be safely observed by CT surveillance rather than undergo costly and risky invasive procedures such as biopsy and surgery.

2.1.2 Description of the Nodify XL2® Test

The Nodify XL2® test is a risk predictor that integrates molecular (proteomic) measurements with clinical risk factors. Proteins associated with cancers or benign processes are measured. These proteins are secreted or shed from cells in the lung and measured in a blood plasma sample. The Nodify XL2® result will be reported as Likely Benign (90-98% negative predictive value) or Indeterminate (post-test cancer risk not significantly lower than the pre-test risk of cancer). For details see Section 3.6.

2.2 The Unmet Need for Lung Nodules is Significant and Growing 2.2.1 Lung Nodules 2.2.1.1 Definitions Lung nodules are rounded densities seen by x-ray imaging. X-ray imaging can be a chest radiograph (CXR) or computer-assisted tomography (CAT scan). Nodules are mostly surrounded by lung tissue and are also called coin lesions, solitary pulmonary nodules or lesions, or a "spot" on the lung. Rounded densities larger than 30 mm in diameter are lung masses, not nodules. The edges of the nodules can be described as smooth or irregular (stellate or spiculated), and irregular edges somewhat more indicative for cancer. Heavily calcified nodules with smooth edges are generally benign and solid nodules that have not shown growth over time are considered benign. With improved CT imaging subsolid nodules, ground-glass opacities or part-solid nodules, are now seen and have different guidelines. The focus of this application is 8-30 mm solid nodules and not subsolid nodules.

For a comprehensive review of nodules and their evaluation see the 2-part series by Patel, et al. [V. K. Patel, S. K. Naik, D. P. Naidich, W. D. Travis, J. A. Weingarten, R. Lazzaro, D. D. Gutterman, C. Wentowski, H. B. Grosu and S. Raoof, "A Practical Algorithmic Approach to the Diagnosis and Management of Solitary Pulmonary Nodules. Part 1: Radiologic Characteristics and Imaging Modalities," Chest, vol. 143, no. 3, pp. 825-339, 2013; V. K. Patel, S. K. Naik, D. P. Naidich, W. D. Travis, J. A. Weingarten, R. Lazzaro, D. D. Gutterman, C. Wentowski, H. B. Grosu and S. Raoof, "A Practical Algorithmic Approach to the Diagnosis and Management of Solitary Pulmonary Nodules. Part 2: Pretest Probabiity and Algorithm," Chest, vol. 143, no. 3, pp. 840-846, 2013].

2.2.1.2 Numbers of Nodules Detected Annually

The estimated number of new lung nodules detected annually in the US is 1.57 million [M. K. Gould, T. Tang, I.-L. A. Liu, J. Lee, C. Zheng, K. N. Danforth, A. E. Kosco, J. L. Di Fiore and D. E. Suh, "Recent Trends in the Identification of Incidental Pulmonary Nodules," American Journal of Respiratory and Critical Care Medicine, vol. 192, no. 10, pp. 1208-1214, The number of new lung nodules has been increasing due to a combination of factors including CT scan technology improvements and more CT scans being done. The 1.57 million estimate is for nodules that are 4-30 mm diameter; the estimate for 8-30 mm nodules is 800,000 per year.

2.2.1.3 Incidental and Screen-detected Nodules

The above estimate of 1.57 million nodules per year is only for incidentally found nodules and does not include another 1.5 million screen-detected nodules. Incidental means the imaging was done for reasons other than nodule detection. For example, imaging of the heart, upper abdomen, and even mammography includes lung tissue so a lung nodule is an incidental finding.

Lung cancer screening now has coverage in the United States. As of Apr. 26, 2016 there were 806 sites registered for screening (www.acr.org/quality-safety/national-radiology-data-registry/lung-cancer-screening-registry—see Core Documents, accessed Jun. 20, 2016). Initial estimates are that another 1.5 million nodules per year will be found once screening programs are in place. The National Lung Screening Trial (NSLT) had a screen positive rate of 24% and estimated there are 7 million persons in the United States that meet NSLT enrollment criteria [The National Lung Screening Trial Research Team, "Reduced Lung-Cancer Mortality with Low-Dose Computed Tomographic Screening," The New England Journal of Medicine, vol. 365, pp. 395-409, 2011].

2.2.1.4 Lung Nodule "Epidemic" and Health Care

Early detection of lung nodules is a great opportunity to reduce lung cancer mortality but it comes with significant risks. These risks are both for patients and health care delivery. For patients a major problem is the risk of unnecessary invasive procedures to find the minority of nodules that are cancer. Nodify XL2® testing addresses these avoidable procedures.

For health care delivery, the risks are both costs and overloading the health care system. The majority of patients with nodules will be over 65 years of age. In the NLST, over 57% of enrollees in the NSLT were over 65 years of age. Also the rates of nodule detection increased dramatically with age, at least until age 89. So Medicare enrollees are more likely to meet lung cancer screening criteria and have more nodules detected. If the nodules are ≥8 mm, then further testing is indicated, Nodify XL2® testing addresses these avoidable procedures.

2.2.1.5 Relevance to Medicare Population

Of the expected 3 million nodules per year found incidentally or by lung cancer screening, the majority will be Medicare age. Four recent studies underscore the importance of lung cancer evaluations to the Medicare population:

The mean age of 377 eligible patients in an 18 site retrospective chart review study was 65 [M. T. Tanner, J. Aggarwal, M. K. Gould, P. Kearney, G. Diette, A. Vachini, K. C. Fang and G. A. Silvestri, "Management of Pulmonary Nodules by Community Pulmonologists. A Multicenter Observational Study," *Chest*, vol. 148, no. 6, pp. 1405-1414, 2015]. All patients had nodules 8-20 mm in diameter.

A prospective study across 12 sites and 475 patients found 62.5% of patients were 65 years of age or older [A. Vachani, Z. Hammoud, S. Springmeyer, N. Cohen, D. Nguyen, C. Williamson, S. Starnes, S. Hunsucker, S. Law, X.-J. Li, A. Porter and P. Kearney, "Clinical Utility of a Plasma Protein Classifier for Indeterminate Lung Nodules," *Lung*, vol. 193, no. 6, pp. 1023-1027, 2015]. All patients had nodules 8-30 mm in diameter.

Over 50% of patients in a prospective study across 33 sites and 685 patients were 65 years of age or older (PANOPTIC Study). All patients had nodules 8-30 mm in diameter.

A recent study reported that between Jan 2009 and Dec 2011, 8,979 Medicare patients from a random sampling of 5% of Medicare claims, underwent lung cancer evaluations because of an abnormal chest CT scan [T. Lokhandwala, M. A. Bittoni, R. A. Dann, A. O . D'Souza, M. Johnson, R. J. Nagy, R. B. Lanman, R. E. Merritt and D. P. Carbone, "Costs of Diagnostic Assessment for Lung Cancer: A Medicare Claims Analysis," *Clinical Lung Cancer*, 2016].

2.2.2 Lung Nodule Evaluation: Current Practice and Need for Improvement 2.2.2.1 Guidelines Groups have published guidelines for the evaluation of lung nodules [H. MacMahon, J. H. Austin, G. Gamsu, C. J. Herold, J. R. Jett, D. P. Naidich, E. F. Patz and S. J. Swensen, "Guidelines for Management of Small Pulmonary Nodules Detected on CT Scans: A Statement from the Fleischner Society," *Radiology*, vol. 237, no. 2, pp. 395-400, 2005; M. K. Gould, J. Donington, W. R. Lynch, P. J. Mazzone, D. E. Midthun, D. P. Naidich and R. S. Wiener, "Evaluation of Individuals With Pulmonary Nodules: When Is It Lung Cancer?: Diagnosis and Management of Lung Cancer, 3rd ed: American Cllege of Chest Physicians Evidence-Based Clinical Practice Guidelines," *Chest*, vol. 143, no. 5_suppl, pp. e935-e1205, 2013; M. E. Callister, D. R. Baldwin, A. R. Akram, S. Barnard, P. Cane, J. Draffan, K. Franks, F. Gleeson, R. Graham, P. Malhotra, M. Prokop, K. Rodger, M. Subesinghe, D. Waller and I. Woolhouse, "British Thoracic Society Guidelines For the Investigation and Management of Pulmonary Nodules," *Thorax*, vol. 70, no. Suppl 2, pp. iil-ii54, 2015]. A set of guidelines regarding lung cancer is published and updated by the American College of Chest Physicians (ACCP). The ACCP guidelines for lung nodules, updated in 2013, are the primary reference used by pulmonologists in the United States. It is important to focus on ACCP section 4.0 for >8 mm nodules, the intended use for the Nodify XL2® test.

2.2.2.2 General Approach to 8-30 mm "Indeterminant" Nodules

Nodules are found with imaging other than chest CT scans (Section 2.2.1.3). Thus a chest CT with high-resolution imaging of the nodule is often needed. The CT findings alone or prior images may indicate a nodule is benign. The details of imaging and differential diagnosis of nodules has been reviewed by Patel and colleagues. When CT imaging alone is not definitive, the nodule is described as "indeterminant".

CT imaging accuracy was studied using expert reviewers in a retrospective study of 344 nodules before any nodules were determined to be benign [J. W. Fletcher, S. M. Kymes, M. Gould, N. Alzraki, R. E. Coleman, V. J. Lowe, C. Marn, G. Segall, L. A. Thet and K. Lee, "A Comparison of the Diagnostic Accuracy of {18]F-FDG PET and CT in the Characterization of Solitary Pulmonary Nodules," *Journal of Nuclear Medicine*, vol. 49, pp. 179-185, 2008.]. CT results (after excluding 128 [27%] without a "reference standard" or an "inconclusive result") showed a sensitivity of 95.6% (95% CI, 91.3%-97.9%), and a specificity of 40.6% (95% CI, 33.0%-48.7%). The results with CT interpretation of indeterminate nodules with general radiologists will be expected to be inferior.

Most 8-30 mm nodules are indeterminant. The ACCP Guidelines state: "Although clinical and radiographic [CT scans] characteristics cannot reliably distinguish between benign and malignant nodules in most individuals, it is nevertheless important to estimate the clinical probability of malignancy before ordering imaging tests or biopsy procedures". The pretest probability of malignancy (pCA) is estimated by using clinical judgment or with a quantitative risk model (see Section 2.2.4). Establishing a pCA creates three groupings (excluding patients at high surgical risk), Low, Intermediate, and High probability. The exact numbers changed between guideline revisions but are similar, with <5% pCA being Low and >65% pCA being High. The general concept is that Low risk patients will be observed with further CT surveillance to watch for growth if a nodule is malignant.

Conversely, the guidelines suggest those patients in the High risk group go directly to surgery. The logic is that the probability of cancer is high enough that a negative biopsy will not change the care pathway.

The Intermediate risk group (5-65% pCA) are recommended to enter the diagnostic odyssey with PET scanning often the next step. A negative PET suggests a benign nodule, so the patient is followed with CT scans. A positive PET scan goes on to surgery or biopsy. This is the overall concept, but PET has sensitivity and specificity problems as discussed in Sections 2.2.6.

2.2.2.3 The Problems with Guidelines and Current Practice

The guidelines are conceptually good, but are based on mostly weak evidence and there is evidence that they are not followed.

The guidelines are based on weak evidence. The ACCP guidelines use the GRADE system and most recommendations regarding>8 mm nodules are 2C, a weak recommendation with low quality evidence. There are 3 recommendations that are level 1C, a strong recommendation with low quality evidence, which are: soliciting patient preference, going to further evaluation if there's evidence of malignant growth, and a preference for thorascopic rather than open biopsy.

There is abundant evidence that suggest the guidelines are not followed [D. R. Baldwin, "Development of Guidelines for the Management of Pulmonary Nodules: Toward Better Implementation," Chest, vol. 148, no. 6, pp. 1365-1367, 2015; R. S. Wiener, M. K. Gould, C. G. Slatore, B. G. Fincke, L. M. Schwartz and S. Woloshin, "Resource Use and Guideline Concordance in Evaluation of Pulmonary Nodules for Cancer: Too Much and Too Little Care," JAMA Internal Medicine, vol. 174, no. 6, pp. 871-880, 2014]. A retrospective cohort study of 15 Veterans hospitals and 300 patients found that only 45% of the patient care for nodules was in concordance with guidelines. A pulmonary community practice observational record review of 18 practices and 377 patients found a wide variation in management of nodules. The surgery for benign nodules rate was 35% and the rate of surgery was the same for Low, Intermediate and High risk patients. The risk categories were calculated by the study and despite a Low risk, 28% had biopsies and 17% had surgery. Furthermore, the rate of malignant nodules observed with CT surveillance was 24.5%, resulting in a risk of delayed diagnosis.

The rates of surgery for benign nodules range between 10% and 55% as summarized by Vachani, et al. in their publication of a survey from 196 pulmonologists that supports the potential of a non-invasive biomarker to strongly and independently affect management decisions [A. Vachani, N. T. Tanner, J. Aggarwal, C. Mathews, P. Kearney, K. C. Fang, G. Silvestri and G. B. Diette, "Factors That Influence Physician Decision Making for Indeterminate Pulmonary Nodules," Annals of the American Thoracic Society, vol. 11, no. 10, pp. 1586-1591, High rates of surgery for benign nodules are problematic because of the morbidity and mortality associated with surgery. Surgical risk figures are dependent on the population and the procedures used. The surgical mortality estimate after lobectomy in a Medicare age patient is 2-3% (Section 2.4.3.2).

Therefore, there is a clear opportunity for improvement in current practice. The rates of avoidable surgery for benign nodules was 35% in community practices and reported as high as 55%. The high rates for avoidable PET scans, biopsies, and surgeries are addressed in Sections 2.4.1.3, 2.4.3.1, and 2.4.3.2 respectively.

2.2.3 Physician Pretest Probability of Cancer (pCA), Lower Cancer Risk Group and the Unmet Need The guidelines recommend a determination of the pretest probability of malignancy (pCA) by clinical judgment or with a model such as the Mayo equation [S. J. Swensen, M. D. Silverstein, D. M. Ilstrup, C. D. Schleck and E. S. Edell, "The Probbility of Malignancy in Solitary Pulmonary Nodules. Application to Small Radiologically Indeterminate Nodules," Archives of Internal Medicine, vol. 157, no. 8, pp. 849-855, 1997; S. J. Swensen, M. D. Silverstein, E. S. Edell, V. F. Trastek, G. L. Aughenbaugh, D. M. Ilstrup and C. D. Schleck, "Solitary Pulmonary Nodules: Clinical Prediction Model Versus Physicians," Mayo Clinic Proceedings, vol. 74, no. 4, pp. 319-329, 1999]. Pulmonologists uniformly used their clinical judgment for assigning pCA [R. S. Wiener, C. G. Slatore, C. Gillespie and J. A. Clark, "Pulmonologists' Reported Use of Guidelines and Shared Decision-making in Evaluation of Pulmonary Nodules: A Qualitative Study," Chest, vol. 148, no. 6, pp. 1415-1421, 2015], and other physicians do not determine a pCA [S. E. Golden, R. S. Wiener, D. Sullivan, L. Ganzini and C. G. Slatore, "Primary Care Providers and a System Problem: A Qualitative Study of Clinicians Caring for Patients With Incidental Pulmonary Nodules," Chest, vol. 148, no. 6, pp. 1422-1429, 2015].

The PANOPTIC trial (Section 2.3) collected pCA results upon clinical presentation, after a CT scan, and before other testing. The physicians in the study used their clinical judgment 80% of the time and were significantly better than the two quantitative risk models used most often, the VA [M. K. Gould, L. Ananth and P. G. Barnett, "A Clinical Model to Estimate the Pretest Probability of Lung Cancer in Patients with Solitary Pulmonary Nodules," Chest, vol. 131, no. 2, pp. 383-388, 2007] and Mayo, (AUC 0.85 vs 0.75 (VA) p<0.001 and vs 0.78 (Mayo) p=0.011). This indicates that physician pCA is best for separation of patients with nodules into higher and lower cancer risk groups such as a pCA of 50% or less risk of cancer (the intended use group for the Nodify XL2® test).

Further analyses of physician pCA data elucidates the need for Nodify XL2® testing. Physicians are good at placing most cancerous nodules into pCA greater than 50% and most benign nodules into pCA of 50% or less. However, most benign nodules are not in the Low risk (0-5% pCA) category where CT surveillance is recommended. Most benign nodules are in the Intermediate risk category where further evaluation is recommended. These evaluations lead to many benign nodules undergoing risky and expensive procedures. In PANOPTIC, the 33 research sites were nearly all academic centers and integrated health networks yet the rates for surgery on benign nodules was 18% and biopsy of benign nodules was 30%. The comparable figures for community pulmonary practices (where most patients receive their care) are 35% of surgeries were performed on benign nodules and 62% of biopsies were performed on benign nodules.

Therefore, the unmet need is to provide the treating physician with a test for a Lower Risk nodule (pCA of 50% or less). This test should have a high Negative Predictive Value (NPV) result for a benign nodule. The post-test result then indicates the nodule is Low risk (0-5% pCA) and CT surveillance is recommended.

2.2.3.1 Physician pCA for Lower Risk Patients

Physicians were quite good establishing risk for all nodules (the entire risk population) with an AUC of 85%. However, they were not as good with lower risk (pCA 50% or less) patients (n=178 with 29 cancer and 149 benign nodules). In those lower risk patients, the physician AUC is 0.69 and is shown in Section 3.3.4.1.

Most of these benign nodules are within the Intermediate risk population where the guidelines recommend further evaluation. If the guidelines are followed, most of those 149 patients with benign nodules will undergo avoidable imaging and biopsy. This underscores the need for Nodify XL2® testing and is discussed further in Sections 2.4 and 3.4 on Clinical Utility.

2.2.4 Quantitative Cancer Risk Models

The PANOPTIC results show that physicians are better than quantitative models at assigning pretest probability of cancer risk (pCA). The major factor for cancer risk in a pulmonary nodule is size. It was shown that the increasing prevalence of cancer associated with size. Other major factors are smoking history and age. Since CT screening is just being implemented in the United States, most risk models were developed for incidental nodules rather than screen detected nodules.

2.2.4.1 Incidental Nodule Models

The Mayo Clinic and a Veterans Administration (VA) Hospital group have developed prediction models that are based on similar but not identical factors. The prevalence of cancer in the VA model is considerably higher so it performs differently. These and other models have been summarized in the ACCP 2013 guidelines with support given to the Mayo model. The first sentence in Section 4.1 of the Guidelines reads: "Although clinical and radiographic characteristics cannot reliably distinguish between benign and malignant nodules in most individuals, it is nevertheless important to estimate the clinical probability of malignancy before ordering tests or biopsy procedures."

2.2.4.2 Screen-Detected Nodules

Using two Canadian lung cancer screening trials, McWilliams published a set of quantitative equations with AUC>0.90 [A. McWilliams, M. C. Tammemagi, J. R. Mayo, H. Roberts, G. Liu, K. Soghrati, K. Yasufuku, S. Martel, F. Laberge, M. Gingras, S. Atkar-Khattra, C. D. Berg, K. Evans, R. Finley, J. Yee, J. English, P. Nasute, J. Goffin, S. Puksa, L. Stewart, S. Tsai, M. R. Johnston, D. Manos, G. Nicholas, G. D. Goss, J. M. Seely, K. Amjadi, A. Tremblay, P. Burrowes, P. MacEachern, R. Bhatia, M.-S. Tsao and S. Lam, "Probability of Cancer in Pulmonary Nodules Detected on First Screening CT," The New England Journal of Medicine, vol. 369, no. 10, pp. 910-919, 2013]. The equations are available through Brock University. The combined data includes 2,961 patients, but only 144 (<5%) of the nodules were malignant. They included subsolid nodules, but 79% were solid. The mean nodule size was 4.1 mm and median was 3.4 mm consistent with a low proportion of cancers. Predictors of cancer in the model included older age, female sex, family history of lung cancer, emphysema, larger nodule size, location of the nodule in the upper lobe, part-solid nodule type, lower nodule count, and speculation.

The McWilliams paper recommends their equations be used for nodules from a baseline screening, low-dose CT scan (rather than incidentally found nodules).

2.2.5 Guidelines for Radiologists and CT Scan Nodule Reporting; Lung-RADS and Fleishner There are guidelines for radiologists regarding reporting lung nodules and the intervals for follow-up imaging. The guidelines for incidental nodules<8 mm come from the Fleishner Society. Fleishner guidelines were developed for incidentally found nodules.

Guidance from the American College of Radiology for lung cancer screening programs is Lung-RADS (www.acr.org/Quality-Safety/Resources/LungRADS). Lung-RADS was developed to improve reporting and management recommendations to clinicians. One goal was to reduce the number of false positive reports needing further evaluation without increasing the false negatives. Based on the literature, they changed the size of nodules considered "positive" to 6 mm from 4 mm as used in the NLST. Another goal for Lung-RADS is a structured reporting system for lung cancer screening programs based on nodule size, CT imaging density, and whether the nodule was present at baseline, enlarging, or new at follow-up. Lung-RADS does not include other clinical factors that clinicians use such as smoking history, age, nodule location, or exposures (e.g. asbestos).

2.2.6 PET Scans

Positron Emission Tomography with contrast agents (PET) is useful in lung cancer staging, but PET has significant limitations for the diagnosis of lung nodules. These limitations are a lack of sensitivity, especially for smaller nodules, non-standardized reading and reporting, and false positive scans for inflammatory and infectious nodules.

2.2.6.1 PET sensitivity. Smaller nodules are difficult to image and PET was initially limited to nodules>10 mm. Small nodules and low-uptake of contrast in low-metabolic malignancies are major limits to sensitivity for PET imaging. The initial sensitivities reported from single-center experience with PET were estimated to be 95%. The estimate dropped to 87% when reviewed by the ACCP in 2007. Current estimates range from 72% to 94% and are reviewed in the 2013 ACCP Guidelines in section 4.2.3. A 2014 meta-analysis reports a pooled sensitivity of 89% (95% CI, 86%-91%) and high heterogeneity when areas of infectious lung disease are included [S. A. Deppen, J. D. Blume, C. D. Kensinger, A. M. Morgan, M. C. Aldrich, P. P. Massion, R. C. Walker, M. L. McPheeters, J. B. Putnam and E. L. Grogan, "Accuracy of FDG-PET to Diagnose Lung Cancer in Areas With Infectious Lung Disease. A Meta-analysis," JAMA, vol. 312, no. 12, pp. 1227-1236, 2014].

Early publications of PET about nodules were encouraging such that the 2007 ACCP guidelines gave PET an evidence Grade of 2A, but concerns about the quality of evidence and risk of bias decreased the recommendation to Grade 2C [V. S. Nair, V. Sundaram, M. K. Gould and M. Desai, "Utilization of [18F] FDG PET Imaging in the National Lung Screening Trial," Chest, 2016]. The review articles by Patel initially state that PET is "very accurate" but after a summary of more recent data they emphasize the shortcomings of PET, and add a limitation that PET is best suited for nodules with an "intermediate" pCA. A recent study using NLST data showed PET use for nodules was 11% of 14,195 patients, but there was still inappropriate PET use in 21% of cases which suggested overutilization with small nodules and concern about contributing to excess healthcare costs.

Recently PET has been combined with CT to improve resolution so the size limitation has been re-stated to 8-10 mm. The combination is anticipated to improve the results but with increased cost and much higher radiation exposure (Section 2.2.6.4)

2.2.6.2 The reporting of PET has variation and is often only reported subjectively. Since the isotope in the contrast agent degrades (~110 min half-life for fluorine-18), the dose administered to a patient depends on the proximity in time to when the isotope was created. So the degree of a positive or negative PET depends on comparison of uptake in a normal high metabolic area with the area in question. This comparison is often just reported subjectively but can measured. A measured value, the Standard Uptake Value (SUV) is produced. A SUV value greater than 2.5 is considered positive. Some publications, such as Herder [G. J. Herder, H. van Tinteren, R. P. Golding, P. J. Kostense, E. F. Comans, E. F. Smit and 0. S. Hoekstra, "Clinical Prediction Model to Characterize Pulmonary Nodules: Validation and Added Value of 18F-Fluorodeoxyglucose Positron Emission Tomography," Chest, vol. 128, no. 4, pp. 2490-2496, only reported subjective results on a four-point descriptive scale, without SUV values. Subsequent publications must guess at a similar scale using SUV values. For example, one of these publications (Al-Ameri) [A. Al-Ameri, P. Malhotra, H. Thygesen, P. K. Plant, S. Vaidyanathan, S. Karthik, A. Scarsbrook and M. E. Callister, "Risk of Malignancy in Pulmonary Nodules: A Validation Study of Four Prediction Models," Lung Cancer, vol. 89, no. 1, pp. 27-30, used a 3 division scale of SUV with good results. However, this paper did not report mean or median sizes of nodules nor numbers of nodules evaluated in their 139 patients with PET scans. Of the total of 244 patients, they report that 188 had a solitary nodule (presumably the remainder had multiple nodules), and the largest nodule was <10 mm in 103 patients and PET sensitivity was not addressed in the study which appears to have a lot of smaller nodules. Consequently, it is difficult to derive conclusions or compare to other studies where basic nodule characteristics (such as nodule size) are disclosed.

So these example publications, Herder and Al-Ameri, highlight the lack of standardization across sites and physicians in PET interpretation and reporting.

2.2.6.3 False positive scans for nodules are an additional problem. The Tanner chart review of community practices found a false positive PET scan rate of 39%. Also notable is that a PET scan was performed in 37% of patients and was associated with increased intensity of biopsy and surgery compared to surveillance (P<0.0001).

Deppen reported a meta-analysis which included endemic areas for infectious lung disease. Besides extreme heterogeneity regarding accuracy for diagnosis of lung nodules, the specificity in endemic regions was only 61% compared to 77% in nonendemic regions. They concluded their data did not support the use of FDP-PET to diagnose lung cancer in endemic regions. These endemic regions in the United States include the Mississippi, Ohio, and Missouri river valley regions along with the southwestern United States including the Central Valley of California.

2.2.6.4 PET is non-invasive but not risk free. The radiation dose from PET alone is significant at 14 mSv. When combined with CT, as is now usual, the dose increases to 24 mSv. For comparison, a low-dose CT for screening is 1.4 mSv.

2.3. *Clinical Research to Support the Nodify* XL2® *Test*

2.3.1 Discovery, Verification, and Validation of XL1

The initial discovery for XL1 started with 388 candidate proteins and an assay was developed for 371 of them. The first samples were frozen plasma from 3 sites (n=143) and 36 cooperative proteins were identified for a classifier. Verification was with 13 proteins from 4 sites (n=104) and along with discovery work was published in Science Translational Medicine in 2013. At this time, it was determined that this systems biology and proteomics approach was most suited for excluding malignancy in nodules between 8 and 30 mm in size. Validation for XL1 was done with 11 proteins, of which 5 were diagnostic and 6 were used for normalization, with new archival samples from 4 sites (n=141) and published in the Journal of Thoracic Oncology in 2015.

2.3.2 Survey and Chart Review

Boston Healthcare was contracted for a survey of pulmonary physicians to determine their practice patterns and potential acceptance of a biomarker for pulmonary nodules. The need and acceptance was confirmed and published in 2014.

Boston Healthcare also collected data for a comprehensive chart review of community pulmonary practices to understand practice patterns where most of pulmonary nodules are managed. Nodule management of 377 patients from 18 geographically diverse sites were assessed. The results have been presented at national meetings and published in 2015. Of particular note was finding that benign nodules had a 61% biopsy and 35% surgery rate.

2.3.3 Analytic Validation

Analytic validation has been performed and published in 2015 [X.-J. Li, L. W. Lee, C. Hayward, M.-Y. Brusniak, P.-Y. Fong, M. McLean, J. Mulligan, D. Spicer, K. C. Fang, S. W. Hunsucker and P. Kearney, "An Integrated Quantification Method to Increase the Precision, Rocustness, and Resolution of Protein Measurement in Human Plasma Samples," *Clinical Proteomics*, vol. 12, no. 3, 2015].

2.3.4 Clinical Utility and Discovery/Verification of the Nodify XL2® Test

Study 1013 is a prospective study started in 2012 and enrolled 475 patients from 12 sites. This study was unique since it included patients who were undergoing procedures to determine if a lung nodule is benign or cancerous. Therefore a tissue diagnosis was available and a potential change in the use of invasive procedures could be assessed if XL1 would have been used. The main finding was a 32% decrease if XL1 result was followed, but 24% of malignant nodules would have been routed to CT surveillance.

Study 1013 results were also used for the discovery of the Nodify XL2® Test (Section 3.1).

2.3.5 PANOPTIC and Nodify XL2® Validation Study 1001 (PANOPTIC) was also started in 2012 and enrolled 685 patients from 33 sites. This study included all intended use nodules before any diagnostic testing had been initiated. The study is unique because physician pretest probability of cancer (pCA) was collected. Data was used to validate Nodify XL2® (Section 3.1) and present the performance and comparison data in this document.

2.4 Clinical Utility, Anticipated Clinical Use of Nodify XL2® testing, and Nodify XL2® Impact on Invasive Procedures 2.4.1 Clinical Utility The Nodify XL2® test is robust and used for determining which lower risk nodules are benign. The clinical need that Nodify XL2® testing addresses is to appropriately place more patients with benign nodules into CT surveillance. This will avoid unnecessary imaging and invasive procedures which is the primary clinical utility goal for Nodify XL2® testing. Results from the PANOPTIC trial can be used to estimate the effect of Nodify XL2® test results at many Negative Predictive Values (NPV) (Table 8, Section 3.6). Here the 98% NPV values were used and the clinical context was discussed. The 98% NPV was used as the majority of likely benign reports have a NPV of 98% (Table 8, Section 3.6).

2.4.1.1 Clinical Utility at 98% NPV

At a NPV of 98%, the sensitivity of the Nodify XL2® test is 97%, with a specificity of 44% (Table 4, Section 3.2). If the Nodify XL2® test was used in all lower risk nodules (n=178), the reduction of invasive procedures in PANOPTIC on benign nodules would be 36% (15 of 42) (Section 3.4).

The number of patients tested would be 178 patients, 69 (39%) would receive a "Likely Benign" test result with a 98% probability (NPV) of being benign. That very high NPV would likely lead to CT surveillance alone.

There were 29 malignant nodules in the lower risk group and 13 of 29 (45%) were routed to CT surveillance by the clinicians. The use of the Nodify XL2® test at the 98% NPV level, would route 1 patient (3%) to CT surveillance (Table 7, Section 3.4).

2.4.1.2 Clinical Utility and PET Scans

At the 98% NPV level, 21 of 56 (36%) of PET scans that were obtained in patients with benign nodules would have been avoided with the use of the Nodify XL2® test. In the same group there were 19 PET scans done on malignant nodules which were then incorrectly routed to CT surveillance. Nodify XL2® testing would have reduced that to only 1 PET scan followed by CT surveillance.

2.4.2 Anticipated Clinical Use and Timing of Nodify XL2® Testing

Integrated Diagnostics (InDi) plans to promote the Nodify XL2® test to pulmonologists, both academic and community. The primary goal of Nodify XL2® testing is to reduce avoidable imaging and procedures on benign nodules in the intended use population. The test result document (Section 3.6) will report negative predictive values of 90-98% as both the actual value, and as "Likely Benign". The ordering physician can then decide with the patient what level of risk is appropriate. If a patient is adverse to procedures, a lower NPV result such as 95% may be chosen. Conversely, if a patient is very adverse to an observation period with a surveillance CT, then a 98% NPV result may be needed to decide for CT surveillance.

2.4.2.1 Timing of Nodify XL2® testing

Nodify XL2® testing will be used at one of several points in the evaluation of patients with nodules. Most often, Nodify XL2® testing will be used on lower risk indeterminate nodules (Section 2.2.2.2) after a CT scan and before any other imaging, such as PET. Nodify XL2® in PANOPTIC, showed favorable clinical utility if done before PET scanning (Section 2.4.1.2). This use would avoid both the expense of PET and the risk from high radiation (2.2.6.4).

The Nodify XL2® test can also be used in patients with contraindications to invasive procedures or surgery before deciding about CT surveillance or empiric treatments such as irradiation.

2.4.3 The Nodify XL2® Test's Impact on Invasive Procedures for Indeterminate Nodules The effects of Nodify XL2® testing on invasive procedures and the morbidity and mortality associated with these procedures are assess in this section.

There are two types of invasive diagnostic procedures: biopsies and surgical resection.

2.4.3.1 Biopsies of Nodules

Biopsies can be obtained through a bronchoscope or a needle passed through the chest wall with CT image guidance. A community practice chart review found 38% of patients had a form of biopsy. Complications with biopsies or surgery are increased with age, smoking history, and other lung disease.

Biopsy through the bronchoscope has the lowest risk with a 2-4% risk of bleeding or pneumothorax. The disadvantage of this procedure is inaccurate sampling of the nodule. Correct sampling averages about 50%. The correct sampling rate may improve with modern navigation techniques that are being adopted. Bronchoscopic biopsy use for nodules is currently about 20% of nodules.

Needle biopsies are done in about 15% of patients with nodules with a 1% risk of bleeding, and a 15-19% risk of pneumothorax [R. S. Wiener, L. M. Schwartz, S. Woloshin and G. Welch, "Population-Based Risk for Complications After Transthoracic Needle Lung Biopsy of a Pulmonary Nodule: An Analysis of Discharge Records," Annals of Internal Medicine, vol. 155, no. 3, pp. 137-144, 2011]. About half (7%) of patients with a pneumothorax require chest tube placement with a significant period of hospitalization. Most needles biopsies are diagnostic but the risk of a non-diagnostic result with a malignant nodule is about 20%.

Biopsies (combined bronchoscopy and needle) are performed in about 25% of nodules (200,000) and the procedures are for benign nodules in 42-62% (104,000). Complications from biopsies result in hospitalization in 2-7% (range of bronchoscopy and needle biopsy complications, median 4.5%). That translates into 4,680 excess hospitalizations (104,000×0.045) per year that are potentially avoidable.

2.4.3.2 Surgery for Nodules

Eventually most malignant nodules go to surgery for resection and about 15-25% of patients have biopsy attempts before surgery (not included in Nodify XL2® Impact estimates). The overall surgery rate is about 34% (270,000 per year) for benign and malignant nodules in the nodule population. Complications include death (2% in CMS population [C. E. Iniguez, K. W. Armstrong, Z. Cooper, J. S. Weissman, C. T. Ducko, J. O. Wee, M. P. Martinez, R. Bueno, M. T. Jaklitsch and D. C. Wiener, "Thirty-Day Mortality After Lobectomy in Elderly Patients Eligible for Lung Cancer Screening," The Annals of Thoracic Surgery, vol. 101, no. 2, pp. 541-546,), prolonged lung air leak (3-5%), and pneumonia (1-8%).

Published rates for surgery for benign nodules range from 31-44% [The National Lung Screening Trial Research Team, "Results of Initial Low-Dose Computed Tomographic Screening for Lung Cancer," *The New England Journal of Medicine*, vol. 368, no. 21, pp. 1980-1991, That translates into about 102,000 surgeries (270,000×0.38 [mid-range]) and 2,052 deaths (270,000×0.38×0.02) per year that are avoidable for patients that don't have lung cancer.

2.4.3.3 Nodify XL2® Impact Estimates

Using the figures for potential avoidable invasive procedures calculated above, and assuming the Nodify XL2® test has broad use after reimbursement. Add the clinical utility figure of a 36% reduction of invasive procedures (Sections 2.4.3 and 3.4), then Nodify XL2® testing has the potential to save over 36,000 surgeries, over 1,600 hospitalizations, and almost 750 deaths per year. The majority of these occurring in the CMS population of patients (Section 2.2.1.5).

3. Technical and Performance Summary of the Nodify XL2® Test

This section presents the following details of the Nodify XL2® test:

Development and Validation (Section 3.1):
- The Nodify XL2® test was developed and validated on two large and generalizable prospective studies including the PANOPTIC study, which enrolled 685 subjects across 33 sites.
- The Nodify XL2® test was developed and validated following the National Academy of Medicine's guidelines for rigorous test development.
- The Nodify XL2® test development and validation achieves the highest level of evidence being both prospective and conducted on a large number of independent sites.

Performance (Section 3.2):
- The Nodify XL2® test has a negative predictive value, sensitivity and specificity of 98% (CI: 92%-100%), 97% (CI: 82%-100%) and 44% (CI: 36%-52%).

Comparative Performance (Section 3.3):
- The Nodify XL2® test compares favorably to current practice, PET and four clinical risk predictor models having statistically significant superior performance.

Potential Clinical Utility of Nodify XL2® Testing: Benefit and Harm (Section 3.4):
- Two prospective studies allow calculation of the potential clinical utility of the Nodify XL2® test.

In the PANOPTIC trial, it was shown that if used, Nodify XL2® testing would have eliminated 36% of invasive procedures on benign lung nodules.

Importantly, Nodify XL2® testing is also safer than current practice. If Nodify XL2® were used in PANOPTIC then only 3% of malignant lung nodules would have been erroneously routed away from invasive procedures. In comparison, the physicians erroneously routed 45% of malignant lung nodules away from invasive procedures.

This section closes with the formal specification of the Nodify XL2® test (Section 3.5), the reporting of Nodify XL2® results (Section 3.6), and also a description of the primary differences between XL1 and the Nodify XL2® test (Section 3.7).

3.1 Development and Validation of the Nodify XL2® Test

The Nodify XL2® test was developed on Study 1013 (NCT01752101) and then verified and validated on the PANOPTIC study (NCT01752114). Study 1013 and PANOPTIC are both prospective studies of lung nodules, designed and sponsored by Integrated Diagnostics, for the primary purpose of developing and validating Nodify XL2®. These studies are summarized in Table 3.

TABLE 3

Study 1013 and PANOPTIC showing development phases and numbers of sites and patients.

| Development Phase | Study 1013 Discovery | PANOPTIC Verification & Validation |
|---|---|---|
| Number of Sites | 12 | 33 |
| Patients Enrolled | 475 | 685 |
| Intended Use Patients | 222 | 178 |

Development and validation of Nodify XL2° testing adhered to the best practices for test development as defined by the National Academy of Medicine (NAM) Guidelines for best practices in test development and validation ROM (Institutes of Medicine), Evolution of Translational 'Omics: Lessons Learned and the Path Forward, Washington D.C.: The National Academies Press, 2012]. In particular, discovery and validation were both prospective and conducted on a large number of independent sites. Additionally, verification and validation were conducted under a strict blinding protocol and utilized a $3^{rd}$ party statistician. This is the highest level of clinical validation achievable by the NAM. Details of the early development of the Nodify XL2® test and discovery on Study 1013 [RD35, RDXX] are available for review. The validation protocol and results are also available for review [DES25, VAL25].

3.2 Performance of the Nodify XL2® Test in the PANOPTIC Trial 3.2.1 Performance Measures and Results with the Nodify XL2® Test The performance of the Nodify XL2® test is based on the 178 PANOPTIC subjects in the intended use population. The four standard performance measures for a diagnostic test are sensitivity, specificity, positive predictive value (PPV) and negative predictive value (NPV).

Sensitivity: The percentage of malignant lung nodules correctly predicted as malignant by Nodify XL2® testing.

Specificity: The percentage of benign lung nodules correctly predicted as benign by Nodify XL2® testing.

Negative Predictive Value (NPV): The percentage of lung nodules predicted to be benign by the Nodify XL2® test that are benign.

Positive Predictive Value (PPV): The percentage of lung nodules predicted to be malignant by the Nodify XL2® test that are malignant.

The Nodify XL2® test is designed to be a lung cancer rule out test, that is, it identifies lung nodules that are likely benign so that CT surveillance is used and invasive procedures can be avoided. Consequently, the accuracy at which it reports a lung nodule to be likely benign is of paramount clinical importance. This performance measure is the NPV.

What NPV will be best for deciding the pathway? It depends on patient preference and the physician's advice (Section 2.2.2.2). The ACCP guidelines recommend that a lung nodule can be observed with CT surveillance if the probability of cancer is under 5%. This is equivalent to NPV values over 95%. Nodify XL2® testing has been validated for NPV values of 90% and higher. Table 4 presents the performance of the Nodify XL2® test for NPV values of 90% to 98% along with 95% confidence intervals (CI). It was noted that the largest proportion of Likely Benign reports in the study have a NPV of 98%.

The 90% NPV value is the lowest to be considered "likely benign". This is because NPV values below 90% are not statistically different from the pre-test probability of a lung nodule being benign. Within the intended use population of PANOPTIC this value is 83.7%. This is below the 95% lower CI of all NPV values in Table 4. A test result below 90% NPV does not have a post-test probability of a lung nodule being benign from its pre-test probability. In these cases, the result is considered "Indeterminate".

TABLE 4

Performance and Likely Benign Reports of the Nodify XL2R ® test on 178 patients from the PANOPTIC study at NPV values of 90% to 98% and below 90%. Test results with a NPV at or above 90% NPV are reported as "Likely Benign" whereas those below 90% NPV are reported as "Indeterminate".

| NPV (95% CI) | Sensitivity (95% CI) | Specificity (95% CI) | PPV (95% CI) | % of Reports |
|---|---|---|---|---|
| 98% (92%-100%) | 97% (82%-100%) | 44% (36%-52%) | 25% (17%-34%) | 39% |
| 97% (91%-100%) | 93% (77%-99%) | 49% (41%-57%) | 26% (18%-36%) | 5% |
| 96% (90%-99%) | 90% (73%-98%) | 54% (45%-62%) | 27% (19%-37%) | 4% |
| 95% (89%-99%) | 86% (68%-96%) | 55% (47%-63%) | 27% (18%-37%) | 2% |
| 94% (87%-98%) | 83% (47%-64%) | 56% (64%-94%) | 27% (18%-37%) | 1% |
| 93% (86%-98%) | 79% (60%-92%) | 57% (44%-65%) | 26% (18%-37%) | 2% |
| 92% (85%-97%) | 76% (56%-90%) | 58% (49%-66%) | 26% (17%-37%) | 1% |
| 91% (84%-96%) | 69% (49%-85%) | 64% (56%-72%) | 27% (18%-39%) | 6% |
| 90% (84%-95%) | 55% (36%-74%) | 83% (75%-88%) | 38% (24%-54%) | 18% |
| <90% | — | — | — | 22% |

3.2.2 Graphical Performance of the Nodify XL2® Test

The performance of a diagnostic test is often depicted graphically using a receiver operating characteristic (ROC) curve. There are three landmarks on the ROC plots worth noting.

Landmark #1 is the ROC curve itself for the Nodify XL2® test. The further away from random, shown as the dashed diagonal line, this curve is, the better the overall performance of the diagnostic test. This is typically measured by the area under the curve (AUC).

Landmark #2 is the '95% NPV zone'. The NPV of a diagnostic test depends entirely on its sensitivity, specificity and disease prevalence. This dependency is captured by the following formula:

$$NPV = \frac{\text{specificity} * (1 - \text{prevalence})}{(1 - \text{sensitivity}) * \text{prevalence} + \text{specificity} * (1 - \text{prevalence})}$$

In the case of Nodify XL2® testing, the cancer prevalence in the intended use population is 16.3%. The implication is that those sensitivity and specificity values that result in a clinically relevant NPV of at least 95% can be determined. These sensitivity and specificity values are depicted as the '95% NPV zone'. A robust diagnostic test for ruling out cancer in lung nodules should have sensitivity and specificity within this zone.

Another important aspect of the 95% NPV zone is that this is where Nodify XL2® will be compared to other cancer risk predictors (Section 3.3.3).

Landmark #3 is the point on the Nodify XL2® ROC curve where it reaches maximum NPV. At this point the Nodify XL2® test has sensitivity of 97%, specificity of 44% and NPV of 98%. The NPV is emphasized because this area of the graphic is most relevant for a rule-out type test such as Nodify XL2®.

3.3 Comparative Performance of the Nodify XL2® Test 3.3.1 Current Risk Predictor Selections for Comparison to the Nodify XL2® Test This section compares the performance Nodify XL2® testing to six other cancer risk predictors for lung nodules. All comparisons are made using the same 178 PANOPTIC patients in the lower risk, intended use population. This allows for an 'apples-to-apples' comparison. These six predictors fall into three categories as follows.

Current Practice: Current practice for estimating the cancer risk of a lung nodule is the initial physician cancer risk assessment (pCA) based on physician clinical judgement [A. A. Balekian, G. A. Silvestri, S. M. Simkovich, P. J. Mestaz, G. D. Sanders, J. Daniel, J. Porcel and M. K. Gould, "Accuracy of Clinicians and Models for Estimating the Probability That a Pulmonary Nodule is Malignant," *Annals of the America Thoracic Society*, vol. 10, no. 6, pp. 629-635, 2013]. This also represents how cancer risk was estimated for over 80% of lung nodules evaluated in PANOPTIC and is also a practice recommended in the ACCP Guidelines (Section 2.2.4.1).

PET: PET is referenced in the ACCP Guidelines for use as a tool for assessing cancer risk. PET was used in 75/178=42% of intended use subjects in the PANOPTIC study.

Clinical Risk Predictors: Four clinical risk predictors have been discussed (Section 2.2.4) and here are assessed: Mayo, VA, Brock and Herder. Mayo and VA are referenced in the ACCP Guidelines, however, they were used by under 20% of physicians in the PANOPTIC study. The Brock and Herder models are included for completeness but were not utilized by physicians in the PANOPTIC study as discussed in Sections 2.2.4.2 and 2.2.6.2 respectively. Because the Herder model requires a PET to be performed, only 75/178=42% of the intended use subjects in the PANOPTIC study have a Herder result.

3.3.2 Comparison Methodology

In section 3.3.3, the Nodify XL2® test and six other cancer risk predictors are presented as ROC curves. This will give an overall impression of the performance of these risk predictors in terms of AUC and performance in the important '95% NPV zone'. However, no statistical claims are intended. Full statistical treatment is reserved for Section 3.3.4.

In Section 3.3.4, the Nodify XL2® test is compared 'apples-to-apples' to the six other cancer risk predictors in a strict statistical manner. Except in the case of PET, all of these comparisons are based on the following methodology:

Comparisons are made based on performance in the 95% NPV zone.

The McNemar statistical test is utilized [Q. McNemar, "Note On the Sampling Error of the Difference Between Correlated Proportions or Percentages," *Psycometrika*, vol. 12, no. 2, pp. 153-157, 1947]. The McNemar test is most appropriate when comparing predictors on the same set of samples and at a fixed sensitivity (or fixed specificity).

In the case of PET, a McNemar comparison is not possible due to PET's poor performance in the '95% NPV zone'. Instead, direct NPV performance comparisons are made.

3.3.3 Graphical Comparison of the Nodify XL2® Test to All Other Risk Predictors

Before proceeding to a formal statistical comparison of the Nodify XL2® test to the other risk predictors, an overall picture of the performance of six risk predictors relative to Nodify XL2® testing was analyzed. For this purpose, performance using a ROC plot and measuring the entire AUC was visualized. Statistical comparisons based on the entire AUC were not made as this is not the relevant metric for a rule-out test (despite Nodify XL2® having the highest AUC). Section 3.3.4 makes use of formal statistical comparisons.

The AUCs for Nodify XL2® testing and six other risk predictors are presented in Table 5. Three immediate remarks can be made on this head-to-head comparison in this intended use population with a cancer risk of 50% or less:

The Nodify XL2® test has superior performance overall (highest AUC), but more importantly, the best performance in the '95% NPV Zone'.

Current practice (pCA) performs very poorly overall (AUC=69%) but particularly poorly within '95% NPV zone'.

PET has the worst performance both overall (AUC=58%) and also within the '95% NPV zone'.

Although the most important factor is the superior performance of the Nodify XL2® test in the 95% NPV zone, it is notable that even outside the 95% NPV zone, the performance of the Nodify XL2® test continues to be superior, or equivalent, to all other cancer risk predictors, PET and pCA.

TABLE 5

Overall AUC and 95% CI of the Cancer Risk Predictors

| Cancer Risk Predictor | AUC | 95% CI |
|---|---|---|
| Nodify XL2 ® | 76% | 69%-82% |
| pCA | 69% | 62%-76% |
| VA | 60% | 53%-67% |
| Brock | 71% | 63%-77% |
| Mayo | 69% | 62%-76% |
| Herder | 67% | 56%-78% |
| PET | 58% | 46%-69% |

3.3.4 Statistical Comparisons

In this section the Nodify XL2® test is compared, in a formal statistical sense, to current practice (pCA), four clinical risk predictors, and then PET.

3.3.4.1 Comparison of the Nodify XL2® test to Current Practice (pCA)

Nodify XL2® testing is compared to current practice, physician clinical judgment for the pretest probability of cancer (pCA) in the lower risk group (pCA 50% or less). pCA never reaches the desired 95% NPV level. Since the highest sensitivity attained by pCA is 90%, this level is used to compare the performance of the Nodify XL2® test to pCA.

Using the McNemar test (Section 3.3.2), at the same sensitivity of 90%, Nodify XL2® has significantly greater specificity with p-value of 2.12E-11.

3.3.4.2 Comparison of the Nodify XL2® test to Clinical Risk Predictors

Nodify XL2® testing was compare to four clinical risk predictors (Mayo, VA, Brock and Herder). The comparison is made at sensitivities of 90% and 97% which Nodify XL2®, and all four clinical risk predictors, attain. These two sensitivities were included for a robust comparison.

Using the McNemar test (Section 3.3.2), at sensitivities of 90% and 97%, Nodify XL2® testing has significantly greater specificity than the four clinical risk predictors with p-values reported in Table 6. We note that comparisons between the Nodify XL2® test and all models except Herder are made on all 178 PANOPTIC patients. For Herder (which requires a PET to be performed) only 75 patients could be compared. This lower sample number resulted in higher (but still significant) p-values.

TABLE 6

Comparison of the Nodify XL2 ® test to
Clinical Risk Predictors for incidental
(Mayo & VA) and screen-detected (Brock) nodules.
Herder combines clinical factors with PET.

| Comparison | 90% Sensitivity p-value | 97% Sensitivity p-value |
|---|---|---|
| Nodify XL2 ® vs. Mayo | 0.0009 | 0.0009 |
| Nodify XL2 ® vs. VA | 1.562e-11 | 2.71E-7 |
| Nodify XL2 ® vs. Brock | 0.0021 | 0.0051 |
| Nodify XL2 ® vs. Herder | 0.0455 | 0.0233 |

3.3.4.3 Comparison of the Nodify XL2® test to PET

Of the 178 PANOPTIC patients within the intended use of Nodify XL2®, 75 had a diagnostic PET performed.

Because PET never reaches the 95% NPV zone or a sufficiently high sensitivity, the McNemar test cannot be applied. Instead, we compare the NPV of PET directly to the NPV of Nodify XL2® testing.

The highest NPV for PET is 79% (95% CI:66%-88%) so this is compared to when Nodify XL2® testing reaches a NPV of 95% (95% CI:89%-99%). These two CI do not overlap, and so, the Nodify XL2® test has significantly better NPV as compared to PET.

3.4 Potential Clinical Utility of Nodify XL2® Testing: Benefit and Harm

PANOPTIC was a non-interventional study, however, the potential clinical utility of Nodify XL2® testing can be estimated from PANOPTIC by answering the following question:

"If Nodify XL2® were used in PANOPTIC to identify lung nodules likely to be benign, how many benign (benefit) and malignant (harm) nodules would have been routed away from invasive procedures into CT surveillance"?"

At NPV=98% (see Table 7), the Nodify XL2® test has the following potential clinical utility in PANOPTIC:
  15/42=36% of benign nodules would have been saved from unnecessary invasive procedures (benefit).
  1/29=3% of malignant nodules would have been erroneously routed to CT surveillance (harm).

At NPV=95% (see Table 7), Nodify XL2® testing has the following potential clinical utility in PANOPTIC:
  20/42=48% of benign nodules would have been saved from unnecessary invasive procedures (benefit).
  2/29=7% of malignant nodules would have been erroneously routed to CT surveillance (harm).

TABLE 7

Potential Clinical Utility of Nodify XL2 ® Testing

| NPV | Reduction in Invasive Procedures on Benign Nodules (95% CI) | Malignant Nodules Sent to CT Surveillance (95% CI) |
|---|---|---|
| 98% | 15/42 = 36% (22%-52%) | 1/29 = 3% (0%-18%) |
| 97% | 17/42 = 40% (26%-57%) | 2/29 = 7% (1%-23%) |
| 96% | 19/42 = 45% (30%-61%) | 2/29 = 7% (1%-23%) |
| 95% | 20/42 = 48% (32%-64%) | 2/29 = 7% (1%-23%) |
| 94% | 20/42 = 48% (32%-64%) | 2/29 = 7% (1%-23%) |
| 93% | 22/42 = 52% (36%-68%) | 3/29 = 10% (2%-27%) |
| 92% | 22/42 = 52% (36%-68%) | 4/29 = 14% (4%-32%) |
| 91% | 25/42 = 60% (43%-74%) | 4/29 = 14% (4%-32%) |
| 90% | 32/42 = 76% (61%-88%) | 7/29 = 24% (10%-44%) |

How safe is Nodify XL2® testing? We observe that in the intended use population in PANOPTIC, 13/29=45% of malignant nodules were routed to CT surveillance (then having a risk of delayed diagnosis). Comparing this to the estimates shown in Table 7 illustrates that the Nodify XL2® test will provide a safe test for both reducing unnecessary invasive procedures while simultaneously sending fewer malignant nodules to CT surveillance.

3.5 Technical Definition of the Nodify XL2® Test

Nodify XL2® testing integrates the relative abundance of two plasma proteins (LG3BP and C163A) with five clinical risk factors (age, smoking status, nodule diameter, nodule spiculation status and nodule location). Nodify XL2® testing provides a numerical value, XL_2(k), for a subject k, as defined below:

$$XL\_2(k) = \begin{cases} \max(0, p(k) - 0.5), & \log_2\left(\frac{LG3BP}{C163A}\right) \leq .38 \\ p(k), & \log_2\left(\frac{LG3BP}{C163A}\right) > .38 \end{cases}$$

$$p(k) = \frac{e^X}{1 + e^X}$$

$X = -6.8272 + 0.0391*\text{Age} + 0.7917*\text{Smoker} + 0.1274*\text{Diameter} + 1.0407*\text{Spiculation} + 0.7838*\text{Location}$ where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0). The linear function X that integrates the clinical risk factors is a simplification of the Mayo clinical risk predictor that eliminates the cancer risk history factor.

XL_2( ) ranges between 0 and 1. The closer XL_2(k) is to 0, the more likely subject k has a very high NPV which is calculated using PANOPTIC data.

The ranges of the XL_2( ) function for the NPV values of 90% to 98% are shown in Table 8, along with the other key performance indicators.

3.6 Reporting Nodify XL2® results

Nodify XL2® results will be reported as Likely Benign or Indeterminate, with the NPV value and confidence intervals shown in the Likely Benign reports.

The separation of likely benign and indeterminate is based on the cancer prevalence of the study population and statistical comparisons. The cancer prevalence in the intended use population in the PANOPTIC study was 16.3% which corresponds to a benign prevalence of 83.7%. In other words, the pre-test probability of a lung nodule being benign is 83.7% before any clinical judgment or testing. Nodify XL2® reports "Likely Benign" when the post-test probability of being benign (i.e. the NPV) is 90% or higher as shown in Table 8.

Note that when the "k" value exceeds 0.354, the lower confidence interval of an NPV of less than 90% will overlap with the prevalence of 83.7% for the population. Therefore, this will be when the test report changes from Likely Benign to Indeterminant.

TABLE 8

Nodify XL2 ® Performance, Test Report, and Percentage of Reports at multiple negative predictive values for Likely Benign results (n = 178 patients)

| XL_2(k) Value | NPV (95% CI) | Sensitivity (95% CI) | Specificity (95% CI) | PPV (95% CI) | Test Report | Percentage of Tests Reported |
|---|---|---|---|---|---|---|
| 0 to 0.131 | 98% (92%-100%) | 97% (82%-100%) | 44% (36%-52%) | 25% (17%-34%) | Likely Benign | 39% |
| >0.131 to 0.1613 | 97% (91%-100%) | 93% (77%-99%) | 49% (41%-57%) | 26% (18%-36%) | Likely Benign | 5% |
| >0.1613 to 0.172 | 96% (90%-99%) | 90% (73%-98%) | 54% (45%-62%) | 27% (19%-37%) | Likely Benign | 4% |
| >0.172 to 0.176 | 95% (89%-99%) | 86% (68%-96%) | 55% (47%-63%) | 27% (18%-37%) | Likely Benign | 2% |
| >0.176 to 0.1785 | 94% (87%-98%) | 83% (64%-94%) | 56% (47%-64%) | 27% (18%-37%) | Likely Benign | 1% |
| >0.1785 to 0.193 | 93% (86%-98%) | 79% (60%-92%) | 57% (44%-65%) | 26% (18%-37%) | Likely Benign | 2% |
| >0.193 to 0.195 | 92% (85%-97%) | 76% (56%-90%) | 58% (49%-66%) | 26% (17%-37%) | Likely Benign | 1% |
| >0.195 to 0.2306 | 91% (84%-96%) | 69% (49%-85%) | 64% (56%-72%) | 27% (18%-39%) | Likely Benign | 6% |
| >0.2306 to 0.354 | 90% (84%-95%) | 55% (36%-74%) | 83% (75%-88%) | 38% (24%-54%) | Likely Benign | 18% |
| >0.354 | — | — | — | — | Indeterminate | 22% |

3.7 Primary Differences of XL1 and the Nodify XL2® Test

Nodify XL2® is a second generation version of XL1 (formerly called Xpresys® Lung) that has four significant improvements over XL1:

3.7.1. Intended Use Population

The intended use population of Nodify XL2® testing are patients with a lower cancer risk (50% or less pre-test probability), whereas the intended use population of XL1 included all patient risk groups (0%-100%). Under guidance from KOL leaders and commercial experience with XL1, it became clear that physicians needed a test to differentiate benign from malignant nodules. And that need is greatest in patients with lower risk rather than higher risk (Section 2.2.3). This focusing of the intended use population has led to performance improvements.

3.7.2. Reduction in Molecular Factors

Discovery work on Study 1013 identified two proteins (LG3BP and C163A) that were more accurate than the five diagnostic proteins of XL1 at identifying benign nodules for patients with a lower cancer risk. The likely reason for this is that protein expression differs between lower and higher risk nodules [RDXX].

3.7.3. Addition of Clinical Risk Factors

XL1 is purely a molecular test whereas the Nodify XL2® test incorporates molecular markers with known clinical risk factors (Section 3.5). This not only enhances the performance of Nodify XL2® over XL1, but is appealing to physicians as these are the clinical risk factors they currently use to assess cancer risk. That is, the Nodify XL2® test is not attempting to replace the current practice of using clinical risk factors but augments current practice with molecular factors (Section 3.3.3.1).

3.7.4. Quality of Clinical Evidence

XL1 was developed and validated on five archival biobanks. In contrast, the Nodify XL2® test was developed and validated in two prospective studies with samples collected using a uniform protocol. The first, 'Study 1013' spanned 12 sites and enrolled 475 subjects. The second, TANOPTIC' spanned 33 sites and enrolled 685 subjects. Consequently, Nodify XL2® testing is more generalizable to clinical practice. Furthermore, PANOPTIC collected physician probabilities of cancer risk and clinical factors to allow Nodify XL2® to be directly compared to current practice in lung nodule evaluation.

Two proteins used in the Nodify XL2® test, C163A and LG3BP, have been measured by either multiple reaction monitoring mass spectrometry (MRM MS) and ELISA previously. Protein measurements from the two techniques were compared using correlation and statistical analysis, and significance of the concordance was found between the two methods. This comparison study is described in detail in WO/2019/079635, the content of which is incorporated by reference herein in its entirety.

Prognostic Assays

The diagnostic methods described herein can furthermore be utilized to identify subjects having or at risk of developing a disease, disorder, or condition associated with C163A and/or LG3BP (e.g., lung cancer).

The assays described herein, such as the preceding diagnostic assays or the following assays, can be utilized to identify a subject having or at risk of developing a disorder associated with C163A and/or LG3BP. Thus, the present invention provides a method for identifying a disorder associated with C163A and/or LG3BP in which a test sample is obtained from a subject and C163A and/or LG3BP is detected, wherein the presence of C163A and/or LG3BP is diagnostic for a subject having or at risk of developing the disorder associated with C163A and/or LG3BP. As used herein, a "test sample" refers to a biological sample obtained from a subject of interest. For example, a test sample can be a biological fluid (e.g., cerebrospinal fluid or serum), cell sample, or tissue, such as a nasal swab or lung tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat such a disorder associated with C163A and/or LG3BP (e.g., lung cancer). For example, such methods can be used to determine whether a subject can be effectively treated with one or a combination of agents. Thus, the present invention provides methods for determining whether a subject can be effectively treated with one or more agents for treating a disorder associated with C163A and/or LG3BP in which a test sample is obtained and C163A and/or LG3BP is detected (e.g., wherein the abundance of C163A and/or LG3BP is diagnostic for a subject that can be administered the agent to treat the disorder associated with C163A and/or LG3BP).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving C163A and/or LG3BP.

Furthermore, any cell type or tissue expressing C163A and/or LG3BP may be utilized in the prognostic assays described herein.

Monitoring of Effects During Clinical Trials

Monitoring the influence of agents (e.g., compounds, drugs or small molecules) on the activity of C163A and/or LG3BP can be applied not only in basic drug screening, but also in clinical trials. For example, the effectiveness of an agent to reduce a level or activity of C163A and/or LG3BP, can be monitored in clinical trials of subjects with lung cancer, detectable by the antibodies or fragments described herein. In such clinical trials, the level or activity of C163A and/or LG3BP, and/or symptoms or markers of the disorder of interest (e.g., lung cancer), can be used as a "read out" or marker of the phenotype of a particular cell, tissue, or system.

In one embodiment, the present invention provides a method for monitoring the effectiveness of treatment of a subject with an agent (e.g., an agonist, antagonist, peptidomimetic, polypeptide, peptide, nucleic acid, small molecule, or other drug candidate) including the steps of (i) obtaining a pre-administration sample from a subject prior to administration of the agent; (ii) detecting the level of C163A and/or LG3BP, or a fragment thereof, in the pre-administration sample; (iii) obtaining one or more post-administration samples from the subject; (iv) detecting the level of C163A and/or LG3BP or the fragment thereof, in the post-administration samples; (v) comparing the level of C163A and/or LG3BP, or the fragment thereof, in the pre-administration sample with C163A and/or LG3BP, or the fragment thereof, in the post-administration sample or samples; and (vi) altering the administration of the agent to the subject accordingly. For example, increased administration of the agent may be desirable to decrease the level of C163A and/or LG3BP, i.e., to increase the effectiveness of the agent. According to such an embodiment, C163A and/or LG3BP may be used as an indicator of the effectiveness of an agent, even in the absence of an observable phenotypic response. Similarly, C163A and/or LG3BP analysis, such as by immunohistochemistry (IHC), can also be used to select patients who will receive treatment.

EXAMPLES

The invention is further described in the following examples, which do not limit the scope of the invention described in the claims.

Example 1—Generation of Monoclonal Antibodies

Peptide Design, Selection and Synthesis

Peptides used in Nodify XL2® Mass spec assay for detecting LG3BP and C163A have been described previously (Sci Transl Med. 2013 Oct 16; 5(207): 207ra142. doi: 10.1126/scitranslmed.3007013). The goal was to identify antigenic peptides that would be captured from tryptic digests of LG3BP and C163A. Four each peptides for LG3BP and for C163A were identified for immunization (Table 9). The final peptides chosen (Table 9) demonstrated excellent antigenicity potential and recognition of highly predicted tryptic peptides (INPASLDK(SEQ ID NO: 44) and VEIFYR(SEQ ID NO: 41)) throughout the monoclonal antibody generation for each of the two proteins.

TABLE 9

| Peptide Sequence | Start | End | Length | Predicted Tryptic Peptide | Predicted m/z of Tryptic peptide |
|---|---|---|---|---|---|
| LG3BP | | | | | |
| ELSEALGQIFDSQRGC (SEQ ID NO: 21) | 138 | 153 | 16 | ELSEALGQIFDSQR (SEQ ID NO: 22) | 1592.79 |
| CGHTVILTANLE (SEQ ID NO: 23) | 170 | 181 | 12 | GCDLSISVNVQGEDALGFCGHTVILTANLEAQALWK (SEQ ID NO: 24) | 3772.87 |
| TQAEAWPSVPT (SEQ ID NO: 25) | 291 | 301 | 11 | LCLQFLAWNPEALTQAEAWPSVPTDLLQLLLPR (SEQ ID NO: 26) | 3797.01 |
| ASHEEVEGLVEK (SEQ ID NO: 27) | 334 | 345 | 12 | ASHEEVEGLVEK (SEQ ID NO: 27) | 1326.65 |
| YYPYQSFQTPQHPS (SEQ ID NO: 28) | 455 | 468 | 14 | YYPYQSFQTPQHPSFLFQDK (SEQ ID NO: 29) | 2677.28 |
| C163A | | | | | |
| LVDGVTEC (SEQ ID NO: 30) | 268 | 275 | 8 | LVDGVTECSGR (SEQ ID NO: 31) | 1136.28 |
| CAGTVEVEIQR (SEQ ID NO: 32) | 382 | 392 | 11 | CAGTVEVEIQRLLGK (SEQ ID NO: 33) | 1204.6 |
| TSYQVYSK (SEQ ID NO: 34) | 422 | 429 | 8 | TSYQVYSK (SEQ ID NO: 34) | 975.48 |
| NGNETSLWDC (SEQ ID NO: 35) | 443 | 452 | 10 | IQATNTWLFLSSCNGNETSLWDCK (SEQ ID NO: 36) | 2731.254 |
| CGVALSTPGGAR (SEQ ID NO: 37) | 626 | 637 | 12 | CGVALSTPGGAR (SEQ ID NO: 37) | 1088.57 |
| GNESSLWDC (SEQ ID NO: 38) | 1000 | 1008 | 9 | GNESSLWDCPAR (SEQ ID NO: 39) | 1334.58 |

Final selected peptides for immunization are listed below in Table 10. The ones highlighted in bold (INPASLDK (SEQ ID NO: 44) and VEIFYR (SEQ ID NO: 41)) were of highest interest based on the previous publication (Sci Transl Med. 2013 Oct 16; 5(207): 207ra142. doi: 10.1126/scitranslmed.3007013).

TABLE 10

| Protein | Tryptic Peptide | Reason for inclusion |
|---|---|---|
| LG3BP | ELSEALGQIFDSQR (SEQ ID NO: 22) | Predicted |
| LG3BP | STHTLDLSR (SEQ ID NO: 40) | Size/Hydrophobicity |
| LG3BP | VEIFYR (SEQ ID NO: 41) | Current assay and STM publication |
| LG3BP | ASHEEVEGLVEK (SEQ ID NO: 27) | Predicted and STM publication |
| C163A | GENLVHQIQYR (SEQ ID NO: 42) | Size/Hydrophobicity |
| C163A | TSYQVYSK (SEQ ID NO: 43) | Predicted and STM |
| C163A | INPASLDK (SEQ ID NO: 44) | Current Assay and STM publication |
| C163A | LEVFYNGAWGTVGK (SEQ ID NO: 45) | Size/Hydrophobicity |

The final selected peptides were ordered (Table 10). For LG3BP, H2N-VEIFYRC-OH was our focus with additional three peptides selected for testing for monoclonal generation since it was in the current assay. For C163A, H2N-IN-PASLDKC-OH was synthesized. All ordered peptides were >95% Purity with 4 mgs provided as 2 mgs to KLH and 2 mgs to PEG2-Biotin via cysteine. Orders for same peptides but free of KLH or PEG2-Biotin were also placed for use in screening and antibody development. Additional amino acid analysis were used to confirm peptide integrity.

Immunization and Hybridoma Development

The hybridoma development service from Maine Biotechnology Services was used.

mAb Development Outline

C163A: Monoclonal antibodies that are specific for the C163A peptide immunogens (C1, C2, C3 and C4) were developed. Antibodies were used to capture these same peptides from human samples (peptides were generated via tryptic digestion of the samples). The captured peptides were used for binding assays including in ELISA, WB, Immunoprecipitation (IP), and ELISA or IP coupled with mass spectrometry-based biomarker analysis.

LG3BP: Monoclonal antibodies that are specific for the LG3BP peptide immunogens (L1, L2, L3 and L4) were developed. Antibodies were used to capture these same peptides from human samples (peptides were generated via tryptic digestion of the samples). The captured peptides were used for binding assays including in ELISA, WB, Immunoprecipitation (IP), and ELISA or IP coupled with mass spectrometry-based biomarker analysis.

Reagent: the 4 KLH-conjugated peptides (1:1:1:1) (0.5 mg of each) were mixed.

Mice were immunized using our 28 Day Rapid Immunization Protocol (RIMMS) which included a series of low-dosage immunizations administered over a two-week period. Test bleeds were taken on Day 20 and antisera samples were assessed to determine whether fusion-ready titer, as defined by an OD>0.1 above background at 1:31K serum dilution, has been reached. When titers were sufficient, we proceeded directly to fusions.

Screening: serum screening assay parameters to accurately assess the antisera titers of the immunized animals. The indirect ELISA was qualified for use as a primary fusion screen to identify and characterize antibody-secreting hybridoma fusion products. Streptavidin plates were used for the peptide screens (coat SA at 2 ug/mL). Biotin conjugated peptides were coated at 1 ug/mL in PBS. Following a blocking step with casein, serially diluted test bleeds were incubated, detected with an HRP conjugated anti-mouse secondary antibody and developed with TMB.

Fusion Ready Titers: 3 Balb/c & 3 AJ mice were immunized. Fusion-ready titer to LG3BP or C163A peptides was defined as an OD>0.1 above background at the 1:31K serum dilution from test bleed.

Fusion Screening, Selection and Scale-up: Selected fusion products were selected on peptide-specific reactivity (e.g. L1 or L2 or L3 or L4) and secondary screening indicated maintained peptide-specific reactivity.

Subcloning: Fusion products were subcloned via limiting dilution to obtain a monoclonal culture.

Evaluation at Biodesix: fusion supernatant from hybridoma products, supernatant from hybridoma subclones, and terminal bleeds from mice were scaled-up and tested aby Biodesix by various analytic methods.

LG3BP Titer Data

SUMMARY

Serum samples from each mouse were evaluated against each of the 4 individual (biotin-conjugated) peptides using streptavidin-capture ELISA. There was an individual tab for each peptide/mouse strain (tabs #1-4 contain AJ data; tabs #5-8 contain the Balb/c data).

All mice in both cohorts have established a response against all 4 peptides. Response was a bit higher in the AJ mice.

Titers indicated that all 4 peptides were immunogenic (there was not a significant bias toward/away from any of them).

A few of the AJ mice had hit the "fusion-ready" titer threshold to one/a couple of the peptides, but none of them had hit it across the board. (Fusion-ready titer was defined as an OD>0.1 above background at the 1:31250 dilution-these ODs were highlighted in green on each tab).

AJ #2 were used for fusions. It was decided to boost AJ #1 and #3 as backup.

LG3BP Primary Fusion Selection Data

SUMMARY 20 clones were selected from L3

5 clones were selected each for L1, L2, L4

Total of 35 clones were selected for subcloning, scaled up, cryo, and expanded for 15 mL overgrown supernatants LG3BP Secondary/Confirmatory Fusion Data

SUMMARY

L1: ⅕ FPs remained L1-specific (the other 4 exhibited reactivity to a mix of the other peptides)

L2: ⅗ FPs remained L-2 specific (the other 2 exhibited reactivity to a mix of the other peptides)

L3:14/20 remained L-3 specific (the other 6 exhibited reactivity to a mix of the other peptides)

L4: ⅘ FPs remained L4-specific (1 was now dual reactive to L3 and L4)

LG3BP Purification Report

TABLE 11

9 subclones were shipped to Biodesix.

| Reference Number | Sample ID | [Ab] mg/ml | Well Location | Accession of origin |
|---|---|---|---|---|
| 1 | LG3BP-AJ-1.2-06B10-02B07 | 0.8 | 01A01 | 18-0270S5 |
| 2 | LG3BP-AJ-1.2-06B10-02B11 | 1.0 | 01A02 | 18-0270S5 |
| 3 | LG3BP-AJ-1.2-06B10-02E03 | 1.0 | 01A03 | 18-0270S5 |
| 4 | LG3BP-AJ-1.2-14E09-02F04 | 1.2 | 01A04 | 18-0270S6 |
| 5 | LG3BP-AJ-1.2-14E09-02F08 | 1.3 | 01A05 | 18-0270S6 |
| 6 | LG3BP-AJ-1.2-14E09-02G07 | 0.9 | 01A06 | 18-0270S6 |
| 7 | LG3BP-AJ-1.2-15B07-02C07 | 1.2 | 01A07 | 18-0270S7 |
| 8 | LG3BP-AJ-1.2-15B07-02F10 | 1.1 | 01A08 | 18-0270S7 |
| 9 | LG3BP-AJ-1.2-15B07-02G07 | 1.3 | 01A09 | 18-0270S7 |
| 10 | (+) ctl | 1.2 | 01A10 | |

TABLE 12

LG3BP Selected for Scale Up
LG3BP monoclonal antibodies

| Parent Clone | Antibody Number | Peptide Target | Concentration (mg/ml) |
|---|---|---|---|
| 11D10 | 02B03 | ELSEA | 1.0 |
|  | 02F04 | ELSEA | 1.0 |
|  | 02G03 | ELSEA | 0.9 |
| 11G10 | 01C06 | ELSEA | 1.0 |
|  | 01E10 | ELSEA | 1.0 |
|  | 02H03 | ELSEA | 0.9 |
| 15D06 | 02C06 | ELSEA | 0.8 |
|  | 02D02 | ELSEA | 0.9 |
|  | 02G03 | ELSEA | 0.8 |
| 12D04 | 02C02 | STHT | 1.4 |
|  | 02D02 | STHT | 1.2 |
|  | 02G02 | STHT | 0.9 |
| 11E03 | 02E04 | ASHE | 1.0 |
|  | 02F05 | ASHE | 0.9 |
|  | 02F10 | ASHE | 1.2 |
| 14E09 | 02F04 | VEIFYR | 1.2 |
|  | 02F08 | VEIFYR | 1.3 |
|  | 02G07 | VEIFYR | 0.9 |
| 15B07 | 02C07 | VEIFYR | 1.2 |
|  | 02F10 | VEIFYR | 1.1 |
|  | 02G07 | VEIFYR | 1.3 |
| 06B10 | 02B07 | VEIFYR | 0.8 |
|  | 02B11 | VEIFYR | 1.0 |
|  | 02E03 | VEIFYR | 1.0 |

C163A Titer Data (original)

SUMMARY

Both cohorts of mice had established a response against the peptides

None of the mice had met the "fusion-ready" threshold for any of the peptides (and the titers were, in general, a bit lower than those in the LG3BP project).

It was decided to boost all Balb/c (not AJ).

C163A Titer Data (Boost)

SUMMARY

All of the mice expanded their responses to each of the 4 peptides. Balb/c #3 was the only mouse that meets the "fusion-ready" threshold for all 4 peptides, but her anti-C3 peptide is lower than the Balb/c #1 and #2 anti-C3 response. (C3 peptde=INPASLDK(SEQ ID NO: 44))

Blab/c #3 was used for fusion.

C163A Primary Fusion Selection Data

SUMMARY

There were strong single positives for each of the C163A peptides—including the C3 peptide (INPASLDKC-OH).

25 clones of C3-specific fusion products 5 each for C1, C2 and C4

Total of 40 clones were selected for scaled up, cryo, and expanded for 15 mL overgrown supernatants.

C163A Secondary/Confirmatory Fusion Data

SUMMARY

C1 peptide: of the original 5 selections, 4 maintained strong reactivity (10H07 lost all signal)

C2 peptide: all 5 fusion products remained C2-specific

C3 peptide: of the original 25 were selected, 23 remain C3-specific (06B03 lost all reactivity; 15C05 exhibits reactivity to all 4 peptides)

C4 peptide: of the original 5, 3 remained C4-specific (18F11 now exhibits low-level response to the C3 peptide; 19D10 gained reactivity across the board)

Selected for subcloning

C163A Purification Report 18 subclones were shipped to Biodesix.

ReadyPure from 100 mL cultures

C163A-BA-1.3-14A11-02C11 (GENL)

C163A-BA-1.3-10A12-02C11 (LEVF)

C163A-BA-1.3-13 G05-02E09 (INP)

C163A-BA-1.3-13H05-02F02 (INP)

TABLE 13

C163A Selected for scale-up
LG3BP monoclonal antibodies

| Parent Clone | Antibody Number | Peptide Target | Concentration (mg/ml) |
|---|---|---|---|
| 11D10 | 02B03 | ELSEA | 1.0 |
|  | 02F04 | ELSEA | 1.0 |
|  | 02G03 | ELSEA | 0.9 |
| 11G10 | 01C06 | ELSEA | 1.0 |
|  | 01E10 | ELSEA | 1.0 |
|  | 02H03 | ELSEA | 0.9 |
| 15D06 | 02C06 | ELSEA | 0.8 |
|  | 02D02 | ELSEA | 0.9 |
|  | 02G03 | ELSEA | 0.8 |
| 12D04 | 02C02 | STHT | 1.4 |
|  | 02D02 | STHT | 1.2 |
|  | 02G02 | STHT | 0.9 |
| 11E03 | 02E04 | ASHE | 1.0 |
|  | 02F05 | ASHE | 0.9 |
|  | 02F10 | ASHE | 1.2 |
| 14E09 | 02F04 | VEIFYR | 1.2 |
|  | 02F08 | VEIFYR | 1.3 |
|  | 02G07 | VEIFYR | 0.9 |
| 15B07 | 02C07 | VEIFYR | 1.2 |
|  | 02F10 | VEIFYR | 1.1 |
|  | 02G07 | VEIFYR | 1.3 |
| 06B10 | 02B07 | VEIFYR | 0.8 |
|  | 02B11 | VEIFYR | 1.0 |
|  | 02E03 | VEIFYR | 1.0 |

Example 2—Characterization of Monoclonal Antibodies

Monoclonal Antibodies were Screened with ELISA.

Five monoclonal cell Lines were created for LG3Bp and C163a with murine IgG.

Cells were scaled up in roller bottle, purified, and screened using the respective unlabeled immunizing peptides. Purities of clones ranged from 92-98% by size exclusion chromatography. Cell lines were characterized by Isoelectric Focusing (IEF), Size Exclusion Chromatography (SEC), and Polyacrylasmide Gel Electrophoresis (SDS PAGE). Two of C163a (INPA) and three of LG3BP (VEIFYR(SEQ ID NO: 41)) clones were sent for sequencing. Additional clones for C163A GENL and LEVF were generated. Binding of the monoclonal antibodies (mAbs) to the relevant peptide was confirmed by an ELISA assay (Tables 14 A-C). Briefly, two monoclonal antibodies (murine cell lines C163A-BA-1.3-2H05-02F02 and LG3BP-AJ-1.2-14E09-02F04; IgG1; Maine Biotechnology Services, Inc.) were reacted in a 96-well plate coated with two different concentrations of the INPASLDK (SEQ ID NO: 44) (INP) and VEIFYR (SEQ ID NO: 41) (VEI) peptides (Vivitide Inc). The peptides were diluted in high phosphate buffer pH 8.5, and 100 uL each dispensed separately into wells of a Nunc Medisorp 96-well plate (Thermo Scientific, cat #467320) to deliver 2.3 and 0.5 nmol INP, and 2.4 and 0.5 nmol VEI. The plate was incubated overnight (~20 hrs) at room temperature to coat the peptides onto the plate through direct, passive adsorption and then washed 4× with PBS containing 0.1% Tween 20 (PBST) before being blocked with StabilCoat® Immunoassay Stabilizer (Sigma, cat # S0950) for 90 minutes at room temperature. The mAbs were diluted in PBS containing 0.1% casein to final concentrations of 14 and 2.8 ug/mL α-INP mAb, and 10 and 2 ug/mL α-VEI mAb. After aspirating the blocking buffer, 100 uL of each mAb dilution was added in single wells containing each of the peptide concentrations. The plate was sealed, and the mAbs were reacted for 75 minutes at room temperature with shaking at 400 rpm and then washed 4× with PBST. A 1:500 dilution of [1.3 g/L] rabbit α-mouse IgG-HRP (Dako, cat # P0260) in PBS containing 0.1% casein was added to each well, and the sealed plate was incubated at room temperature for 60 minutes. The plate was washed 4× with PBST before adding 100 uL TMB/E substrate (Millipore Sigma, cat # ES001) to each well. After a 15 min incubation, the reaction was stopped by adding 100 uL [1000 ppm F] sodium fluoride solution (RICCA, cat #3173-32). The optical density of each well was measured at 650 nm using a spectrophotometer.

Figure 1B:
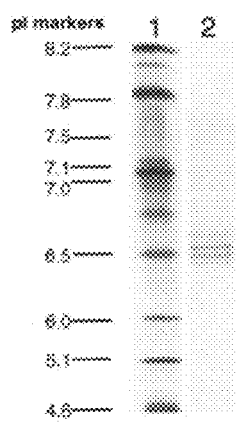

IEF data for C163A INPA clones are shown in FIGS. 1A and 1B.

Figure 2A:
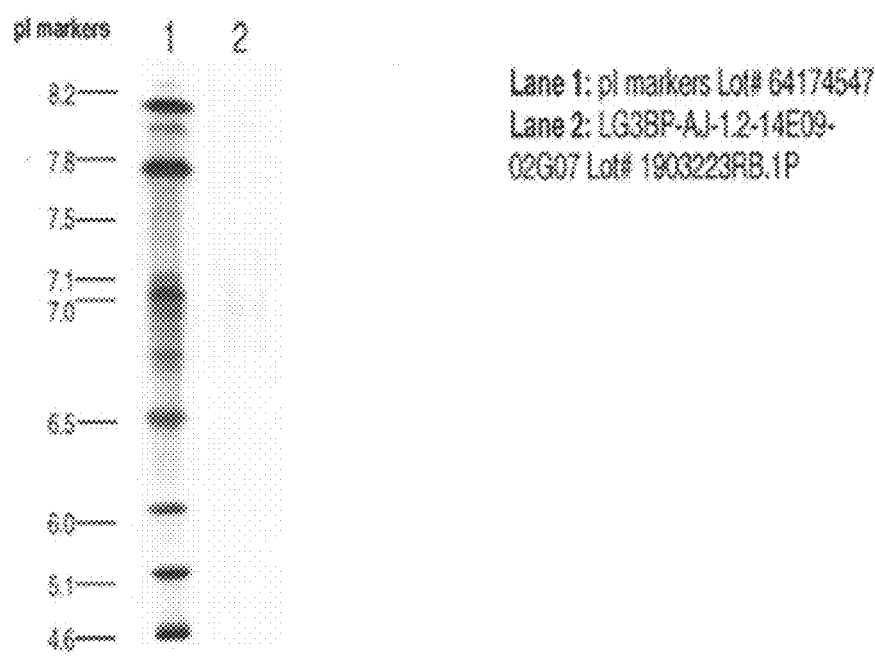
FIGS. 2A-2C show IEF data for LG3BP VEYFIR clones.
Figure 2B:
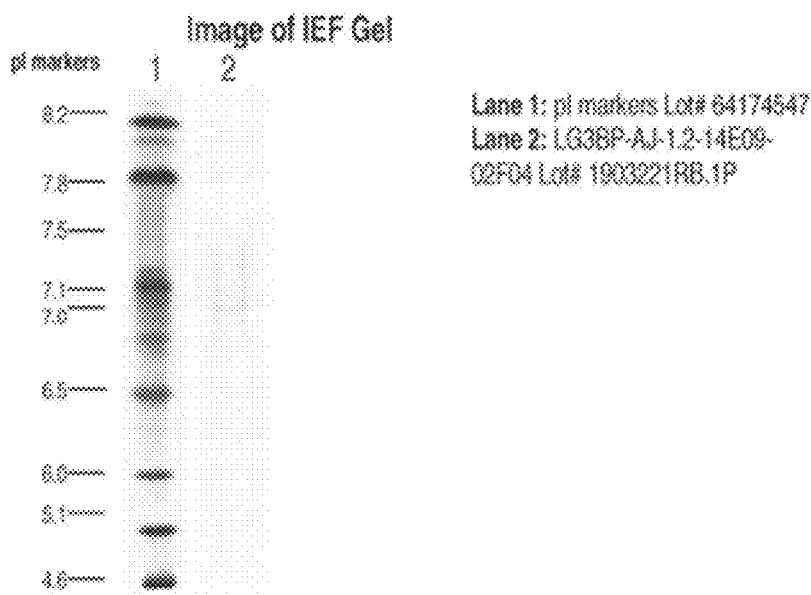
Figure 2C:
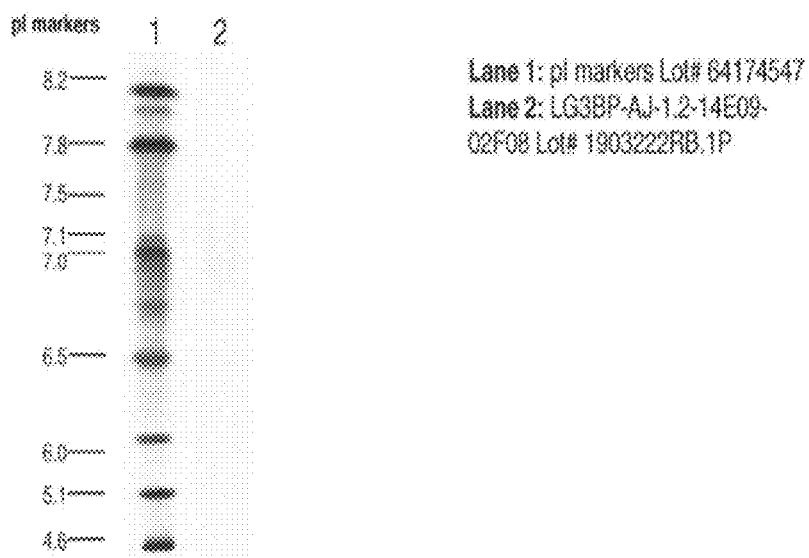

IEF data for LG3BP VEYFIR clones are shown in FIGS. 2A-2C.

Figure 3A:
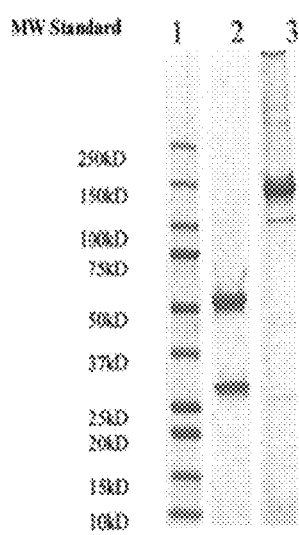
Figure 3A:

SDS-PAGE data for C163A INPA clones are shown in FIGS. 3A and 43B.

Figure 4A:
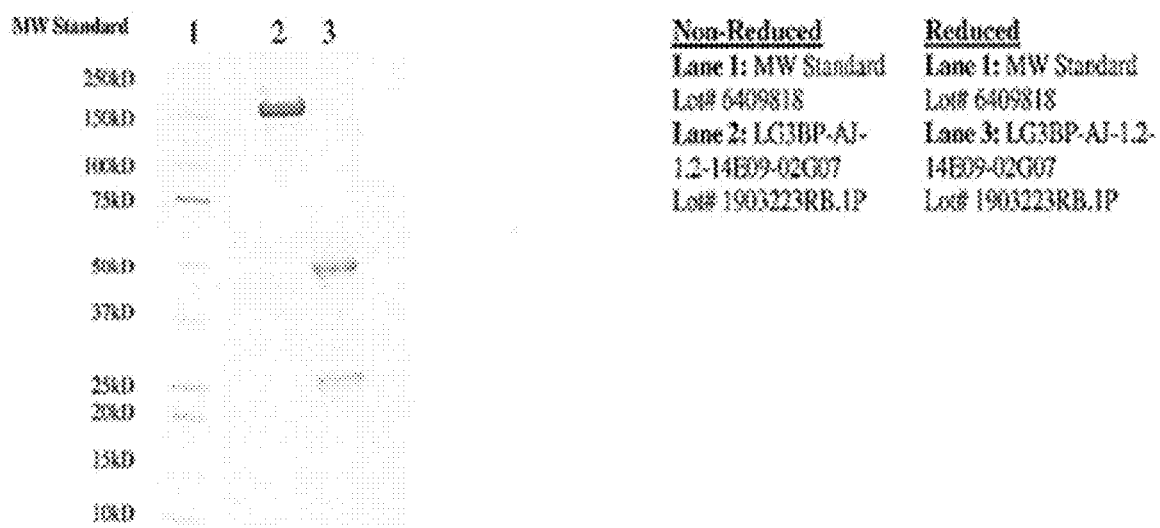
Figure 4A:
Figure 4B:
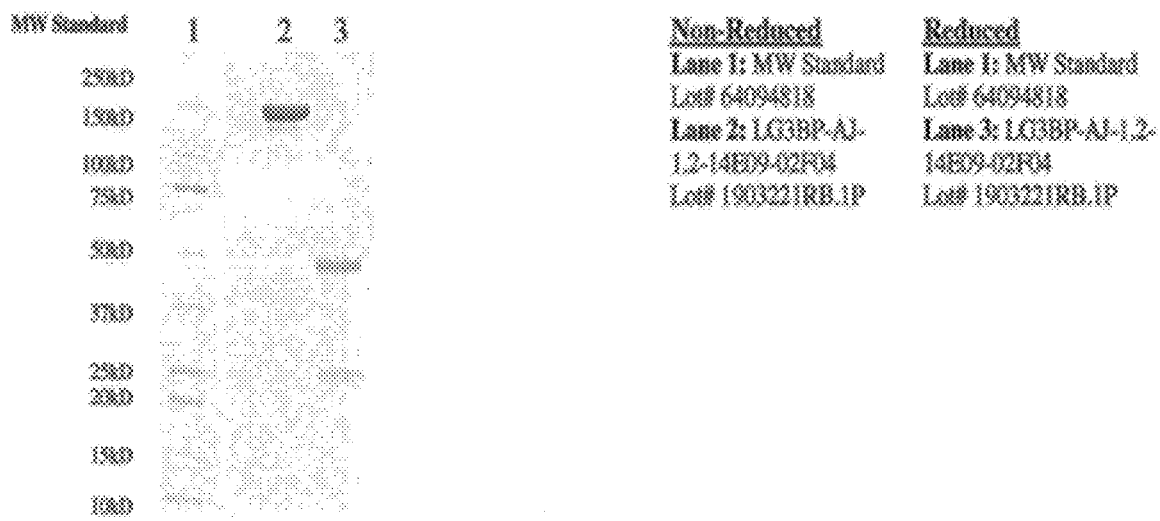
Figure 4B:
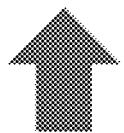

SDS-PAGE data for LG3BP VEYFIR clones are shown in FIGS. 4A-4C.

Figure 5A:
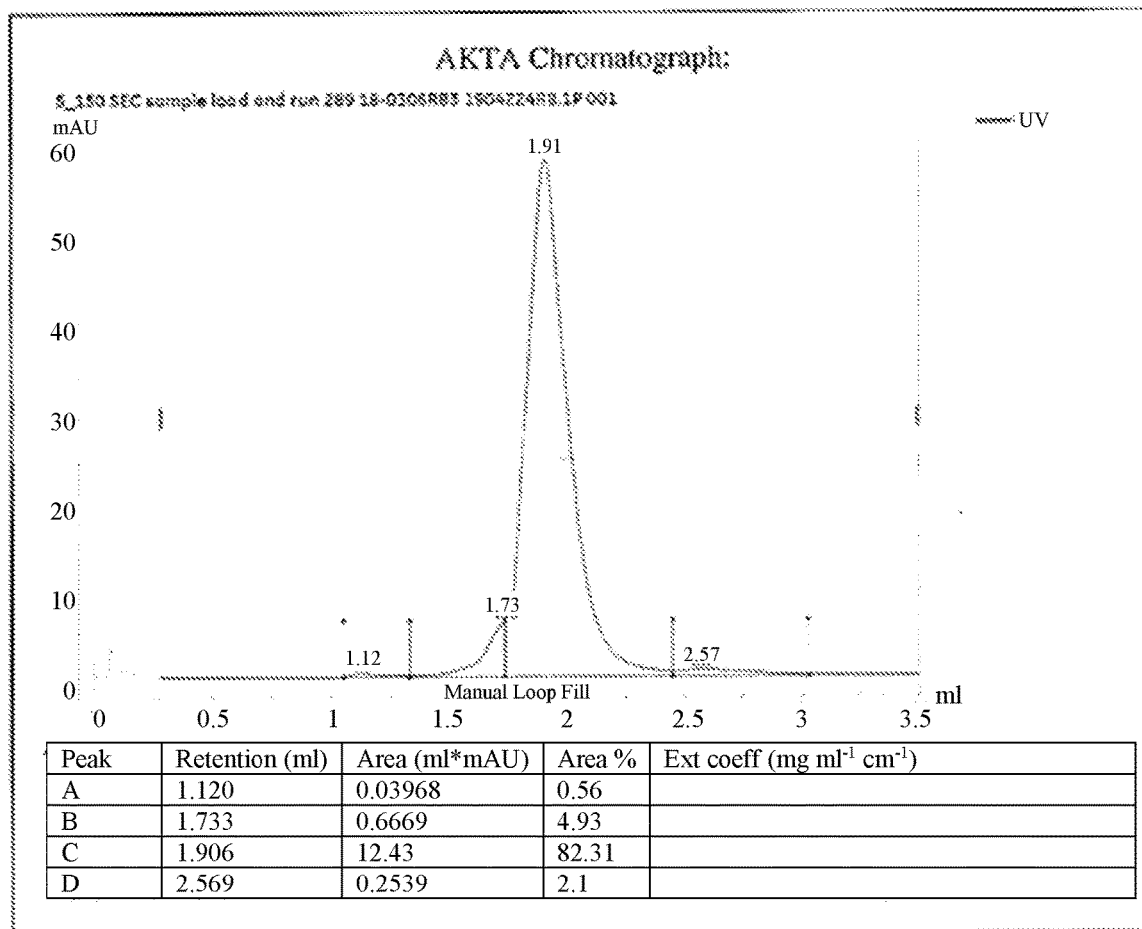
FIGS. 5A and 5B show SEC data for C163A INPA clones.
Figure 5B:
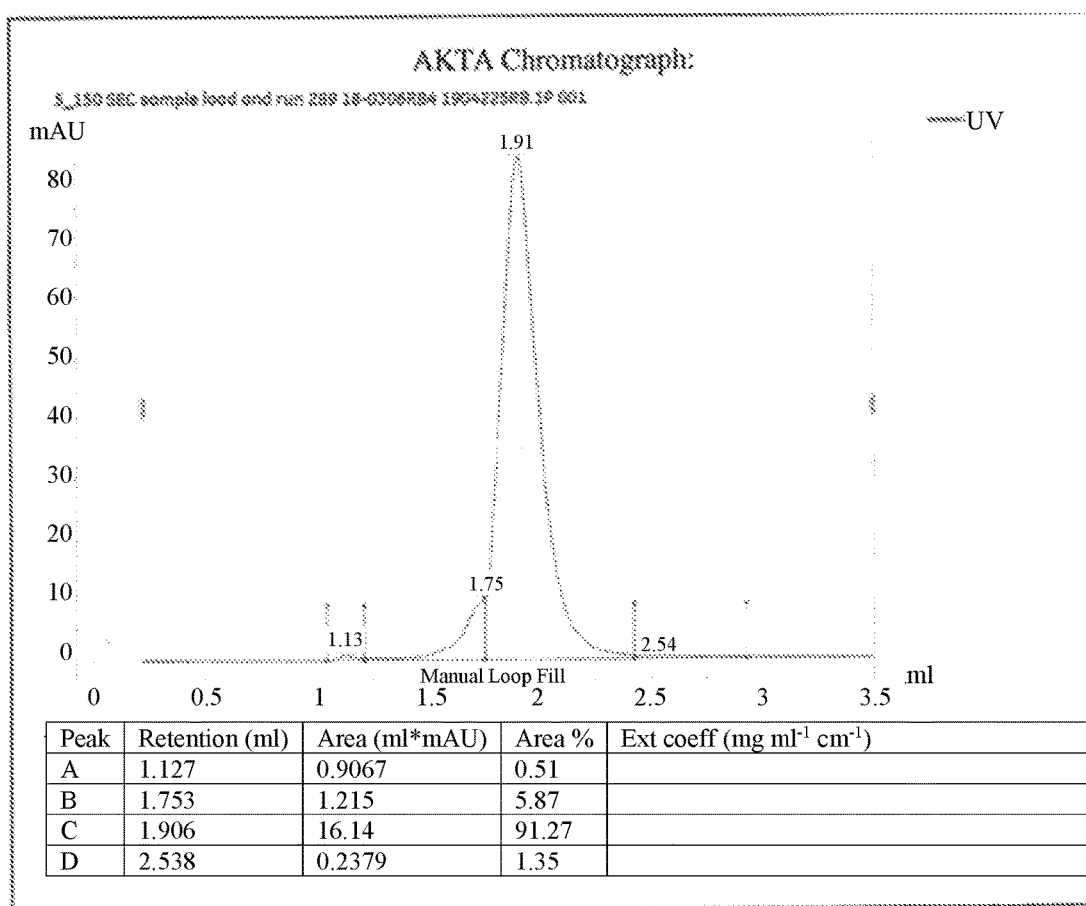

SEC data for C163A INPA clones are shown in FIGS. 5A and 5B.

Figure 6A:
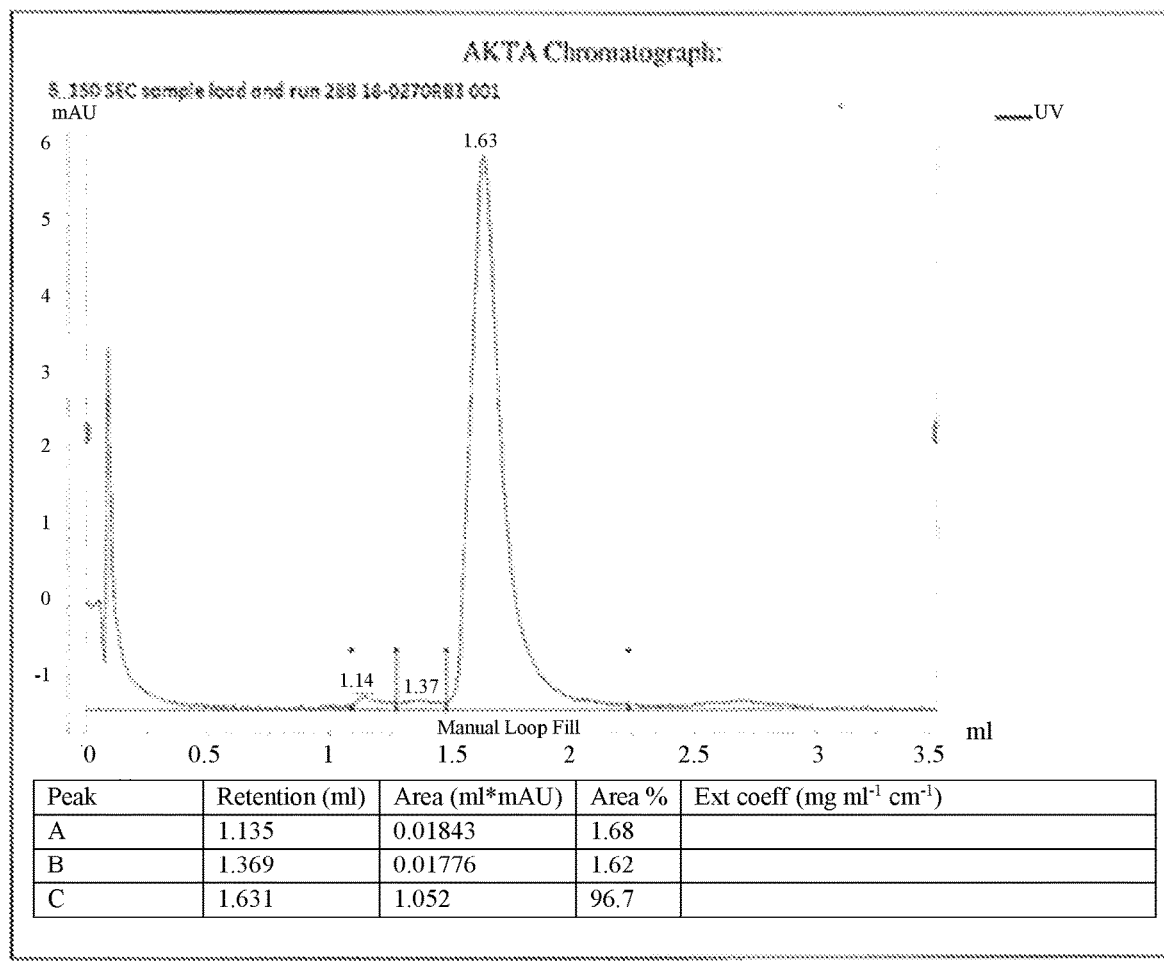
FIGS. 6A-6C show SEC data for LG3BP VEYFIR clones.
Figure 6B:
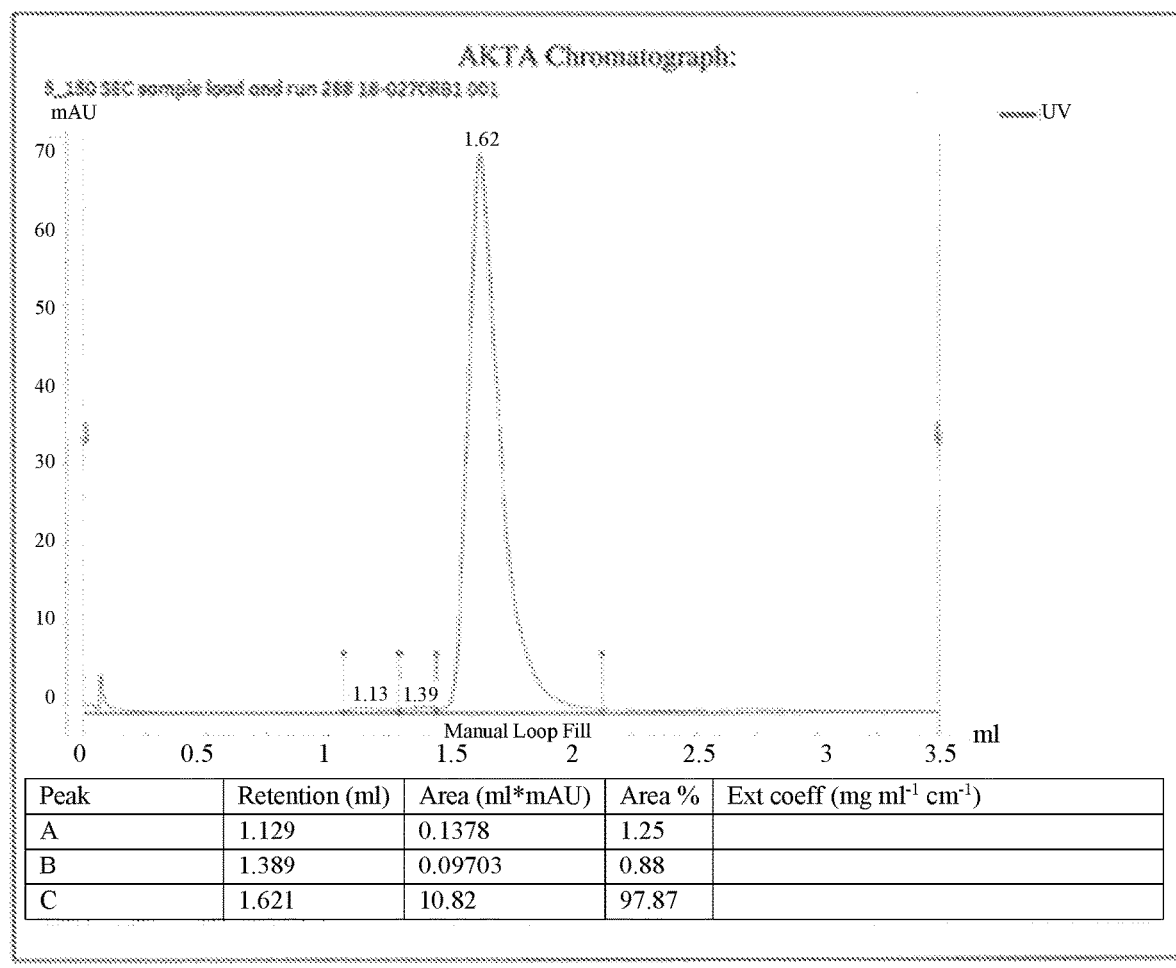
Figure 6C:
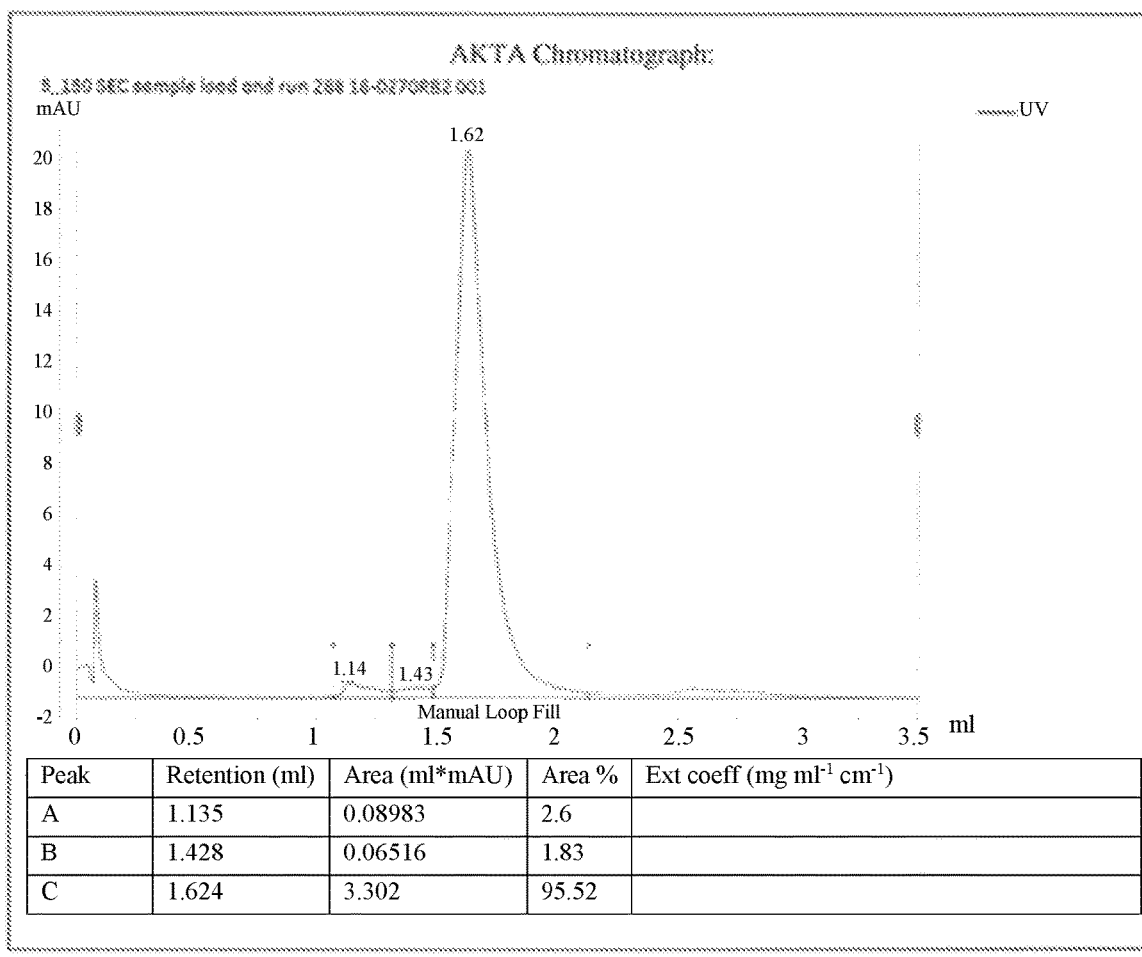

SEC data for LG3BP VEYFIR clones are shown in FIGS. 6A-6C.

ELISA data for C163A-BA-1.3-2H05-02F02 (INP detection in wells C 1-4 and D 1-4) and LG3BP-AJ-1.2-14E09-02F04 (VEIFYR(SEQ ID NO: 41) detection in wells A 1-4 and B 1-4) clones are shown in Tables 14 A-C. The VEIFYR (SEQ ID NO: 41) specific antibody was added to columns 1 (1:100 dilution), 2 (1:500 dilution) and the INPASLDK (SEQ ID NO: 44) specific antibody was added to columns 3 (1:100 dilution) and 4 (1:500 dilution).

TABLE 14A

Plate Layout for ELISA Verification of anti-INPASLDK (SEQ. NO: 44) and VEIFYR (SEQ ID NO: 41) Detection. Dilutions are shown for the respective peptides coated directly onto the plate 7A.

|   | 1 | 2 | 3 | 4 |
|---|---|---|---|---|
| A |   | VEI-A 1:50 |   |   |
| B |   | VEI-A_1:250 |   |   |
| C |   | INP-A_1:50 |   |   |
| D |   | INP-A_1:250 |   |   |

TABLE 14B

Plate layouts for the respective monoclonal antibodies used for specific detection of the plated peptides in FIG. 7A. Dilutions are shown and described above.

|   | 1 | 2 | 3 | 4 |
|---|---|---|---|---|
| A | VEI mAb | VEI mAb | INP mAb | INP mAb |
| B | LG3BP-F04 | LG3BP-F04 | INP-02F02A | INP-02F02A |
| C | 1:100 | 1:500 | 1:100 | 1:500 |
| D |   |   |   |   |
| E |   |   |   |   |
| F |   |   |   |   |
| G |   |   |   |   |
| H |   |   |   |   |

TABLE 14C

Results of ELISA reactivity for well coated with the respective INPASLDK (SEQ ID NO: 44) and VEIFYR (SEQ ID NO: 41) peptides and detected as described above.

| ◇ | 1 | 2 | 3 | 4 |
|---|---|---|---|---|
| A | 0.3 | 0.2 | 0.1 | 0.1 |
| B | 0.2 | 0.2 | 0.1 | 0.1 |
| C | 0.1 | 0.2 | 3.2 | 2.6 |
| D | 0.1 | 0.1 | 0.4 | 0.1 |

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A monoclonal antibody, or antigen-binding fragment thereof, wherein the monoclonal antibody or antigen-binding fragment thereof comprises:
   a heavy chain CDR1 (HC-CDR1) having an amino acid sequence of GFTFSSYA (SEQ ID NO: 1), a heavy chain CDR2 (HC-CDR2) having an amino acid sequence of ISSSGSYT (SEQ ID NO: 2), a heavy chain CDR3 (HC-CDR3) having an amino acid sequence of ARQEGLWSFAY (SEQ ID NO: 3), a light chain CDR1 (LC-CDR1) having an amino acid sequence of QSLLDSDGKTY (SEQ ID NO: 4), a light chain CDR2 (LC-CDR2) having an amino acid sequence of LVS (SEQ ID NO: 5), and a light chain CDR3 (LC-CDR3) having an amino acid sequence of WQGTHFPWT (SEQ ID NO: 6).

2. The monoclonal antibody, or antigen-binding fragment thereof, of claim 1, wherein the monoclonal antibody or antigen-binding fragment thereof comprises:
   a) a $V_H$ having an amino acid sequence of SEQ ID NO: 13; and
   b) a $V_L$ having an amino acid sequence of SEQ ID NO: 14.

3. The monoclonal antibody, or antigen-binding fragment thereof, of claim 1, wherein the monoclonal antibody, or antigen-binding fragment thereof, specifically binds to a peptide or protein comprising a sequence of INPASLDK (SEQ ID NO: 44).

4. The monoclonal antibody, or antigen-binding fragment thereof, of claim 1, wherein the monoclonal antibody, or antigen-binding fragment thereof, specifically binds to C163A.

5. The monoclonal antibody, or antigen-binding fragment thereof, of claim 1, wherein the monoclonal antibody, or antigen-binding fragment thereof, is chimeric, humanized, or murine.

6. The monoclonal antibody, or antigen-binding fragment thereof, of claim 1, wherein the monoclonal antibody, or antigen-binding fragment thereof, is detectably labeled.

7. The monoclonal antibody, or antigen-binding fragment thereof, of claim 1, wherein the monoclonal antibody, or antigen-binding fragment thereof, comprises an effector domain.

8. The monoclonal antibody, or antigen-binding fragment thereof, of claim 1, wherein the monoclonal antibody, or antigen-binding fragment thereof, comprises an Fc domain.

9. The monoclonal antibody, or antigen-binding fragment thereof, of claim 1, wherein the monoclonal antibody, or antigen-binding fragment thereof, is selected from the group consisting of Fv, Fav, F(ab')2, Fab', dsFv, scFv, sc(Fv)2, and diabodies fragments.

10. A monoclonal antibody, or antigen-binding fragment thereof, wherein the monoclonal antibody or antigen-binding fragment thereof comprises:
   (1) a HC-CDR1 having an amino acid sequence of GYTFSSYW (SEQ ID NO: 7, a HC-CDR2 having an amino acid sequence of INRSNGRT (SEQ ID NO: 8), a HC-CDR3 having an amino acid sequence of TKWGVTSDY (SEQ ID NO: 9), a LC-CDR1 having an amino acid sequence of SNVNY (SEQ ID NO: 10), a LC-CDR2 having an amino acid sequence of DTS (SEQ ID NO: 11), and a LC-CDR3 having an amino acid sequence of FQGSGYPRT (SEQ ID NO: 12).

11. The monoclonal antibody, or antigen-binding fragment thereof, of claim 10, wherein the monoclonal antibody or antigen-binding fragment thereof further comprises:
  a) a $V_H$ having an amino acid sequence of SEQ ID NO: 15; and
  b) a $V_L$ having an amino acid sequence of SEQ ID NO: 16.

12. The monoclonal antibody, or antigen-binding fragment thereof, of claim 10, wherein the monoclonal antibody, or antigen-binding fragment thereof, specifically binds to a peptide or protein comprising a sequence of VEIFYR (SEQ ID NO: 41).

13. The monoclonal antibody, or antigen-binding fragment thereof, of claim 10, wherein the monoclonal antibody, or antigen-binding fragment thereof, specifically binds to LG3BP.

14. The monoclonal antibody, or antigen-binding fragment thereof, of claim 10, wherein the monoclonal antibody, or antigen-binding fragment thereof, is chimeric, humanized, or murine.

15. The monoclonal antibody, or antigen-binding fragment thereof, of claim 10, wherein the monoclonal antibody, or antigen-binding fragment thereof, is detectably labeled.

16. The monoclonal antibody, or antigen-binding fragment thereof, of claim 10, wherein the monoclonal antibody, or antigen-binding fragment thereof, comprises an effector domain.

17. The monoclonal antibody, or antigen-binding fragment thereof, of claim 10, wherein the monoclonal antibody, or antigen-binding fragment thereof, comprises an Fc domain.

18. The monoclonal antibody, or antigen-binding fragment thereof, of claim 10, wherein the monoclonal antibody, or antigen-binding fragment thereof, is selected from the group consisting of Fv, Fav, F(ab')2), Fab', dsFv, scFv, sc(Fv)2, and diabodies fragments.

* * * * *